(12) United States Patent
Zuker et al.

(10) Patent No.: US 7,601,883 B2
(45) Date of Patent: Oct. 13, 2009

(54) MAMMALIAN SOUR/ACID TASTE AND CSF RECEPTOR GENES, POLYPEPTIDES AND ASSAYS

(75) Inventors: Charles Zuker, Del Mar, CA (US); Angela L. Huang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/483,423

(22) Filed: Jul. 6, 2006

(65) Prior Publication Data

US 2007/0065884 A1   Mar. 22, 2007

Related U.S. Application Data

(63) Continuation-in-part of application No. 11/176,958, filed on Jul. 6, 2005.

(60) Provisional application No. 60/741,352, filed on Nov. 30, 2005.

(51) Int. Cl.
G01N 33/00 (2006.01)
A01K 67/00 (2006.01)
A01K 67/027 (2006.01)

(52) U.S. Cl. .................................. 800/3; 800/8; 800/18
(58) Field of Classification Search ...................... 800/3, 800/8, 18
See application file for complete search history.

(56) References Cited

U.S. PATENT DOCUMENTS

2002/0037515 A1   3/2002   Margolskee et al.
2002/0127623 A1   9/2002   Minshull et al.

FOREIGN PATENT DOCUMENTS

| WO | WO 00/44929 A2 | 8/2000 |
| WO | WO 00/45179 A2 | 8/2000 |
| WO | WO 03/025137 A2 | 3/2003 |
| WO | WO 2004/034025 A2 | 4/2004 |
| WO | WO 2005/061548 A1 | 7/2005 |

OTHER PUBLICATIONS

Ristevski et al., Molecular Biotechnology, vol. 29, 2005, pp. 153-163.*
Montoliu et al., 2002, Cloning and Stem Cells, vol. 4, pp. 39-46.*
Houdebine et al., 2002, J. of Biotechnology, vol. 98, pp. 145-160.*
Zhao et al., 2003, Cell, vol. 115, pp. 255-266.*
Baker et al., 2000, Int. J. Human-Computer Studies, vol. 52 pp. 1-16.*
Rossant et al., 1998, TIG, vol. 14(9) pp. 358-363.*
Huang et al., 2006, Nature, vol. 442(7105), pp. 934-938.*
Alexander et al. (1992) "Altering the antigenicity of proteins" *Proc. Natl. Acad. Sci. USA* 89: 3352-3356.
Avenet & Lindemann (1989) "Perspectives in taste reception" *J Membr Biol*.112, 1-8.
Basora et al. (2002) "Tissue and Cellular Localization of a Novel Polycystic Kidney Disease-Like Gene Product, Polycystin-L" *J. Am. Soc. Nephrol* 13:293-301.
Bernhardt et al. (1996) "Changes in IP$_3$ and cytosolica $CA^{2+}$ in response to sugards and non-sugar sweeteners in transduction of sweet tast in the rat" *J. Physiol* 490:325-336.
Bowie et al. (1990) "Deciphering the Message in Protein Sequences: Tolerance to Amino Acid Substitutions" *Science* 247:1306-1310.
Doolin et al. (1996) "Distribution and Characterization of Functional Amiloride-sensitive Sodium Channels in Rat Tongue" *J. Gen. Physiol.* 107: 545-554.
Gilbertson et al., "The molecular physiology of taste transduction" *Curr. Opin. Neurobiol.* 10: 519-527, 2000.
Hoon et al. (1999) "Putative mammalian taste receptors: a class of taste-specific GPCRs with distinct topographic selectivity" *Cell* 96:541-51.
Kinnamon et al., (1992) "Chemosensory transduction mechanisms in taste" *Annu. Rev. Physiol.* 54:715-731.
Lin and Corey (2005) "TRP channels in mechanosensation" *Curr Opin Neurobiol.* 15(3):350-7.
Lindemann (1996) "Taste reception" *Physiol. Rev.* 76:718-766.
Liu et al. (2003) "Intracellular $Ca^{2+}$ and the phospholipids PIP$_2$ regulate the taster transduction ion channel TRPM5" *Proc. Natl. Acad. Sci. USA* 100(25): 15160-15165.
Madden et al. (1997) "Taste Perception in Cirrhosis: Its Relationship to Circulating Micronutrients and Food Preferences" *Hepatology* 26(1): 40-48.
Margolskee (1993) "The molecular biology of taste transduction" *R. Bioessays* 15, 645-650.
Mueller et al. (2005) "The receptors and coding logic for bitter taste" *Nature* 434 (7030): 225-9.
Nauli and Zhou 2004 "Polycystins and Mechanosensation in renal and nodal cilia" *Bioessays* 26.8 844-856.
Nelson et al. (2001) "Mammalian sweet taste receptors" *Cell* 106(3): 381-90.
Nelson et al. (2002) "An amino-acid taste receptor" *Nature* 416(6877): 199-202.
Nomura, et al. (1998) "Identification of PKDL, a novel polycystic kidney disease 2-like gene whose murine homologue is deleted in mice with kidney and retinal defects" *J. Biol.Chem.* 273:25967-25973.
Ogura et al. (1997) "Bitter Taste Transduction of Denatonium in the Mudpuppy *Necturus Maculosus*," *J. of Neuroscience*, 17(10): 3580-3587.

(Continued)

Primary Examiner—Peter Paras, Jr.
Assistant Examiner—David Montanari
(74) Attorney, Agent, or Firm—Quine Intellectual Property Law Group, P.C.; Paul Littlepage; Jonathan Alan Quine

(57) ABSTRACT

Acid/sour taste receptors are provided. CSF pH sensing receptors are provided. Methods and systems for screening for tastants and receptor modulators are provided. Knock out and transgenic animals, antibodies to the receptors, methods of detecting polymorphisms, and methods of correcting taste defects are also provided.

17 Claims, 16 Drawing Sheets

OTHER PUBLICATIONS

Roper et al. (1989) "Distribution of Ion Channels on Taste Cells and its Relations to Chemosensory Transduction," *J. Membrane Biology* 109(1): 29-39.

Roper (1989) "The cell biology of vertebrate taste receptors" *Ann. Rev. Neurosci.* 12:329-353.

Wu et al. (1998) "Identification of PKD2L, a Human PKD2-Related Gene: Tissue-specific Expression and Mapping to Chromosome 10q25" *Genomics* 54(3) 564-568.

Zhang et al. (2003) "Coding of sweet, bitter, and umami tastes: different receptor cells sharing similar signaling pathways" *Cell* 112(3):293-301.

Zhao et al. (2003) "The receptors for mammalian sweet and umami taste" *Cell* 115(3):255-66.

Chen et al. (1999) "Polycystin-L is a calcium-regulated cation channel permeable to calcium ions." *Nature*, 401: 383-385.

Inoue et al. (2003) "Transient Receptor Potential Protein as a Novel Non-Voltage-Gated $Ca^{+2}$ Entry Channel Involved in Diverse Pathophysiological Functions." *Journal of Pharmacological Sciences*, 91: 271-276.

Vigh et al. (2004) "The system of cerebrospinal fluid-contacting neurons. Its supposed role in the nonsynaptic signal transmission of the brain." *Histol Histopathol*, 19(2): 607-628.

* cited by examiner

```
cloneID529  ------------------------------------------------
rat         MNIMENSKEQELQTLGSRVWDNPAYSSPPSPNGTPRICTVSSVALPETQPKKPEVRRQEK
mouse       MNSMESPKNQELQTLGNRAWDNPAYSDPPSPNRTLRICTVSSVALPETQPKKPEVRCQEK
human       MNAVGSPEGQELQKLGSGAWDNPAYSGPPSPHGTLRMCTISSTGPLQPQPKKPEDEPQET cloneID529  ----------------------------------TAENRELYVKTTLRELVVYIVFLVDVCLLTYG
rat         TPRVPVSGCCILICRGIRGLWGTTLTENTAENRELYVKTTLRELVVYIVFLVDVCLLTYG
mouse       TQRTLVSSCCLHICRSIRGLWGTTLTENTAENRELYVKTTLRELVVYIVFLVDVCLLTYG
human       AYRTQVSSCCLHICQGIRGLWGTTLTENTAENRELYIKTTLRELIVYIVFLVDICLLTYG cloneID529  MTSSSAYYYTKVMSELFLHTPSDSGVSFQTISSMSDFWDFAQGPLLDSLYWTKWYNNQSL
rat         MTSSSAYYYTKVMSELFLHTPSESAVSFQTISSMSDFWDFAQGPLLDSLYWTKWYNNQSL
mouse       MTSSSAYYYTKVMSELFLHTPSDSGVSFQTISSMSDFWDFAQGPLLDSLYWTKWYNNQSL
human       MTSSSAYYYTKVMSELFLHTPSDIGVSFQAISSMADFWDFAQGPLLDSLYWTKWYNNQSL cloneID529  GRGSHSFIYYENLLLGAPRLRQLRVRNDSCVVHEDFREDILNCYDVYSPDKEDQLPFGPL
rat         GSSSHSFIYYENLLLGVPRLRQLRVRNDSCVVHEDFREDILNCYDVYSPDKEDQLPFGPL
mouse       GRGSHSFIYYENLLLGAPRLRHVRVRNDSCVVHEDFREDILNCYDVYSPDKEDQLPFGPQ
human       GHGSHSFIYYENMLLGVPRLRQLRVRNDSCVVHEDFREDILSCYDVYSPDKEQLPFGPF cloneID529  NGTAWTYHSQNELGGSSHWGRLTSYSGGGYYLDLPGSRQASAEALQGLQEGL--------
rat         NGTAWTYHSQNELGGSSHWGRLTSYSGGGYYLDLPGSRQASAEALQGLQEGLWLDRGTRV
mouse       NGTAWTYHSQNELGGSSHWGRLTSYSGGGYYLDLPGSRQASAEALQGLQEGLWLDRGTRV
human       NGTAWTYHSQDELGGFSHWGRLTSYSGGGYYLDLPGSRQESAEALRALQEGLWLDRGTRV cloneID529  ------------------------------------------------------------
rat         VFIDFSVYNANINLFCILRLVVEFPATGGAIPSWQIRTVKLIRYVNNWDFFIVGCEVIFC
mouse       VFIDFSVYNANINLFCILRLVVEFPATGGTIPSWQIRTVKLIRYVNNWDFFIVGCEVMFC
human       VFIDFSVYNANINLFCMLRLVVEFPATGGAIPSWQIRTVKLIRYVSNWDFFIVGCEVIFC cloneID529  ------------------------------------------------------------
rat         IFIFYYVEEILEIRVHREYLSSVWNILDLVVILLSIVAVGFHMFRTLEVNRLMGELLQ
mouse       VFIFYYVEEILEIHLHRLRYLSSVWNILDLVVILLSIVAVGFHIFRTLEVNRLMGKLLQ
human       VFIFYYVEEILERHIHRLSSIWNILDLVVILLSIVAVGFHIFRTLEVNRLMGKLLQ cloneID529  ------------------------------------------------------------
rat         QPDTYPDFEFLAFWQTQYNNMNAVNLFFAWIKIFKYISFNKTMTQLSSTLARCAKDILGF
mouse       QPDTYADFEFLAFWQTQDNNMNAVNLFFAWIKIFKYISFNKTMTQLSSTLARCAKDILGF
human       QPNTYADFEFLAFWQTQYNNMNAVNLFFAWIKIFKYISFNKTMTQLSSTLARCAKDILGF cloneID529  ------------------------------------------------------------
rat         AIMFFIVFFAYAQLGYLLFGTQVESFSTFVKCIFTQFRIILGDFDYNAIDNANRILGPVY
mouse       AVMFFIVFFAYAQLGYLLFGTQVENFSTFVKCIFTQFRIILGDFDYNAIDNANRILGPVY
human       AVMFFIVFFAYAQLGYLLFGTQVENFSTEIKCIFTQFRIILGDFDYNAIDNANRILGPAY cloneID529  ------------------------------------------------------------
rat         FITYVFFVFFVLLNMFLAIINDTYSEVKEELAGQRDQLQLSDLLKQSYSKTLQRLRLRKE
mouse       FVTYVFFVFFVLLNMFLAIINDTYSEVKEELAGQKDQLQLSDELKQSYNKTLLRLRLRKE
human       FVTYVFFVFFVLLNMFLAIINDTYSEVKEELAGQKDELQLSDLLKQGYNKTLLRLRLRKE cloneID529  ------------------------------------------------------------
rat         RVSDVQKVLKGGEPEIQFEDFTNTLRELGHAEREISEVSAAFTREFDRDGDHILDEEDQAQ
mouse       RVSDVQKVLKGGEPEIQFEDFTSTLRELGHEEHEIT---AAFTRFDQDGDHILDEEEQEQ
human       RVSDVQKVLQGGEQEIQFEDFTNTLRELGHAEHEITELTATFTKFDRDGNRILDEKEQEK cloneID529  ------------------------------------------------------------
rat         MRQGLEEERMTLSAETENLGRSVGHSPPGELDAEAARGRSWVSGEEFDMLTRRVLQLQRV
mouse       MRQGLEEERVTLNAEIENLGRSVGHSPPGELGAEAARGQSWVSGEEFDMLTRRVLQLQCV
human       MRQDLEEERVALNTEIEKLGRSIVSSPQGKSGPEAARKGGWVSGEEFYMLTRRVLQLETV cloneID529  ------------------------------------------------------------
```

Fig. 2A

```
rat       LEGVVSQMDALSSKLKMLERKGELAPSPGMAMPAVWEN---------------------
mouse     LEGVVSQIDAVGSKLKMLERKGELAPSPGMGEPAVWEN---------------------
human     LEGVVSQIDAVGSKLKMLERKGWLAPSPGVKDQAIWKHPQPAPAVTPDPWGVQGGQESEV cloneID529 ------------------------
rat       PYN---------------PS----
mouse     LYN---------------PS----
human     PYKREEEALEERRLSRGEIPILQRS
```

Fig. 2A cont.

```
mouse   MNSMESPKNQELQTLGNRAWDNPAYSDPPSPNRTLRICTVSSVALPETQPKKPEVRCQEK
rat     MNIMENSKEQELQTLGSRVWDNPAYSSPPSPNGTPRICTVSSVALPETQPKKPEVRRQEK
human   MNAVGSPEGQELQKLGSGAWDNPAYSGPPSPHGTLRVCTISSTGPLQPQPKKPEDEPQET mouse   TQRTLVSSCCLHICRSIRGLWGTTLTENTAENRELYVKTTLRELVVYIVFLVDVCLLTYG
rat     TPRVPVSGCCLLICRGIRGLWGTTLTENTAENRELYVKTTLRELVVYIVFLVDVCLLTYG
human   AYRTQVSSCCLHICQGIRGLWGTTLTENTAENRELYIKTTLRELIVYIVFLVDICLLTYG mouse   MTSSSAYYYTKVMSELFLHTPSDSGVSFQTISSMSDFWDFAQGPLLDSLYWTKWYNNQSL
rat     MTSSSAYYYTKVMSELFLHTPSESAVSFQTISSMSDFWDFAQGPLLDSLYWTKWYNNQSL
human   MTSSSAYYYTKVMSELFLHTPSDTGVSFQAISSMADFWDFAQGPLLDSLYWTKWYNNQSL mouse   GRGSHSFIYYENLLLGAPRLRHVRVRNDSCVVHEDFREDILNCYDVYSPDKEDQLPFGPQ
rat     GSSSHSFIYYENLLLGVPRLRQLRVRNDSCVVHEDFREDILNCYDVYSPDKEDQLPFGPL
human   GHGSHSFIYYENMLLGVPRLRQLKVRNDSCVVHEDFREDILSCYDVYSPDKEEQLPFGPF mouse   NGTAWTYHSQNELGGSSHWGRLTSYSGGGYYLDLPGSRQASAEALQGLQEGLWLDRGTRV
rat     NGTAWTYHSQNELGGSSHWGRLTSYSGGGYYLDLPGSRQASAEALQGLQEGLWLDRGTRV
human   NGTAWTYHSQDELGGFSHWGRLTSYSGGGYYLDLPGSRQGSAEALRALQEGLWLDRGTRV mouse   VFIDFSVYNANINLFCILRLVVEFPATGGTIPSWQIRTVKLIRYVNNWDFFIVGCEVMFC
rat     VFIDFSVYNANINLFCILRLVVEFPATGGAIPSWQIRTVKLIRYVNNWDFFIVGCEVIFC
human   VFIDFSVYNANINLFCMLRLVVEFPATGGAIPSWQIRTVKLIRYVSNWDFFIVGCEVIFC mouse   VFIFYYVVEEILEIHLHRLRYLSSVWNILDLVVILLSIVAVGFHIFRTLEVNRLMGKLLQ
rat     IFIFYYVVEEILEIRVHRFRYLSSVWNILDLVVILLSIVAVGFHVFRTLEVNRLMGELLQ
human   VFIFYYVVEEILELHIHRLRYLSSIWNILDLVVILLSIVAVGFHIFRTLEVNRLMGKLLQ mouse   QPDTYADFEFLAFWQTQDNNMNAVNLFFAWIKIFKYISFNKTMTQLSSTLARCAKDILGF
rat     QPDTYPDFEFLAFWQTQYNNMNAVNLFFAWIKIFKYISFNKTMTQLSSTLARCAKDILGF
human   QPNTYADFEFLAFWQTQYNNMNAVNLFFAWIKIFKYISFNKTMTQLSSTLARCAKDILGF mouse   AVMFFIVFFAYAQLGYLLFGTQVENFSTFVKCIFTQFRIILGDFDYNAIDNANRILGPVY
rat     AIMFFIVFFAYAQLGYLLFGTQVESFSTFVKCIFTQFRIILGDFDYNAIDNANRILGPVY
human   AVMFFIVFFAYAQLGYLLFGTQVENFSTFIKCIFTQFRIILGDFDYNAIDNANRILGPAY mouse   FVTYVFFVFFVLLNMFLAIINDTYSEVKEELAGQKDQLQLSDFLKQSYNKTLLRLRLRKE
rat     FITYVFFVFFVLLNMFLAIINDTYSEVKEELAGQRDQLQLSDLLKQSYSKTLQRLRLRKE
human   FVTYVFFVFFVLLNMFLAIINDTYSEVKEELAGQKDELQLSDLLKQGYNKTLLRLRLRKE mouse   RVSDVQKVLKGGEPEIQFEDFTSTLRELGHEEHEI----TAAFTRFDQDGDHILDEEEQEQ
rat     RVSDVQKVLKGGEPEIQFEDFTNTLRELGHAEREISEVSAAFTRFDRDGDHILDEEDQAQ
human   RVSDVQKVLQGGEQEIQFEDFTNTLRELGHAEHEITELTATFTKFDRDGNRILDEKEQEK mouse   MRQGLEEERVTLNAEIENLGRSVGHSPPGELGAEAARGQSWVSGEEFDMLTRRVLQLQCV
rat     MRQGLEEERMTLSAETENLGRSVGHSPPGELDAEAARGRSWVSGEEFDMLTRRVLQLQRV
human   MRQDLEEERVALNTEIEKLGRSIVSSPQGKSGPEAARAGGWVSGEEFYMLTRRVLQLETV mouse   LEGVVSQIDAVGSKLKMLERKGELAPSPGMGEPAVWENLYNPS----------------
rat     LEGVVSQVDALSSKLKMLERKGELAPSPGMAMPAVWENPYNPS----------------
human   LEGVVSQIDAVGSKLKMLERKGWLAPSPGVKEQAIWKHPQPAPAVTPDPWGVQGGQESEV mouse   ------------------------
rat     ------------------------
human   PYKREEEALEERRLSRGEIPTLQRS
```

Fig. 2B

```
rat   MLLQRPSWLWLYERISVMLGVILLGREPSIPEQHGKNSCYQLNRLMCSFHEAEMYCHAQRG
mouse MLLQRRSWLWLYIRIGVILGDILGRKPSIREQHGGNSCYQLNRLFCDFQEADNYCHAQRG
human MFFKGGSWLWLYIRTSEILGSELNS----PAPHGQNNCYQLNRFQCSFEEAQHYCHVQRG rat   HLANTWNPKLQDFLQNSPQKETVWWVGINLKLPRKQPGITQTG----AAAKKPDECTSVV
mouse RLAHTWNPKLRGFLKSELNEETVWWVRGNLTLPGSHPGINQTGGDDVLRNQKPGECPSVV
human FLAHIWNKEVQDLIRDYLEEGKKWWIGQNMMPLKHQDNKYPADVAANGPPKPLSCTYIS rat   KRSNAFFPRWDQCLKKHHFICQAALGCRGKMGKEMRPWHRKTRRPEAMSSKKYASLHLED
mouse THSNAVFSRWNLCEEKHHFICQAAA-----------------------------------
human RNFIRISSKGDKCLLKYYFICQTGD----------------------------------- rat   QDGRESVWSGPQQLRLLPVSPHKVRFSVWHRLALQLNPVAVPPQGANIWRNELDP--NKP
mouse ----------------------------------------FPPQGASIWRNEFGPGPLLP
human ----------------------------------------FLDGDAHYERNGNNSHLMQR rat   MKK--RGAEIERHMIP-GDGPPLSMCHPPAPPELSEILCFPIDPVSSVLPKATHKMTITS
mouse MKR--RGAETERHMIP-GNGPPLAMCHQPAPPELFETLCFPIDPASSAPPKATHRMTITS
human HKKTKRGVAIARDKMPPGPGHLPITCHYPLPAHLSKTLCHPISQFPSVL----------- rat   PTRSSQVTSVVTASSSPPQVTSDTPASSS------------SPPQVTSDTPASSS-----
mouse LTGRPQVTSDTLASSSPPQGTSDTPASSSPPQVTSATSASSSPPQGTSDTPASSSPPQVT
human ------------------------------------------------------------ rat   -------SPPQVTSDTPSSSSPPQVTSDTPASSSLPQVTSDTPASSSPPQVTSDTPASS
mouse SATSASSSPPQGTSDTPASSS-PPQVTSATSASSSPPQGTSDTPASSSPPQVTSATSASS
human ------------------------------------------------------------ rat   SPPQVTSDTPASSSPPQVTSDTPASSSPPQVTSDTSASSSPPQVTSDTPASSSPPQVTSD
mouse SPPQGTSDTPASSSPPQGTLDTPSSSSPPQGTSDTPASSSPPQGTSETPASNSPPQGTSE
human ------------------------------------------------------------ rat   TPASSITPQVTTDTPVSSSPPQVTSDTPASSSPPQVTSDTPASSSPLQVTSDTTASSSPP
mouse TPGFSSPPQVTTATLVSSSPPQVTSETPASSSPTQVTSETPASSSPTQVTSDTPASNSPP
human ------------------------------------------------------------ rat   QVTSDTPASSSSPLQVTSDTPASSITPQVTSDTPVSSSPPQVTSDTPASSSSPPQVTSDT
mouse QGTSDTPG-FSSPTQVTIATLVSSSPPQVTSDTPASSSPPQVTSDTPASSS-PPQVTSET
human --------------------SSITSQVTS------------------------------- rat   PASSSSPPQVTSDTPSSSSSPPQVTSDTPASSSLPQVTSDTPASSSPPQVTSDTPASSSP
mouse PASSS-PPQVTSDT-SASISPPQVISDTPASSSPPQVTSETPASSSPTNMTSDTPASSSP
human ------------------------------------AASEP------------------- rat   PQVTSDTPASSSSPLQVTSDTPVPNSPPWPVITEVTRLESTIPTGRSLADITLNAKEDSP
mouse TNMTSDTPASSS-PTNMTSDTPASSSPPWPVITEVTRPESTIPAGRSLANITSKAQEDSP
human --------------------SSQPLPVITQLTMPVSVTHAGQSLAETTSSPKEEGH rat   PGVISTHPQMSFQSSTNQLPIARIASGNSSFQWVMGWQLQPPAPRIFIVFAPQSVKATIR
mouse IGVISTHPQMSFQSST--------------------------------------------
human PNTFISYLQMSLQKAS-------------------------------------------- rat   SRSHLSSPTIFSPQQVIEETAGKLILANPASQAHSEFQKACSILQRLRDFLPTSSTSAQV
mouse -------------SQAIDETAGERVPTIPDFQAHSEFQKACAILQRLRDFLPTSPTSAQV
human -------------GQVIDEIAGNFSRAVHGLQALNKLQEACEFLQKLTALTPRFSKPAQV rat   SVASLLIDLSEQLLTLPFQRNNSWSSHTPAVSCPFQPLGSLLTTKKNSHQMAQQDTEQVE
```

Fig. 4

```
mouse  SVANLLIDLSEQLLVLPFQKNNSWSSQTPAVSCPFQPLGRLTTTEKSSHQMAQQDMEQVE
human  NLINSLIYLSEELLRIPFQNNSLGFKVPPTVCPFHSLNNVTKAGEGSWLESKRHTEPVE rat    DMLETSLMALGEIHRTFCQQSLCPQSAVTLASPTATLMLSSQNVSSLPLSTYTLGEPAPL
mouse  DMLETSLMALGEIHRAFCQQSLCPQSAVTLASPSATLMLSSQNVSTLPLSTYTLGEPAPL
human  DILEMSLVEFGNIGEAFLEQNQSPESSVTLTSANATLLLSRQNISTLPLSSYTLGHPAPV rat    RLGFPSAEALKELLDKHPGVNLQVTGLAFNPFETSDDSNIVGSIGNVLLSSEYQLIRVHD
mouse  TLGFPSAEALKELLNKHPGVNLQVTGLAFNPFKTLDDKNIVGSIGNVQLSSAYQSIRVHD
human  RLGFPSALALKELLNKHPGVNVQITGLAFNPFKDLDNRNIVGSIGSVLLSANRKLIQVHD rat    LIEDIEIVLWRNASMETQPTSLNTSTDCFTISVNITSLEKTLIVTIEPESPILMTLHLGF
mouse  LIEDIEIMLWRNASMETQPTSLNTSTDHFTISVNITSLEKTLIVTIEPESPILMTLHLGF
human  LIEDTEIMLWRNVSLETHPTSLNMSTHQLTTIVNMTSLEKSLIVSIDPESPILMTLYLGF rat    QDKPGHTHFYLNISLPRGQVWQKDEEYTWVLTPESLWYGTGTYYIMAVENKSAETAQHTP
mouse  QDQLAHTHFYLNISLPRDQVWQKDEEYTWVLTPENLWYGTGTYYIMAVENKSTEAAQHTP
human  QYQPNCTHFHLNIILPKDKVWQKDEEYTWVLNPEHLQHGIGTYYITAVLSERQEAQQTP rat    VLVSVVTAVTQCYFWDRYNRTWKSDGCQVGPKSTILKTQCLCDHLTFFSSDFFIVPRTVD
mouse  VLVSVVTAVTQCYFWDRYNRTWKSDGCQVGPKSTILKTQCLCDHLTFFSSDFFIVPRTVD
human  SLVSVITAVTQCYYWEIHNQTWSSAGCQVGPQSTILRTQCLCNHLTFFASDFFMVPRTVN rat    VENTIKLLLHVSNNPVGVSLLASLLGFYILLATWAWRKDQADTQKVKVTVLADNDPSSAF
mouse  VENTIKLLLHVTNNPVGVSLLSSLLGFYILLAMWASRKDREDMQKVKVTVLADNDPSSAS
human  VEDTIKLFLRVTNNPVGVSLLASLLGFYVITVQWARKKDQADMQKVKVTVLADNDPSAQF rat    HYLIQVYTGYRRRAATTAKVVITLYGSEGHSEPHHLCDPQKTVFERGALDVFLLSTGSWL
mouse  HYLIQVYTGYRRRAATTAKVVITLYGSEGHSEPHHLCDPEKTVFERGALDVFLLSTGSWL
human  HYLIQVYTGYRRSAATTAKVVITLYGSEGRSEPHHLCDPQKTVFERGELDVFLLTTWISL rat    GDLHGLRLWHDNSGNSPSWYVSQVMVSDMTVKKKCHFQCNCWLAMDLGNCERDRVFTPAS
mouse  GDLHGLRLWHDNSGDSPSWYVSQVIVSDMTTRKKWHFQCNCWLAVDLGNCERDRVFTPAS
human  GNLHSLRLWHDNSGVSPSWYVSQVIVCDMAVKRKWHEICNCWLAVDLGDCELDRVFIPVS rat    RSELSSFRHLFSSTIVEKFTQDYLWLSVATRHPWNQFTRVQRLSCCMTLLLCDMVINVMF
mouse  RSELSSFRHLFSSTIVEKFTQDYLWLSVATRHPWNQFTRVQRLSCCMALLLCDMVINIMF
human  KRELFSFRHLFSSMIVEKFTQDYLWLSIATRHPWNQFTRVQRLSCCMTLLLCNMVINVMF rat    WKMGGSTAKRG-ERLGPLAVTLSELLVSIQTSVILFPIHLVFGRLFQLVHPPEVLPPLPL
mouse  WKMGGTTAKRGTEQLGPLAVTLSELLVSIQTSIILFPIHLIFGRLFQLIHPPEALPQLPF
human  NKINSTTAKRD-EQMRPFAVAWSELLVSIHTAVILFPINLVIGRLFPLIEPQETLPLFPP rat    SQAACPSVLVRETPSLTQVVKELKETVGFLLRRNTHLLSECEQSSWSSCDINTLVKLLSG
mouse  IQAAWPPALVCESPSLTQVVKELKETVGFLLRRNTQLLSECEPSSCSSCDINKLAKLLSG
human  IQASCLSDASVEPLSATMVVEELKETVRFLLRRNTYLLSKCEQPPWSSWDITKLVKLLSS rat    LVYSHLEDQGCHQQTESRWEDGVSESHSHFCRYLLRVLQSLKLRLGALAAVQEHQPYDFS
mouse  LIYCHLEDEGCHQQTESHWEDAVSENHYHFCRYLLQILRRLKAHLEALGATQDHQSCDFS
human  LVSSHLEGQGCHQQGERHWARVVPENHHHFCCYLHRVLQRLKSHLGTLGLTQGHQSCDFL rat    EAVSQLQNLQELLRTQTLPKEPRPCRHSTSFPILNTEGGKKPVPFCLFRWLRYSCWLLLG
mouse  EAVSQLQNLQELLETQTLRRGPGPCRHSTSFPILSPGEGKKPMSFCLFRWLKCSCWLLLG
human  DAASQLQKLQELLETHILPTEQEPSREVTSFAILSSEEGKKPISNGLSKWLTSVCWLLLG rat    VISLTSAFFITLYSLELSRDQATSWVISMMLSVLQDIFICQPIKVIFLTLLFSLMANHMP
```

Fig. 4 cont.

```
mouse  VISLASAFFITLYSLELDKDQATSWVISMMLSVLQDIFISQPIKVIFLTLLFSLMANHMP
human  FTSLASAFFTALYSLELSKDQATSWMISIILSVLQNIFISQPMKVMFFTFLMSLMMSRMP rat    WLTKDKEHHARRIVALWAKCPSSAPGLRDKNNPIYTAPAMNHLDRRTKKVWR-KRLFLLT
mouse  WLNKDKEQHARRIVALWAKCPWSAPGLRDKNNPIYTAPAMNNLAKPTRKAWK-KQLSKLT
human  RLNKENEQQTKRIDALLAKCSSSVPGSRDKNNPMYVAPAINSPTKHPERTLKKKKLFKLT rat    AGSLVQILFLTLLMTTVYSAKDSSRFFLHRAMWKRFSHGFSEIKAVEDFYPWANRTLLPN
mouse  GGILVQILFLTLLMTTVYSAKDSSRFFLHRAIWKRFSHRFSEIKTVEDFYPWANGTLLPN
human  GDILVQILFLTLLMTAIYSAKNSNRFMLHQAIWKTFSHQFSEIKLLQDFYPWANHILLPS rat    LYGDYREEHHSAEQRGHLLRLAPTYQHDTRVDFSALAVRVPLFRGRGLGPALDDRSECSE
mouse  LYGDYR------------------------------------------------------
human  LYGDYR------------------------------------------------------ rat    QCLAQGFITDGNSFLLGNVLLRQILFPNDTHSPVSLHEHMNSYPQHQEDRENYGAGWVPP
mouse  -----GFITDGNSFLLGNVLIRQTRIPNDIFFPGSLHKQMKSPPQHQEDRENYGAGWVPP
human  ---------------------GKNAMLEPSHCKCGMQLIFQ---------------IPR rat    DTNITKADSIWHYQSPESLGGYPIQGEVTTYSGGGYVVRLGRNHSAATRVLQHLEQRHWL
mouse  DTNITKVDSIWHYQNQESLGGYPIQGELATYSGGGYVVRLGRNHSAATRVLQHLEQRRWL
human  TKTYEKVD---------------EGQLAFCDNG-------HTCGRPKSLFPGLHLRRES rat    DHYTKALFVEFTVFNANVNLLCMVTLILESSGVGTFFTSLRLDSLTSLQSSERGFAW-II
mouse  DHCTKALFVEFTVFNANVNLLCAVTLILESSGVGTFITSLQLDSLTSLQSSERGFAW-IV
human  YICSPRPMVLIPTDELHERLTSKNENGFSYIMRGAFFTSLRLESFTSLQMSKKGCVWSII rat    SQVAYYLLVCYYAFMQGCRLKRQGLAFFTRRRNILDTSIILTSFSILGLNMQSLSLLHTN
mouse  SQVMYYLLVCYYAFIQGCRLKRQRLAFFTRKRNLLDTSIVLISFSILGLSMQSLSLLHKK
human  SQVIYYLLVCYYAFIQGCQLKQQKWRFFTGKRNILDTSIILISFILLGLDMKSISLHKKN rat    MQQYRRDPDGFISFSEALRVNSVATHLMGFLLLFATVRVWDLLRHHARLQVINKTLLKAW
mouse  MQQYHCDRDRFISFYEALRVNSAVTHLRGFLLLFATVRVWDLLRHHAQLQVINKTLSKAW
human  MARYRDDQDRFISFYEAVKVNSAATHLMGFPVLLATVQLWNLLRHSPRLRVISRTLSRAW rat    DEVLGFIMIIMILLSSYAMTFNLLFGWSISDYQSFFSSMVTVVGLLMGIPKHKEVMALSP
mouse  DEVLGFILIIVMLLSSYAMTFNLLFGWSISDYQSFFRSIVTVVGLLMGTSKHKEVIALYP
human  DEVMGFLLIILILLTGYAIAFNLLFGCSISDYRIFFSSAVTVVGLLMGISHQEEVFALDP rat    VLGSFLVLSNIILMGLVIINLFVSAILIVFGKERKACEKEATLTDMLLQKLSSLLGIRQH
mouse  ILGSLLVLSSIILMGLVIINLFVSAILIAFGKERKACEKEATLTDMLLQKLSSLGIRLH
human  VLGIFLILTSVILMVLVMINLFVSAILMAFGKERKSLKKEAALIDTLLQKLSNLLGISWP rat    QKPASEKHADSTGY----------
mouse  QNPS-EEHADNTGY----------
human  QKTSSEQAATIAVGSDTEVLDELP
```

Fig. 4 cont.

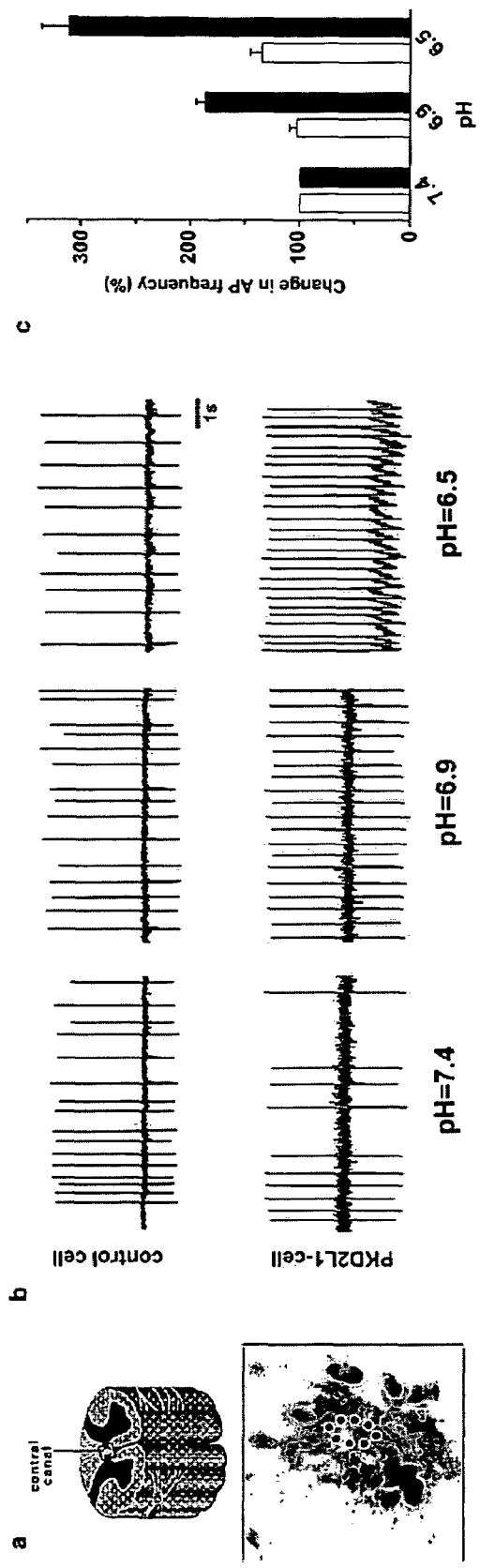

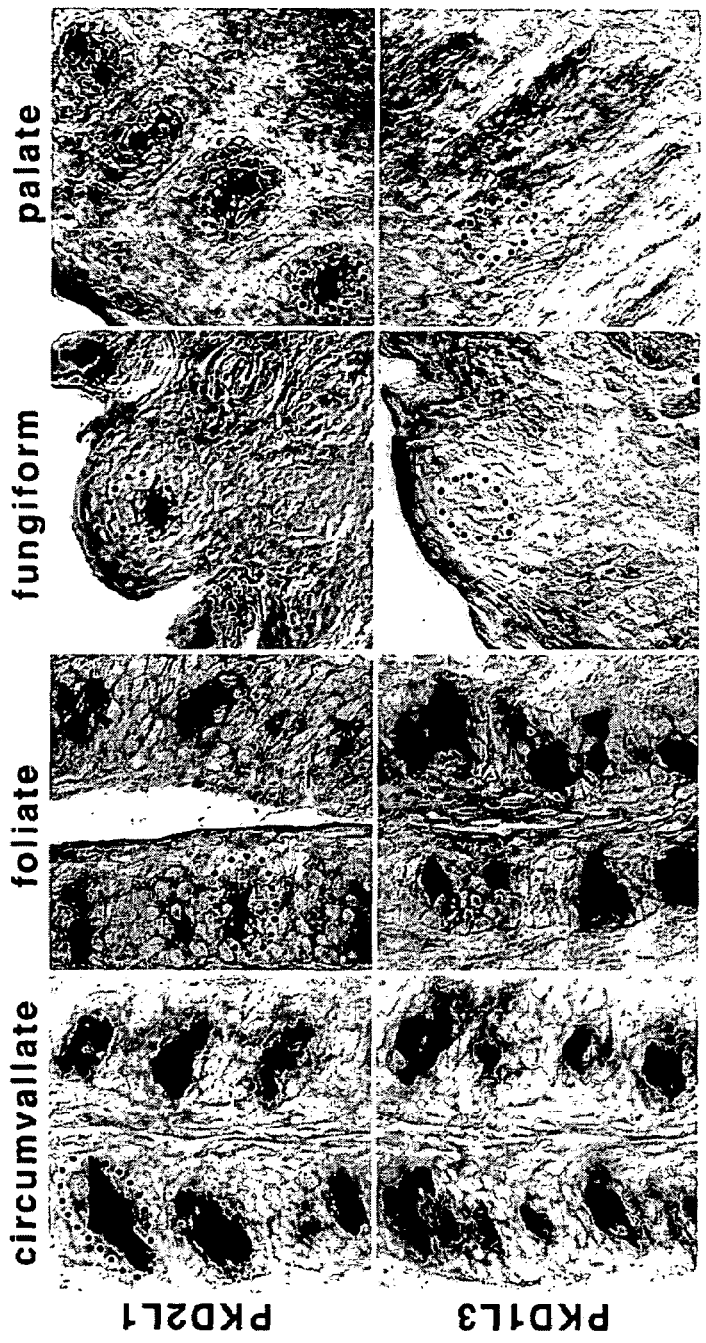
Fig. 8A
Fig. 8B

SEQUENCE LISTING

<160> NUMBER OF SEQ ID NOS: 19

<210> SEQ ID NO 1
<211> LENGTH: 612
<212> TYPE: DNA
<213> ORGANISM: Mus musculus

<400> SEQUENCE: 1

```
acagccgaga acagggagct ttatgtcaag accaccctga gggagcttgt ggtatacata     60
gtgttcctcg tggacgtctg tctgttgacc tacggaatga caagttctag tgcctattac    120
tacaccaaag tgatgtctga gttgttccta cacaccccat ccgactctgg agtctccttc    180
cagaccatca gcagcatgtc agacttctgg gattttgctc agggcccact cctgacagt     240
tgtactgga caaagtggta caacaaccag agcctggggc gtggctccca ctccttcatc    300
tactatgaga acctgctcct gggagcccca aggttgcggc agctgcgcgt gcgcaatgac    360
tcctgtgtgg ttcatgaaga cttccgggag acatttgta actgttatga tgtgtactcg    420
ccggacaaag aagatcagct ccccttggga cctctgaacg gcacagcgtg gacataccat    480
tcccagaatg agctgggtgg ctcctcccac tggggcaggc tcacaagcta cagcggggt     540
ggctactact ggatcttcc aggatcccga caagccagtg cagaggccct ccaaggactc    600
caggagggac tg                                                        612
```

<210> SEQ ID NO 2
<211> LENGTH: 204
<212> TYPE: PRT
<213> ORGANISM: Mus musculus

<400> SEQUENCE: 2

```
Thr Ala Glu Asn Arg Glu Leu Tyr Val Lys Thr Thr Leu Arg Glu Leu
1               5                   10                  15

Val Val Tyr Ile Val Phe Leu Val Asp Val Cys Leu Leu Thr Tyr Gly
                20                  25                  30

Met Thr Ser Ser Ser Ala Tyr Tyr Tyr Thr Lys Val Met Ser Glu Leu
            35                  40                  45

Phe Leu His Thr Pro Ser Asp Ser Gly Val Ser Phe Gln Thr Ile Ser
        50                  55                  60

Ser Met Ser Asp Phe Trp Asp Phe Ala Gln Gly Pro Leu Leu Asp Ser
65                  70                  75                  80

Leu Tyr Trp Thr Lys Trp Tyr Asn Asn Gln Ser Leu Gly Arg Gly Ser
                85                  90                  95

His Ser Phe Ile Tyr Tyr Glu Asn Leu Leu Leu Gly Ala Pro Arg Leu
            100                 105                 110

Arg Gln Leu Arg Val Arg Asn Asp Ser Cys Val Val His Glu Asp Phe
        115                 120                 125

Arg Glu Asp Ile Leu Asn Cys Tyr Asp Val Tyr Ser Pro Asp Lys Glu
    130                 135                 140

Asp Gln Leu Pro Phe Gly Pro Leu Asn Gly Thr Ala Trp Thr Tyr His
145                 150                 155                 160

Ser Gln Asn Glu Leu Gly Gly Ser Ser His Trp Gly Arg Leu Thr Ser
                165                 170                 175

Tyr Ser Gly Gly Gly Tyr Tyr Leu Asp Leu Pro Gly Ser Arg Gln Ala
            180                 185                 190

Ser Ala Glu Ala Leu Gln Gly Leu Gln Glu Gly Leu
```

<210> SEQ ID NO 3
<211> LENGTH: 2283
<212> TYPE: DNA
<213> ORGANISM: Mus musculus

<400> SEQUENCE: 3

| | | | | | |
|---|---|---|---|---|---|
| atgaaagtat | ggaaagcccc | aagaatcagg | agctacaaac | cctggggaac | agagcctggg | 60 |
| acaatcctgc | ctacagcgac | cctccttccc | cgaacaggac | gctgaggatc | tgcactgtct | 120 |
| ccagtgtggc | tctccctgag | actcaaccca | aaaagccaga | agtcagatgc | aggagaaga | 180 |
| cacagagaac | cctggtgtcc | agctgctgtc | tccatatctg | tcggagcatc | agaggactgt | 240 |
| ggggacaac | gctgactgag | aacacagccg | agaacaggga | gctttatgtc | aagaccaccc | 300 |
| taagggagct | tgtggtatac | atagtgttcc | tcgtggacgt | ctgtctgttg | acctacggaa | 360 |
| tgacaagttc | tagtgcctat | tactacacca | aagtgatgtc | tgaattgttt | ctacacaccc | 420 |
| catccgactc | tggagtctcc | ttccaaacca | tcagcagcat | gtcagacttc | tgggattttg | 480 |
| ctcagggccc | actcctggac | agtttgtact | ggacaaagtg | gtacaacaac | cagagcctgg | 540 |
| ggcgtggctc | ccactccttc | atctactatg | agaacctgct | cctgggagcc | caaggttgc | 600 |
| ggcacgtgcg | cgtgcgcaat | gactcctgtg | tggttcatga | agacttccgg | gaggacattt | 660 |
| tgaactgtta | tgatgtgtac | tcgccggaca | agaagatca | gctccccttt | ggacctcaga | 720 |
| acggcacagc | gtggacatac | cattcccaga | atgagctggg | tggctcctcc | cactggggca | 780 |
| ggctcacaag | ctacagcggg | ggtggctact | acttggatct | tccaggatcc | cgacaagcca | 840 |
| gtgcagaggc | cctccaagga | ctccaggagg | gactgtggct | ggacaggggc | actcgggtgg | 900 |
| tctttatcga | cttctccgtc | tacaatgcca | acatcaatct | tttctgtatt | ctgagactgg | 960 |
| tggtagagtt | tccagccaca | ggagggacca | tcccatcctg | gcagatccgc | acagttaagc | 1020 |
| tgatccgcta | tgtgaataac | tgggacttct | tcattgtggg | ctgtgaagtt | gtcttctgtg | 1080 |
| tcttcatctt | ctattatgtg | gtggaggaaa | tcctggaaat | ccacctgcat | cggcttcgct | 1140 |
| acctcagcag | cgtctggaac | attctggacc | tggtggtcat | cttgctctcc | atcgtggctg | 1200 |
| tgggttttca | catattccga | accctggaag | tgaaccgact | gatgggaaag | cttctgcaac | 1260 |
| agccagacac | gtatgcagac | tttgagttcc | tggccttctg | gcagactcag | gacaataaca | 1320 |
| tgaacgcggt | caacctttc | tttgcttgga | tcaagatatt | caagtatatc | agcttcaaca | 1380 |
| agaccatgac | acagctctcc | tccaccctgg | ctcgatgtgc | caaggacatc | ctgggcttcg | 1440 |
| cagtcatgtt | cttcattgtc | ttcttcgctt | acgcccagct | tggttacctg | cttttttggga | 1500 |
| cccaagtgga | aaactttagc | actttcgtca | agtgcatttt | cactcagttc | cggataatcc | 1560 |
| ttggggattt | tgactacaat | gccatcgaca | atgccaacag | aatcctgggc | cctgtgtact | 1620 |
| ttgtcaccta | tgtcttcttc | gtcttcttcg | tgctcctgaa | catgttcctg | gccatcatca | 1680 |
| acgacacata | ctccgaggtc | aaggaggagc | tggctggcca | gaaggatcag | ttgcagcttt | 1740 |
| ctgacttcct | gaaacagagc | tacaacaaga | cctactaag | gctgcgcctg | aggaaagagc | 1800 |
| gggtttctga | tgtgcagaag | gtcctgaagg | gtgggaacc | agagatccag | tttgaagatt | 1860 |
| tcaccagcac | cttgagggaa | ctggggcacg | aggagcacga | gatcaccgct | gccttccacc | 1920 |
| ggtttgatca | ggatggggac | cacatactgg | atgaggagga | gcaggaacag | atgcggcagg | 1980 |
| gactggaaga | ggagagggtg | accctcaatg | ctgagattga | gaacctaggc | cggtctgttg | 2040 |
| gacacagccc | cccaggcgaa | ttgggcgcgg | aggctgccag | aggacaaagc | tgggtttctg | 2100 |

```
gagaagaatt cgacatgctc acaaggagag ttctgcagct gcagtgtgtt ctggaaggag    2160
ttgtgtccca gattgatgct gtaggctcaa agctgaagat gctggagagg aaggggagc    2220 tggctccctc cccaggaatg ggggaaccag ctgtttggga gaacctgtat aatccgtcct    2280
agt                                                                 2283

<210> SEQ ID NO 4
<211> LENGTH: 2418
<212> TYPE: DNA
<213> ORGANISM: Homo sapiens

<400> SEQUENCE: 4
atgaatgctg tgggaagtcc tgaggggcag gagctgcaaa agctggggag tggagcctgg     60
gacaaccccg cctacagtgg tccccttcc ccacacggga cgctgagagt ctgcaccatc    120
tccagcacgg ggcctctcca gcccaaccc aagaagcctg aagatgaacc ccaggagacg    180
gcatacagga cccaggtgtc cagctgctgc ctccatatct gtcaaggcat cagaggactt    240
tggggaacaa ccctgactga aacacagct gagaaccggg aactttatat caagaccacc    300
ctgagggagc tgttggtata tattgtgttc ctggtggaca tctgtctact gacctatgga    360
atgacaagct ccagtgctta ttactacacc aaagtgatgt ctgagctctt cttacatact    420
ccatcagaca ctggagtctc ctttcaggcc atcagcagca tggcggactt ctgggatttt    480
gcccagggcc cactactgga cagtttgtat tggaccaaat ggtacaacaa ccagagcctg    540
ggccatggct cccactcctt catctactat gaaacatgc tgctggggt tccgaggctg    600 cggcagctaa aggtccgcaa tgactcctgt gtggtgcatg aagacttccg ggaggacatt    660
ctgagctgct atgatgtcta ctctccagac aaagaagaac aactccccctt tgggcccttc    720 aatggcacag cgtggacata ccactcgcag gatgagttgg ggggcttctc ccactggggc    780
aggctcacaa gctacagcgg aggtggctac tacctggacc ttccaggatc ccgacagggt    840
agtgcagagg ctctccgggc ccttcaggag gggctgtggc tggacagggg cactcgagtg    900
gtgttcatcg acttctcagt ctacaatgcc aatatcaatc ttttctgtgt cctgaggctg    960
gtggtggagt ttccagctac aggaggtgcc atcccatcct ggcaaatccg cacagtcaag   1020
ctgatccgct atgtcagcaa ctgggactc tttatcgttg ctgtgaggt catcttctgc    1080 gtcttcatct tctactatgt ggtggaagag atcctggagc tccacattca ccggcttcgc    1140
tacctcagca gcatctggaa catactggac ctggtggtca tcttgctctc cattgtggct    1200
gtgggcttcc acatattccg aaccctcgag gtgaatcggc tcatggggaa gctcctgcag    1260
cagccaaaca cgtatgcaga cttttgagttc ctcgccttct ggcagacaca gtacaacaac    1320
atgaatgctg tcaacctctt cttcgcctgg atcaagatat caagtacat cagcttcaac    1380 aaaaccatga cccagctctc ctccacgctg cccgctgtg ccaaggacat cctgggcttc    1440
gccgtcatgt tcttcattgt tttcttcgcc tatgcccaac tcggctacct gcttttcggg    1500
acccaagtgg aaaactttag cactttcatc aagtgcattt tcactcagtt ccggataatc    1560 ctcgggact ttgactacaa tgctatcgac aatgccaacc gcatcctggg ccctgcctac    1620
tttgtcacct atgtcttctt cgtcttcttc gtgctcctga acatgttcct ggccatcatc    1680
aatgacacat attcagaggt caaggaggag ctggctggaca gaaggatga gctgcaactt    1740 tctgacctcc tgaaacaggg ctacaacaag accctactaa gactgcgtct gaggaaggag    1800
agggtttcgg atgtgcagaa ggtcctgcag ggtggggagc aggagatcca gtttgaggat    1860
```

-continued

```
ttcaccaaca ccttaaggga actgggacac gcagagcatg aaatcactga gctcacggcc    1920
accttcacca agtttgacag agatgggaat cgtattctgg atgagaagga acaggaaaaa    1980
atgcgacagg acctggagga agagagggtg gccctcaaca ctgagattga gaaactaggc    2040
cgatctattg tgagcagccc acaaggcaaa tcgggtccag aggctgccag agcaggaggc    2100
tgggtttcag gagaagaatt ctacatgctc acaaggagag ttctgcagct ggagactgtc    2160
ctggaaggag tagtgtccca gattgatgct gtaggctcaa agctgaaaat gctggagagg    2220
aaggggtggc tggctccctc cccaggcgtg aaggaacaag ctatttggaa gcacccgcag    2280
ccagccccag ctgtgacccc agaccccctgg ggagtccagg gtgggcagga gagtgaggtt    2340
ccctataaaa gagaagagga agccttagag gagaggagac tctcccgtgg tgagattcca    2400
acgttgcaga ggagttaa                                                  2418
```

<210> SEQ ID NO 5
<211> LENGTH: 795
<212> TYPE: PRT
<213> ORGANISM: Canis familiaris

<400> SEQUENCE: 5

```
Met Asn Ala Val Glu Ser Pro Glu Gly Gln Glu Leu Gln Lys Met Gly
1               5                   10                  15

Ser Gly Ala Trp Asp Asn Pro Ala Tyr Ser Gly Pro Ser Pro Arg
            20                  25                  30

Gly Thr Leu Lys Ile Cys Thr Ile Ser Ser Ala Met Pro Pro Gln Pro
        35                  40                  45

Gln Ile Gln Lys Pro Glu Asp Gly Pro Gln Glu Lys Ala Tyr Arg Thr
    50                  55                  60

Leu Val Ser Ser Cys Cys Phe Gln Ile Cys Arg Gly Ile Arg Gly Leu
65                  70                  75                  80

Trp Gly Thr Thr Leu Thr Glu Asn Thr Ala Glu Asn Arg Glu Leu Tyr
                85                  90                  95

Val Lys Thr Thr Leu Arg Glu Leu Leu Val Tyr Ile Val Phe Leu Val
            100                 105                 110

Asp Ile Cys Leu Leu Thr Tyr Gly Met Thr Ser Ser Ala Tyr Tyr
        115                 120                 125

Tyr Thr Lys Val Met Ser Glu Leu Phe Leu His Thr Pro Ser Asp Thr
    130                 135                 140

Gly Val Ser Phe Gln Ala Ile Ser Ser Met Ala Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly His Gly Ser His Ser Phe Ile Tyr Tyr Glu Asn
            180                 185                 190

Leu Leu Leu Gly Val Pro Arg Leu Arg Gln Leu Arg Val Arg Asn Asp
        195                 200                 205

Ser Cys Val Val His Glu Asp Phe Arg Glu Asp Ile Leu Ser Cys Tyr
    210                 215                 220

Asp Val Tyr Ser Pro Asp Lys Glu Glu Gln Leu Pro Phe Gly Pro Leu
225                 230                 235                 240

Asn Gly Thr Ala Trp Thr Tyr His Ser Gln Asp Glu Leu Gly Gly Ser
                245                 250                 255

Ser His Trp Gly Arg Leu Thr Ser Tyr Ser Gly Gly Gly Tyr Tyr Leu
            260                 265                 270
```

```
Asp Leu Pro Gly Ser Arg Gln Ala Ser Ala Glu Ala Leu Gln Asp Leu
            275                 280                 285

Gln Glu Gly Leu Trp Leu Asp Arg Gly Thr Arg Val Val Phe Ile Asp
290                 295                 300

Phe Ser Val Tyr Asn Ala Asn Ile Asn Leu Phe Cys Val Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Ser Asn Trp Asp Phe Phe Ile
            340                 345                 350

Ile Gly Cys Glu Ile Ile Phe Cys Ile Phe Ile Val Tyr Tyr Met Val
            355                 360                 365

Glu Glu Ile Leu Glu Leu His Ile His Arg Leu His Tyr Leu Ser Ser
370                 375                 380

Ile Trp Asn Ile Leu Asp Leu Val Val Ile Met Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asn Met Tyr Ala Asp Phe Glu Phe Leu Ala
            420                 425                 430

Phe Trp Gln Thr Gln Tyr Asn Asn Met Asn Ala Val Asn Leu Phe Phe
            435                 440                 445

Ala Trp Ile Lys Ile Phe Lys Tyr Ile Ser Phe Asn Lys Thr Met Thr
            450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Ile Lys Cys
            500                 505                 510

Ile Phe Thr Gln Phe Arg Ile Ile Leu Gly Asp Phe Asp Tyr Asn Ala
            515                 520                 525

Ile Asp Asn Ala Asn Arg Ile Leu Gly Pro Ala Tyr Phe Val Thr Tyr
530                 535                 540

Val Phe Phe Val Phe Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575

Glu Leu Gln Leu Ser Asp Leu Leu Lys Gln Gly Tyr Asn Lys Thr Leu
            580                 585                 590

Leu Arg Leu Arg Leu Arg Lys Glu Arg Val Ser Asp Val Gln Lys Val
            595                 600                 605

Leu Gln Gly Gly Glu Gln Glu Ile Gln Phe Glu Asp Phe Thr Asn Thr
610                 615                 620

Leu Arg Glu Leu Gly His Ala Glu His Glu Ile Thr Glu Leu Thr Ala
625                 630                 635                 640

Ala Phe Thr Arg Phe Asp Gln Asp Gly Asn His Ile Leu Asp Lys Lys
                645                 650                 655

Glu Gln Glu Gln Met Gln Gln Asp Leu Glu Glu Lys Arg Val Val Leu
            660                 665                 670

Asn Ala Glu Ile Glu Asn Leu Gly Gln Ser Ile Val Ser Ser Ser Pro
            675                 680                 685

Gly Glu Ser Gly Pro Glu Ala Thr Arg Ala Asp Gly Trp Val Ser Gly
```

```
                 690                 695                 700
Glu Glu Phe Tyr Thr Leu Thr Arg Arg Val Leu Gln Leu Glu Thr Val
705                 710                 715                 720

Leu Glu Gly Val Met Ser Gln Val Asp Ala Val Gly Ser Lys Leu Glu
            725                 730                 735

Met Leu Glu Arg Lys Glu Gln Leu Ala Ser Ser Pro Gly Met Gly Asp
        740                 745                 750

Gln Gly Ile Trp Glu His Leu Gln Pro Thr Ser Pro Val Thr Pro Asp
    755                 760                 765

Pro Trp Gly Val Gln Gly Gln Glu Ser Glu Phe Pro Gly Gly Arg
770                 775                 780

Glu Gly Glu Ala Leu Glu Glu Met Arg Leu Ser
785                 790                 795

<210> SEQ ID NO 6
<211> LENGTH: 212
<212> TYPE: DNA
<213> ORGANISM: Mus musculus

<400> SEQUENCE: 6
tccacaagca aatgaagtcg cctccccaac atcaggagga cagagagaac tatggggctg      60
gctgggtccc ccctgacaca aacatcacaa aagtagacag tatttggcat atcagaatc     120 aggagtcgct gggaggctat cccatccaag gggagctagc cacttactca ggaggaggct    180
atgttgtgag gcttggaaga aaccacaggg cg                                  212

<210> SEQ ID NO 7
<211> LENGTH: 655
<212> TYPE: DNA
<213> ORGANISM: Mus musculus

<400> SEQUENCE: 7
ggaaaaggaa cctcctggac acaagcatcg tcctcattag cttcagcatc ctgggcctca      60
gcatgcagag cctctctcta cttcacaaaa agatgcagca gtaccactgt gaccgggaca     120
ggttcatcag tttctacgag gcactgagag tgaactctgc agtcacccac ctcagggggct    180 tcctgcttct cttcgcaact gtgcgggtct gggacctact cgacatcat gcccagttac     240 aggtcatcaa caagacactg tccaaagcct gggacgaggt gctgggcttt atactgatca     300
tcgtggtcct gttaagcagc tatgccatga ctttcaacct gctgtttgga tggagcatct     360
ctgactacca gagcttcttc agatctatag tgactgttgt tggcctcttg atgggaactt     420
caaagcacaa ggaggttatt gctctatacc caatcctggg ctccttttg gttctcagta     480 gcatcatctt gatgggactt gtgatcatta atcttttgt ttctgccatt ctcattgcct     540
ttgggaaaga aaggaaggcc tgtgagaaag aagctacact gacagatatg ttactacaaa     600
agctctcaag tctgttagga atccgcctgc accagaatcc atctgaggaa cacgc          655

<210> SEQ ID NO 8
<211> LENGTH: 70
<212> TYPE: PRT
<213> ORGANISM: Mus musculus

<400> SEQUENCE: 8

His Lys Gln Met Lys Ser Pro Pro Gln His Gln Glu Asp Arg Glu Asn
1               5                   10                  15

Tyr Gly Ala Gly Trp Val Pro Pro Asp Thr Asn Ile Thr Lys Val Asp
            20                  25                  30
```

```
Ser Ile Trp His Tyr Gln Asn Gln Glu Ser Leu Gly Gly Tyr Pro Ile
         35                  40                  45

Gln Gly Glu Leu Ala Thr Tyr Ser Gly Gly Gly Tyr Val Val Arg Leu
 50                  55                  60

Gly Arg Asn His Arg Ala
 65                  70

<210> SEQ ID NO 9
<211> LENGTH: 217
<212> TYPE: PRT
<213> ORGANISM: Mus musculus

<400> SEQUENCE: 9

Lys Arg Asn Leu Leu Asp Thr Ser Ile Val Leu Ile Ser Phe Ser Ile
  1               5                  10                  15

Leu Gly Leu Ser Met Gln Ser Leu Ser Leu Leu His Lys Lys Met Gln
             20                  25                  30

Gln Tyr His Cys Asp Arg Asp Arg Phe Ile Ser Phe Tyr Glu Ala Leu
         35                  40                  45

Arg Val Asn Ser Ala Val Thr His Leu Arg Gly Phe Leu Leu Leu Phe
 50                  55                  60

Ala Thr Val Arg Val Trp Asp Leu Leu Arg His His Ala Gln Leu Gln
 65                  70                  75                  80

Val Ile Asn Lys Thr Leu Ser Lys Ala Trp Asp Val Leu Gly Phe
                 85                  90                  95

Ile Leu Ile Ile Val Val Leu Ser Ser Tyr Ala Met Thr Phe Asn
                100                 105                 110

Leu Leu Phe Gly Trp Ser Ile Ser Asp Tyr Gln Ser Phe Phe Arg Ser
            115                 120                 125

Ile Val Thr Val Val Gly Leu Leu Met Gly Thr Ser Lys His Lys Glu
        130                 135                 140

Val Ile Ala Leu Tyr Pro Ile Leu Gly Ser Leu Val Leu Ser Ser
145                 150                 155                 160

Ile Ile Leu Met Gly Leu Val Ile Ile Asn Leu Phe Val Ser Ala Ile
                165                 170                 175

Leu Ile Ala Phe Gly Lys Glu Arg Lys Ala Cys Glu Lys Glu Ala Thr
            180                 185                 190

Leu Thr Asp Met Leu Leu Gln Lys Leu Ser Ser Leu Leu Gly Ile Arg
        195                 200                 205

Leu His Gln Asn Pro Ser Glu Glu His
    210                 215

<210> SEQ ID NO 10
<211> LENGTH: 6456
<212> TYPE: DNA
<213> ORGANISM: Mus musculus

<400> SEQUENCE: 10
atgctcttgc agaggcggtc ctggctctgg ctgtacatta gaatcggtgt cattctgggt      60
gatattttgg acgtaaaacc aagcatccgg agcaacatg ggggaaacag ctgctatcag     120
cttaacagac tttttctgtga cttccaggaa gcagataact actgccacgc cagagagga    180 cgcctagccc acacgtggaa ccccaagctt cggggtttcc taaaaagctt cctgaatgaa    240
gaaacagtgt ggtgggtcag ggaaaacctg acgctgcccg atcgcatcc agggataaat    300 cagacaggag gtgatgacgt cttaaggaac caaaagcctg gcgagtgccc ttccgtggtc    360
```

-continued

```
acacactcta atgctgtctt ctcaagatgg aacctgtgca tagagaagca tcatttcatt      420
tgccaggctg ccgcctttcc ccctcaaggt gcaagcattt ggagaaatga gtttggtcct      480
ggtcctctgt tacccatgaa aagaagagga gctgagacag agagacatat gatcccagga      540
aatggccccc cgttagccat gtgtcaccaa cccgctcctc ctgagctttt tgagacattg      600
tgctttccca ttgacccagc ttcttcagca cctccaaaag ccacacacag gatgacaatc      660
acatccctaa ctggaaggcc acaggtgaca tcagacacac ttgcatccag cagcccacca      720
caggggacat cagacacacc tgcatccagc agcccaccac aggtgacatc agccacatct      780
gcatctagca gcccaccaca ggggacatca gacacacctg catccagcag cccaccacag      840
gtgacatcag ccacatctgc atctagcagc ccaccacagg ggacatcaga cacacctgca      900
tccagcagcc caccacaggt gacatcagcc acatctgcat ctagcagccc accacagggg      960
acatcagaca cacctgcatc cagcagccca ccacaggtga catcagccac atctgcatct     1020
agcagcccac cacaggggac atcagacaca cctgcatcca gcagcccacc acaggggaca     1080
ttagacacac cttcatctag cagcccacca caggggacat cagacacacc tgcatccagc     1140
agcccaccac aggggacatc agagacacct gcatccaaca gcccaccaca ggggacatca     1200
gagacacctg gattcagcag cccaccacag gtgacaacag ccacacttgt atccagcagc     1260
ccaccacagg tgacatcaga gacacctgca tccagcagcc caacacaggt gacatcagag     1320
acacctgcat ccagcagccc aacacaggtg acatcagaca cacctgcatc caatagccca     1380
ccacagggga catcagacac acctggattc agcagcccaa cacaggtgac aacagccaca     1440
cttgtatcca gcagcccacc acaggtgaca tcagacacac ctgcatccag cagcccacca     1500
caggtgacat cagacacacc tgcatccagc agcccaccac aggtgacatc agagacacct     1560
gcatccagca gcccaccaca ggtgacatca gacacatctg catccatcag cccaccacag     1620
gtaatatcag acacacctgc atccagcagc ccaccacagg tgacatcaga gacacctgca     1680
tccagcagcc caacaaacat gacatcagac acacctgcat ccagcagccc aacaaacatg     1740
acatcagaca cacctgcatc cagcagccca acaaacatga catcagacac acctgcatcc     1800
agcagcccac catggcctgt tataacagag gtcaccaggc ctgaatccac aatacctgct     1860
ggaagatctt tggcaaacat cacttcaaag gcacaggaag actctcccct gggagtcatc     1920
tctacccatc cacagatgtc atttcagagt tcaaccagtc aggccttgga tgagacagca     1980
ggggaacggg tccaacaat tcctgatttc caagcccaca gtgaattcca gaaagcttgt      2040
gccatcctcc agagactgag agacttcctg ccgacttctc ccacatcagc tcaggtcagt     2100
gtggccaatt tactcattga cctgagtgag cagttgctgg tgctcccgtt tcagaagaac     2160
aacagttgga gctctcaaac tccagcagtc agctgcccct tccagcctct tggacgtcta     2220
acaacaacgg aaaaaagcag tcatcagatg gctcagcaag acatggaaca ggttgaagac     2280
atgctggaga catccctgat ggccctgggg gagatccaca gagcattttg ccagcagagt     2340
ctgtgccctc agtcagcagt gaccctggcc tctccctctg ctactctgat gttgagcagc     2400
caaaatgtgt caacgttgcc cctgagcacc tacactttgg gtgagcctgc acccttgact     2460
ttgggcttcc cgtcagcaga agctctgaag gagctcttga acaaacaccc aggcgtgaac     2520
cttcaagtga caggtctggc tttcaaccct tttaagactt tggatgacaa gaacattgtt     2580
ggaagcattg gaaatgtgca gctgagctct gcttatcagt cgatcagagt ccacgactta     2640
atagaagata ttgagatcat gctctggaga aatgccagca tggagaccca gcccaccagc     2700
```

```
ctcaacacaa gtacagacca tttcacaatc tctgtgaaca tcacttcctt ggagaagacc   2760
ctcattgtga ccatcgagcc tgaaagtccc ctcctaatga cgctccactt gggcttccag   2820
gaccagctgg cccacactca cttctatctc aacatcagcc tgccaaggga ccaagtgtgg   2880
cagaaagatg aggagtacac gtgggtgctg acaccagaga acctgtggta cgggactggc   2940
acctactaca taatggctgt ggagaataaa agtacagagg cggcacagca cacacccgtc   3000
ctggtctcag tggtcacagc tgtcacccag tgctatttct gggaccgata caataggaca   3060
tggaagagcg atggatgcca agtggggccg aagagcacca ttttaaagac acagtgtctc   3120
tgtgaccacc tgaccttctt cagcagcgac ttcttcatcg tgccgaggac ggtggatgta   3180
gaaaacacca tcaaactgct tcttcatgtg accaacaacc ctgtcggggt gtcattgctg   3240
tccagcctcc taggattcta tatcctctta gccatgtggg cttccagaaa ggatcgagaa   3300
gatatgcaga aggtgaaggt aacagtcctg gctgacaatg accccagctc tgcatcccac   3360
taccttatcc aggtctacac tggctatcgg aggagggctg ctaccaccgc caaggtcgtt   3420
atcactctct atggctcaga ggggcacagt gagccccacc acctttgtga ccctgagaag   3480 acagttttg agcgtggagc actggatgtt ttccttcttt ccaccggatc ctggctgggg   3540
gacctgcatg gccttcggct gtggcatgac aattctggcg acagcccttc ttggtatgta   3600
agccaggtga tcgtcagtga catgaccacg aggaagaaat ggcatttcca gtgcaattgt   3660
tggctggccg tggacttggg caactgtgag cgtgacaggg tgttcacacc agcctccaga   3720
agcgagctct cttccttcag cacctgttc tcctccacaa tcgtagaaaa gttcacccag   3780
gattatctgt ggctctcagt tgcaactcga catccctgga accagtttac acgagtccag   3840
aggctctcct gctgcatggc actactgctc tgtgacatgg tcatcaatat tatgttctgg   3900
aagatgggtg gcaccactgc caagaggggc accgaacaac taggtccact tgctgtgacc   3960
ttgtcggagc tgctcgtcag catccagacc tccatcatcc tcttccccat ccacctcatc   4020
tttgggcggc tcttccagtt gattcaccca ccagaagctc tgccccagct tcctttcatc   4080
caggctgcct ggcccctgc tcttgtttgt gagtcccct ctcttacaca ggtggtcaag   4140
gaattaaagg aaactgtggg attcctgctc aggagaaata cacagctgct ctcggagtgt   4200
gagccgtctt cgtgcagttc ttgtgacatt aacaagctgg cgaagctttt atccggcctc   4260
atttactgtc acttagaaga cgaaggctgt caccagcaga cagaatccca ctgggaagac   4320
gcagtgtctg aaaaccatta ccatttctgc cgctaccttc tccaacttct gcggagactg   4380
aaagcgcatt tagaggctct tggtgctacc caggatcacc agtcttgtga tttctcagaa   4440
gcagtcagcc aacttcaaaa cctccaggaa ctcctggaga cacagactct ccgcagaggg   4500
ccagggccat gcaggcattc caccagtttc cccatcctca gccaggagaa agggaagaag   4560
cccatgtcat tttgcctgtt cagatggttg aagtgcagct gctggctcct tcttggtgtc   4620
atcagcctgg cctcggcctt ttttataacg ctctatagct tggagttgga caagaccaa   4680 gccaccagct gggttatttc aatgatgctg tcggtactac aagacatctt tatcagccag   4740
ccgataaagg tcatcttcct gacattgttg ttctccctga tggcaaacca catgccgtgg   4800
cttaacaaag acaaggaaca acacgcccgg agaatcgtag cactttgggc aaagtgtcct   4860
tggtcggcac ctggcttgag agacaagaac aatcccatct acactgcccc agcaatgaac   4920
aacctagcca agcctacaag gaaggcctgg aagaagcagc tctccaagct gacgggtggt   4980
actctggtgc aaatcctctt cctgaccctg ctgatgacta ccgtctattc tgcaaaggac   5040
tctagtcgat ttttcctcca tcgagctatc tggaagaggt tttctcaccg tttctcagaa   5100
```

| | |
|---|---|
| atcaaaactg tagaggattt ctacccctgg gccaacggca ccctccttcc taacctatat | 5160 |
| ggggattaca gaggatttat tactgacggg aactcctttc ttctgggcaa tgttttgatc | 5220 |
| cgccagactc gcattcctaa tgacatattc ttcccaggat ctctccacaa gcaaatgaag | 5280 |
| tcgcctcccc aacatcagga ggacagagag aactatgggg ctggctgggt ccccctgac | 5340 |
| acaaacatca caaagtaga cagtatttgg cattatcaga atcaggagtc gctgggaggc | 5400 |
| tatcccatcc aaggggagct agccacttac tcaggaggag gctatgttgt gaggcttgga | 5460 |
| agaaaccaca gtgcggcaac cagggttctg cagcatctgg aacagaggcg ctggctggac | 5520 |
| cactgcacaa aagccctctt tgtagaattc acggtcttca atgctaatgt gaatctgctc | 5580 |
| tgtgcggtga ccctcatctt ggaatccagt ggtgtgggga ctttcctcac ctccctgcaa | 5640 |
| ctggacagtt taacttccct tcagtcatca gagagggggct tcgcctggat cgtctcacag | 5700 |
| gtcgtctact accttctcgt ctgttactat gccttcatcc agggctgtcg gctgaagcgg | 5760 |
| cagaggctgg cgttcttcac taggaaaagg aacctcctgg acacaagcat cgtcctcatt | 5820 |
| agcttcagca tcctgggcct cagcatgcag agcctctctc tacttcacaa aaagatgcag | 5880 |
| cagtaccact gtgaccggga caggttcatc agtttctacg aggcactgag agtgaactct | 5940 |
| gcagtcaccc acctcagggg cttcctgctt ctcttcgcaa ctgtgcgggt ctgggaccta | 6000 |
| ctgcgacatc atgcccagtt acaggtcatc aacaagacac tgtccaaagc ctgggacgag | 6060 |
| gtgctgggct ttatactgat catcgtggtc ctgttaagca gctatgccat gactttcaac | 6120 |
| ctgctgtttg gatggagcat ctcctgactac cagagcttct tcagatctat agtgactgtt | 6180 |
| gttggcctct tgatgggaac ttcaaagcac aaggaggtta ttgctctata cccaatcctg | 6240 |
| ggctccctttt tggttctcag tagcatcatc ttgatggac ttgtgatcat taatcttttt | 6300 |
| gtttctgcca ttctcattgc ctttgggaaa gaaaggaagg cctgtgagaa agaagctaca | 6360 |
| ctgacagata tgttactaca aaagctctca agtctgttag gaatccgcct gcaccagaat | 6420 |
| ccatctgagg aacacgctga caacactggg tattga | 6456 |

<210> SEQ ID NO 11
<211> LENGTH: 5193
<212> TYPE: DNA
<213> ORGANISM: Homo sapiens

<400> SEQUENCE: 11

| | |
|---|---|
| atgttcttca aaggaggaag ctggctttgg ttatacatca gaacaagtat tattctagga | 60 |
| agtgagctaa acagcccagc accacatggg caaaataatt gttaccagct taacagattt | 120 |
| caatgcagct ttgaggaagc acagcattac tgtcatgtgc agagaggatt cctagctcat | 180 |
| atttggaaca aggaagttca agatctcatc cgggactatc tggaagaagg aaagaagtgg | 240 |
| tggattgggc aaaatgtaat gccattgaaa aagcatcaag acaacaaata cccagcagac | 300 |
| gttgcagcca acgggccccc aaagcccctc agctgcacct acctgtccag aaacttcatt | 360 |
| cggatctcat ccaaggggga caagtgctta ctgaaatact atttcatttg ccagactggt | 420 |
| gacttttttgg acggagatgc ccattatgaa agaaatggaa ataattccca tttgtaccag | 480 |
| agacacaaga agacaaaaag aggagttgca atagcaagag acaaaatgcc ccaggaccct | 540 |
| ggtcatcttc caaccacatg tcactatcct cttcctgctc atctttccaa gaccctgtgt | 600 |
| catcccatca gccagtttcc ttcagtacta tcaagtatca catcacaggt aacatcagcc | 660 |
| gcatctgaac ccagcagcca gcctctccct gtgataacac agctcaccat gcccgtgtct | 720 |

```
gtcacgcatg ctgggcaatc tctggcagaa acaacttcaa gcccaaagga agaaggtcat      780
ccgaatacct tcacctctta tctacaagtg tcattgcaga aggcatctgg tcaggtcata      840
gatgagatag cagggaactt cagcagagca gttcatggtt tgcaagctct taacaaacta      900
caggaagctt gtgagttcct ccagaaacta acagccttaa ccccaagatt ttctaagcca      960
gctcaggtta atctcatcaa ttcccttatt tacctgagtg aggagttact caggatccca     1020
tttcagaaca acaacagtct gggcttcaaa gttcctccaa ctgtctgccc ctttcattcc     1080
ctcaacaatg tcaccaaagc tggagaagga agttggctgg aatccaagcg tcatactgag     1140
ccggtagaag acatcctgga aatgtccttg gtggagtttg gaatatcgg ggaagcattt      1200 ctagagcaga accagtctcc cgagtcttca gtgactttga cctctgccaa tgctactctg     1260
ctgctgagca gacaaaacat atcaacttta ccgctgagct cttacactct gggtcaccca     1320
gcccctgtga ggctaggctt tccgtcggct ttagctttga aggagctctt gaataaacat     1380
ccaggagtta atgtccaaat aacaggacta gctttcaatc ccttcaagga tttggacaac     1440
agaaacattg ttggaagcat tggaagtgtg ttactaagcg ctaatcgtaa attgctccaa     1500
gtccatgatt taatggagga cattgagatc atgctctgga gaaatgttag cttggaaacc     1560
catcccacca gcctcaacat gagcacacat cagcttacaa tcacagtgaa cgtcacttcc     1620
ttggagaaat ccttgatagt gagcatagat cctgacagtc ccctttaat gacactctac      1680 ctggggttcc agtatcagcc taactgcact cacttccacc tgaacatcac ccttccaaag     1740
gataaggtgt ggcaaaaaga tgaggagtac acgtgggtgc tgaatccaga gcatctgcag     1800
cacgggattg gcacctacta tataacagct gtgctgagtg agaggcagga gggtgctcag     1860
cagacaccca gcttggtctc ggtcatcacc gccgtcactc agtgttacta ctgggagatc     1920
cacaaccaga catggagcag cgccggatgc caagttgggc cacagagcac aattctgagg     1980
acacagtgtc tctgtaacca cctgaccttc tttgccagcg acttctttgt cgtgcccagg     2040
accgtgaatg ttgaagacac gatcaaactg ttccttcgcg tgaccaacaa tcctgttggg     2100
gtgtcactgc tggccagcct tttaggattt tatgtgatca cagttgtgtg ggctcggaaa     2160
aaggatcaag cagatatgca gaaggtgaag gtcactgtcc tggctgataa tgaccccagc     2220
gctcaatttc actaccttat tcaggtctac accggatatc gaagaagcgc tgctacaaca     2280
gctaaggttg tcatcaccct ctatggatca gagggacgga gtgagcccca tcacctctgt     2340
gacccccaga agacagtctt tgaacgaggg ggcctggatg tcttccttct caccacttgg     2400
acctctctag ggaacctgca cagccttcgg ctctggcatg acaattctgg cgtcagtccc     2460
tcctggtatg tcagccaggt aattgtctgt gacatggcag ttaagaggaa gtggcatttc     2520
ctgtgcaatt gctggctggc tgtggacctc ggagactgtg agcttgaccg ggtcttcatc     2580
ccagtttcaa agagagagct ctttttccttt agacatctgt tttcctccat gattgtggaa     2640
aagttcaccc aggattatct gtggcttcca attgcaactc ggcatccctg gaaccagttt     2700
acaagggtcc aacggctgtc ttgctgcatg acactgctac tctgcaacat ggtcatcaat     2760
gttatgttct ggaagataaa cagcaccact gccaagagag atgagcaaat gcgtccattt     2820
gctgtggcct ggtctgaact gctggtcagc atccatactg ctgtcatcct cttcccaatc     2880
aatcttgtca tagggcggct cttcccgttg attgagccac aggagactct gccctctttt     2940
cctcccatcc aggcctcctg cctctcagat gcttctgttg agcctctctc tgccacaatg     3000
gtagttgagg aattaaagga aactgtgaga ttcctgctca ggagaaatac ataccactc      3060 tccaagtgtg agcagccgcc atggagttct tgggacatta ctaagctggt gaaacttta      3120
```

```
tccagcctcg tatcatctca cttggagggt caaggctgtc atcagcaggg agagcgccac    3180
tgggcacgtg ttgttcctga aaaccaccat catttctgct gttacctgca tagagttctg    3240
cagaggctga aatctcactt aggcacgctg gtctcaccc agggtcacca gtcctgtgac     3300
ttcctagatg cagccagcca acttcaaaaa ctccaggaac tcttggaaac acatattctt    3360
cccacggagc aagagccatc cagggaagtc accagttttg ccatcctgag ctcagaagaa    3420
ggaaaaaagc ccatctcaaa tggcctgtcc aaatggttga cttcagtctg ctggctcctc    3480
ttaggtttca ctagcctggc ttcagccttt tttacagcac tttatagctt ggaattgagc    3540
aaagaccaag ccaccagctg gatgatttca attattttat cagtgcttca gaacatcttc    3600
atcagccagc cagtaaaggt ggtcttcttc acattcttat actcactgat gatgagcagg    3660
atgccacggc ttaacaaaga gaatgaacaa caaaggatct tggcactctt ggcaaaatgt    3720
tcttcgtcag taccaggttc aagagataag aacaaccccg tctatgtagc cccagctata    3780
aatagtccaa ctaagcaccc agaaagaacc ttgaaaaaga agaaactctt caagctgact    3840
ggagatattt tggtacaaat cctcttcctt accctgttga tgactgcaat ctactctgca    3900
aagaactcca atagatttta cctccaccaa gctatctgga agacattttc gcaccagttc    3960
tcggaaatca aacttcttca ggatttctac ccctgggcca atcatatcct tcttcctagc    4020
ctgtatgggg attacagagg taagaatgca gtcctggagc ccagtcattg caaatgtggg    4080
gtacaattaa ttttccaaat accccgtacc aagacctatg agaaagtgga cgaaggtcag    4140
ctggcgtttt gtgataacgg ccatacctgt gggcgtccca agagcctatt ccctggactt    4200
catctaagga ggttcagtta catctgttca cccaggccca tggtgctgat tcccactgat    4260
gagcttcacg aaaggctgac aagcaagaat gagaatggat tcagttacat catgagaggt    4320
gctttcttca cctctttgag actggaaagc ttcacttccc ttcagatgtc aaagaagggc    4380
tgtgtctggt ctatcatctc acaagtcatc tattatctac tggtctgtta ctatgccttc    4440
atacagggtt gtcagctgaa acagcagaag tggaggttct tcactgggaa aagaaacatt    4500
ctggacacaa gtataatcct cattagcttc atcctcctgg ggcttgacat gaagagtatt    4560
tctctacata agaaaaacat ggcacgatac cgcgatgacc aggacagatt catcagcttc    4620
tatgaggcag taaagtgaa ctctgctgcg actcacttg tgggcttccc ggttctcctg    4680
gcaactgttc agttatggaa cctgctgcgt catagcccca ggctgcgggt catcagcagg    4740
acactgagcc gagcctggga cgaggtggtg ggctttctgc tgatcatcct aatcctgctg    4800
acaggctatg ccattgcctt taacctgctg tttggatgca gcatctctga ctaccggaca    4860
tttttcagct cagcagtgac tgttgttggt ctcctgatgg gaatttctca ccaagaggag    4920
gttttcgctt tagacccagt cctgggcacc tttctgatcc tcaccagtgt catcttgatg    4980
gtacttgtgg taattaatct tttcgtttcg gccattctca tggcctttgg aaaagaaaga    5040
aagtcgctta agaaagaagc tgcactaata gatacactgc tacagaagct ctcaaatttg    5100
ttaggaatca gttggcccca aaaaacctca tctgagcaag cagccacgac agcagtgggc    5160
agtgacactg aagtttttaga tgaactacct taa                                5193
```

<210> SEQ ID NO 12
<211> LENGTH: 763
<212> TYPE: PRT
<213> ORGANISM: Rattus norvegicus

<400> SEQUENCE: 12

-continued

```
Met Asn Ile Met Glu Asn Ser Lys Glu Gln Glu Leu Gln Thr Leu Gly
 1               5                  10                  15

Ser Arg Val Trp Asp Asn Pro Ala Tyr Ser Ser Pro Ser Pro Asn
             20                  25                  30

Gly Thr Pro Arg Ile Cys Thr Val Ser Ser Val Ala Leu Pro Glu Thr
                 35                  40                  45

Gln Pro Lys Lys Pro Glu Val Arg Arg Gln Lys Thr Pro Arg Val
 50                  55                          60

Pro Val Ser Gly Cys Cys Leu Leu Ile Cys Arg Ser Ile Arg Gly Leu
 65                      70                  75                  80

Trp Gly Thr Thr Leu Thr Glu Asn Thr Ala Glu Asn Arg Glu Leu Tyr
                     85                  90                  95

Val Lys Thr Thr Leu Arg Glu Leu Val Val Tyr Ile Val Phe Leu Val
                100                 105                 110

Asp Val Cys Leu Leu Thr Tyr Gly Met Thr Ser Ser Ala Tyr Tyr
                115                 120                 125

Tyr Thr Lys Val Met Ser Glu Leu Phe Leu His Thr Pro Ser Glu Ser
                130                 135                 140

Ala Val Ser Phe Gln Thr Ile Ser Ser Met Ser Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly Ser Ser His Ser Phe Ile Tyr Tyr Glu Asn
                180                 185                 190

Leu Leu Leu Gly Val Pro Arg Leu Arg Gln Leu Arg Val Arg Asn Asp
                195                 200                 205

Ser Cys Val Val His Glu Asp Phe Arg Glu Asp Ile Leu Asn Cys Tyr
210                 215                 220

Asp Val Tyr Ser Pro Asp Lys Glu Asp Gln Leu Pro Phe Gly Pro Leu
225                 230                 235                 240

Asn Gly Thr Ala Trp Thr Tyr His Ser Gln Asn Glu Leu Gly Gly Ser
                245                 250                 255

Ser His Trp Gly Arg Leu Thr Ser Tyr Ser Gly Gly Tyr Tyr Leu
                260                 265                 270

Asp Leu Pro Gly Ser Arg Gln Ala Ser Ala Glu Ala Leu Gln Gly Leu
                275                 280                 285

Gln Glu Gly Leu Trp Leu Asp Arg Gly Thr Arg Val Val Phe Ile Asp
290                 295                 300

Phe Ser Val Tyr Asn Ala Asn Ile Asn Leu Phe Cys Ile Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Asn Asn Trp Asp Phe Phe Ile
                340                 345                 350

Val Gly Cys Glu Val Ile Phe Cys Ile Phe Ile Phe Tyr Tyr Val Val
                355                 360                 365

Glu Glu Ile Leu Glu Ile Arg Val His Arg Phe Arg Tyr Leu Ser Ser
                370                 375                 380

Val Trp Asn Ile Leu Asp Leu Val Val Ile Leu Leu Ser Ile Val Ala
385                 390                 395                 400

Val Gly Phe His Val Phe Arg Thr Leu Glu Val Asn Arg Leu Met Gly
                405                 410                 415

Glu Leu Leu Gln Gln Pro Asp Thr Tyr Pro Asp Phe Glu Phe Leu Ala
```

```
                420             425             430
Phe Trp Gln Thr Gln Tyr Asn Asn Met Asn Ala Val Asn Leu Phe Phe
            435                 440                 445
Ala Trp Ile Lys Ile Phe Lys Tyr Ile Ser Phe Asn Lys Thr Met Thr
450                 455                 460
Gln Leu Ser Ser Thr Leu Ala Arg Cys Ala Lys Asp Ile Leu Gly Phe
465                 470                 475                 480
Ala Ile Met Phe Phe Ile Val Phe Phe Ala Tyr Ala Gln Leu Gly Tyr
                485                 490                 495
Leu Leu Phe Gly Thr Gln Val Glu Ser Phe Ser Thr Phe Val Lys Cys
            500                 505                 510
Ile Phe Thr Gln Phe Arg Ile Ile Leu Gly Asp Phe Asp Tyr Asn Ala
            515                 520                 525
Ile Asp Asn Ala Asn Arg Ile Leu Gly Pro Val Tyr Phe Ile Thr Tyr
            530                 535                 540
Val Phe Phe Val Phe Val Leu Leu Asn Met Phe Leu Ala Ile Ile
545                 550                 555                 560
Asn Asp Thr Tyr Ser Glu Val Lys Glu Leu Ala Gly Gln Arg Asp
                565                 570                 575
Gln Leu Gln Leu Ser Asp Leu Leu Lys Gln Ser Tyr Ser Lys Thr Leu
            580                 585                 590
Gln Arg Leu Arg Leu Arg Lys Glu Arg Val Ser Asp Val Gln Lys Val
            595                 600                 605
Leu Lys Gly Gly Glu Pro Glu Ile Gln Phe Glu Asp Phe Thr Asn Thr
610                 615                 620
Leu Arg Glu Leu Gly His Ala Glu Arg Glu Ile Ser Glu Val Ser Ala
625                 630                 635                 640
Ala Phe Thr Arg Phe Asp Arg Asp Gly Asp His Ile Leu Asp Glu Glu
                645                 650                 655
Asp Gln Ala Gln Met Arg Gln Gly Leu Glu Glu Arg Met Thr Leu
                660                 665                 670
Ser Ala Glu Thr Glu Asn Leu Gly Arg Ser Val Gly His Ser Pro Pro
            675                 680                 685
Gly Glu Leu Asp Ala Glu Ala Ala Arg Gly Arg Ser Trp Val Ser Gly
            690                 695                 700
Glu Glu Phe Asp Met Leu Thr Arg Arg Val Leu Gln Leu Gln Arg Val
705                 710                 715                 720
Leu Glu Gly Val Val Ser Gln Val Asp Ala Leu Ser Ser Lys Leu Lys
                725                 730                 735
Met Leu Glu Arg Lys Gly Glu Leu Ala Pro Ser Pro Gly Met Ala Met
            740                 745                 750
Pro Ala Val Trp Glu Asn Pro Tyr Asn Pro Ser
            755                 760

<210> SEQ ID NO 13
<211> LENGTH: 760
<212> TYPE: PRT
<213> ORGANISM: Mus musculus

<400> SEQUENCE: 13

Met Asn Ser Met Glu Ser Pro Lys Asn Gln Glu Leu Gln Thr Leu Gly
1               5                   10                  15

Asn Arg Ala Trp Asp Asn Pro Ala Tyr Ser Asp Pro Pro Ser Pro Asn
            20                  25                  30
```

-continued

```
Arg Thr Leu Arg Ile Cys Thr Val Ser Ser Val Ala Leu Pro Glu Thr
            35                  40                  45

Gln Pro Lys Lys Pro Glu Val Arg Cys Gln Glu Lys Thr Gln Arg Thr
        50                  55                  60

Leu Val Ser Ser Cys Cys Leu His Ile Cys Arg Ser Ile Arg Gly Leu
65                  70                  75                  80

Trp Gly Thr Thr Leu Thr Glu Asn Thr Ala Glu Asn Arg Glu Leu Tyr
                85                  90                  95

Val Lys Thr Thr Leu Arg Glu Leu Val Val Tyr Ile Val Phe Leu Val
            100                 105                 110

Asp Val Cys Leu Leu Thr Tyr Gly Met Thr Ser Ser Ala Tyr Tyr
        115                 120                 125

Tyr Thr Lys Val Met Ser Glu Leu Phe Leu His Thr Pro Ser Asp Ser
        130                 135                 140

Gly Val Ser Phe Gln Thr Ile Ser Ser Met Ser Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly Arg Gly Ser His Ser Phe Ile Tyr Tyr Glu Asn
            180                 185                 190

Leu Leu Leu Gly Ala Pro Arg Leu Arg His Val Arg Val Arg Asn Asp
        195                 200                 205

Ser Cys Val Val His Glu Asp Phe Arg Glu Asp Ile Leu Asn Cys Tyr
        210                 215                 220

Asp Val Tyr Ser Pro Asp Lys Glu Asp Gln Leu Pro Phe Gly Pro Gln
225                 230                 235                 240

Asn Gly Thr Ala Trp Thr Tyr His Ser Gln Asn Glu Leu Gly Gly Ser
                245                 250                 255

Ser His Trp Gly Arg Leu Thr Ser Tyr Ser Gly Gly Tyr Tyr Leu
            260                 265                 270

Asp Leu Pro Gly Ser Arg Gln Ala Ser Ala Glu Ala Leu Gln Gly Leu
        275                 280                 285

Gln Glu Gly Leu Trp Leu Asp Arg Gly Thr Arg Val Val Phe Ile Asp
        290                 295                 300

Phe Ser Val Tyr Asn Ala Asn Ile Asn Leu Phe Cys Ile Leu Arg Leu
305                 310                 315                 320

Val Val Glu Phe Pro Ala Thr Gly Gly Thr Ile Pro Ser Trp Gln Ile
                325                 330                 335

Arg Thr Val Lys Leu Ile Arg Tyr Val Asn Asn Trp Asp Phe Phe Ile
            340                 345                 350

Val Gly Cys Glu Val Val Phe Cys Val Phe Ile Phe Tyr Tyr Val Val
        355                 360                 365

Glu Glu Ile Leu Glu Ile His Leu His Arg Leu Arg Tyr Leu Ser Ser
        370                 375                 380

Val Trp Asn Ile Leu Asp Leu Val Val Ile Leu Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asp Thr Tyr Ala Asp Phe Glu Phe Leu Ala
            420                 425                 430

Phe Trp Gln Thr Gln Asp Asn Asn Met Asn Ala Val Asn Leu Phe Phe
        435                 440                 445

Ala Trp Ile Lys Ile Phe Lys Tyr Ile Ser Phe Asn Lys Thr Met Thr
```

```
                450                 455                 460
Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Val Lys Cys
                500                 505                 510

Ile Phe Thr Gln Phe Arg Ile Ile Leu Gly Asp Phe Asp Tyr Asn Ala
                515                 520                 525

Ile Asp Asn Ala Asn Arg Ile Leu Gly Pro Val Tyr Phe Val Thr Tyr
530                 535                 540

Val Phe Phe Val Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575

Gln Leu Gln Leu Ser Asp Phe Leu Lys Gln Ser Tyr Asn Lys Thr Leu
                580                 585                 590

Leu Arg Leu Arg Leu Arg Lys Glu Arg Val Ser Asp Val Gln Lys Val
                595                 600                 605

Leu Lys Gly Gly Glu Pro Glu Ile Gln Phe Glu Asp Phe Thr Ser Thr
610                 615                 620

Leu Arg Glu Leu Gly His Glu Glu His Glu Ile Thr Ala Ala Phe Thr
625                 630                 635                 640

Arg Phe Asp Gln Asp Gly Asp His Ile Leu Asp Glu Glu Glu Gln Glu
                645                 650                 655

Gln Met Arg Gln Gly Leu Glu Glu Arg Val Thr Leu Asn Ala Glu
                660                 665                 670

Ile Glu Asn Leu Gly Arg Ser Val His Ser Pro Pro Gly Glu Leu
                675                 680                 685

Gly Ala Glu Ala Ala Arg Gly Gln Ser Trp Val Ser Gly Glu Glu Phe
690                 695                 700

Asp Met Leu Thr Arg Arg Val Leu Gln Leu Gln Cys Val Leu Glu Gly
705                 710                 715                 720

Val Val Ser Gln Ile Asp Ala Val Gly Ser Lys Leu Lys Met Leu Glu
                725                 730                 735

Arg Lys Gly Glu Leu Ala Pro Ser Pro Gly Met Gly Glu Pro Ala Val
                740                 745                 750

Trp Glu Asn Leu Tyr Asn Pro Ser
                755                 760

<210> SEQ ID NO 14
<211> LENGTH: 805
<212> TYPE: PRT
<213> ORGANISM: Homo sapiens

<400> SEQUENCE: 14

Met Asn Ala Val Gly Ser Pro Glu Gly Gln Glu Leu Gln Lys Leu Gly
1               5                   10                  15

Ser Gly Ala Trp Asp Asn Pro Ala Tyr Ser Gly Pro Pro Ser Pro His
                20                  25                  30

Gly Thr Leu Arg Val Cys Thr Ile Ser Ser Thr Gly Pro Leu Gln Pro
                35                  40                  45

Gln Pro Lys Lys Pro Glu Asp Glu Pro Gln Glu Thr Ala Tyr Arg Thr
                50                  55                  60
```

```
Gln Val Ser Ser Cys Cys Leu His Ile Cys Gln Gly Ile Arg Gly Leu
 65                  70                  75                  80

Trp Gly Thr Thr Leu Thr Glu Asn Thr Ala Glu Asn Arg Glu Leu Tyr
             85                  90                  95

Ile Lys Thr Thr Leu Arg Glu Leu Leu Val Tyr Ile Val Phe Leu Val
            100                 105                 110

Asp Ile Cys Leu Leu Thr Tyr Gly Met Thr Ser Ser Ser Ala Tyr Tyr
            115                 120                 125

Tyr Thr Lys Val Met Ser Glu Leu Phe Leu His Thr Pro Ser Asp Thr
130                 135                 140

Gly Val Ser Phe Gln Ala Ile Ser Ser Met Ala Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly His Gly Ser His Ser Phe Ile Tyr Tyr Glu Asn
            180                 185                 190

Met Leu Leu Gly Val Pro Arg Leu Arg Gln Leu Lys Val Arg Asn Asp
            195                 200                 205

Ser Cys Val Val His Glu Asp Phe Arg Glu Asp Ile Leu Ser Cys Tyr
210                 215                 220

Asp Val Tyr Ser Pro Asp Lys Glu Glu Gln Leu Pro Phe Gly Pro Phe
225                 230                 235                 240

Asn Gly Thr Ala Trp Thr Tyr His Ser Gln Asp Glu Leu Gly Gly Phe
                245                 250                 255

Ser His Trp Gly Arg Leu Thr Ser Tyr Ser Gly Gly Tyr Tyr Leu
            260                 265                 270

Asp Leu Pro Gly Ser Arg Gln Gly Ser Ala Glu Ala Leu Arg Ala Leu
            275                 280                 285

Gln Glu Gly Leu Trp Leu Asp Arg Gly Thr Arg Val Val Phe Ile Asp
290                 295                 300

Phe Ser Val Tyr Asn Ala Asn Ile Asn Leu Phe Cys Val Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Ser Asn Trp Asp Phe Phe Ile
            340                 345                 350

Val Gly Cys Glu Val Ile Phe Cys Val Phe Ile Phe Tyr Tyr Val Val
            355                 360                 365

Glu Glu Ile Leu Glu Leu His Ile His Arg Leu Arg Tyr Leu Ser Ser
370                 375                 380

Ile Trp Asn Ile Leu Asp Leu Val Val Ile Leu Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asn Thr Tyr Ala Asp Phe Glu Phe Leu Ala
            420                 425                 430

Phe Trp Gln Thr Gln Tyr Asn Asn Met Asn Ala Val Asn Leu Phe Phe
            435                 440                 445

Ala Trp Ile Lys Ile Phe Lys Tyr Ile Ser Phe Asn Lys Thr Met Thr
450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
```

```
                 485                 490                 495
Leu Leu Phe Gly Thr Gln Val Glu Asn Phe Ser Thr Phe Ile Lys Cys
            500                 505                 510

Ile Phe Thr Gln Phe Arg Ile Ile Leu Gly Asp Phe Asp Tyr Asn Ala
        515                 520                 525

Ile Asp Asn Ala Asn Arg Ile Leu Gly Pro Ala Tyr Phe Val Thr Tyr
    530                 535                 540

Val Phe Phe Val Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575

Glu Leu Gln Leu Ser Asp Leu Leu Lys Gln Gly Tyr Asn Lys Thr Leu
            580                 585                 590

Leu Arg Leu Arg Leu Arg Lys Glu Arg Val Ser Asp Val Gln Lys Val
        595                 600                 605

Leu Gln Gly Gly Glu Gln Glu Ile Gln Phe Glu Asp Phe Thr Asn Thr
    610                 615                 620

Leu Arg Glu Leu Gly His Ala Glu His Glu Ile Thr Glu Leu Thr Ala
625                 630                 635                 640

Thr Phe Thr Lys Phe Asp Arg Asp Gly Asn Arg Ile Leu Asp Glu Lys
                645                 650                 655

Glu Gln Glu Lys Met Arg Gln Asp Leu Glu Glu Arg Val Ala Leu
            660                 665                 670

Asn Thr Glu Ile Glu Lys Leu Gly Arg Ser Ile Val Ser Ser Pro Gln
    675                 680                 685

Gly Lys Ser Gly Pro Glu Ala Ala Arg Ala Gly Gly Trp Val Ser Gly
    690                 695                 700

Glu Glu Phe Tyr Met Leu Thr Arg Arg Val Leu Gln Leu Glu Thr Val
705                 710                 715                 720

Leu Glu Gly Val Val Ser Gln Ile Asp Ala Val Gly Ser Lys Leu Lys
                725                 730                 735

Met Leu Glu Arg Lys Gly Trp Leu Ala Pro Pro Gly Val Lys Glu
            740                 745                 750

Gln Ala Ile Trp Lys His Pro Gln Pro Ala Pro Ala Val Thr Pro Asp
        755                 760                 765

Pro Trp Gly Val Gln Gly Gln Glu Ser Glu Val Pro Tyr Lys Arg
    770                 775                 780

Glu Glu Glu Ala Leu Glu Glu Arg Arg Leu Ser Arg Gly Glu Ile Pro
785                 790                 795                 800

Thr Leu Gln Arg Ser
                805

<210> SEQ ID NO 15
<211> LENGTH: 2318
<212> TYPE: PRT
<213> ORGANISM: Rattus norvegicus

<400> SEQUENCE: 15

Met Leu Leu Gln Arg Pro Ser Trp Leu Trp Leu Tyr Leu Arg Ile Ser
1               5                   10                  15

Val Val Leu Gly Val Leu Leu Gly Arg Glu Pro Ser Ile Pro Glu Gln
                20                  25                  30

His Gly Lys Asn Ser Cys Tyr Gln Leu Asn Arg Leu Tyr Cys Ser Phe
            35                  40                  45
```

-continued

```
His Glu Ala Glu Met Tyr Cys His Ala Gln Arg Gly His Leu Ala Asn
 50                  55                  60
Thr Trp Asn Pro Lys Leu Gln Asp Phe Leu Gln Asn Ser Pro Gln Lys
 65                  70                  75                  80
Glu Thr Val Trp Val Gly Ile Asn Leu Lys Leu Pro Arg Lys Gln
                 85                  90                  95
Pro Gly Ile Thr Gln Thr Gly Ala Ala Ala Lys Lys Pro Asp Glu Cys
                100                 105                 110
Thr Ser Val Val Lys Arg Ser Asn Ala Phe Phe Pro Arg Trp Asp Gln
                115                 120                 125
Cys Leu Lys Lys His His Phe Ile Cys Gln Ala Ala Leu Gly Cys Arg
    130                 135                 140
Gly Lys Met Gly Lys Glu Met Arg Pro Trp His Arg Lys Thr Arg Arg
145                 150                 155                 160
Pro Glu Ala Met Ser Ser Lys Lys Tyr Ala Ser Leu His Leu Glu Asp
                165                 170                 175
Gln Asp Gly Arg Glu Ser Val Trp Ser Gly Pro Gln Gln Leu Arg Leu
                180                 185                 190
Leu Pro Val Ser Pro His Lys Val Arg Phe Ser Val Trp His Arg Leu
                195                 200                 205
Ala Leu Gln Leu Asn Pro Val Ala Val Pro Pro Gln Gly Ala Asn Ile
    210                 215                 220
Trp Arg Asn Glu Leu Asp Pro Trp Lys Pro Met Lys Lys Arg Gly Ala
225                 230                 235                 240
Glu Leu Glu Arg His Met Ile Pro Gly Asp Gly Pro Pro Leu Ser Met
                245                 250                 255
Cys His Pro Pro Ala Pro Pro Glu Leu Ser Glu Ile Leu Cys Phe Pro
                260                 265                 270
Ile Asp Pro Val Ser Ser Val Leu Pro Lys Ala Thr His Lys Met Thr
    275                 280                 285
Ile Thr Ser Pro Thr Arg Ser Ser Gln Val Thr Ser Val Val Thr Ala
    290                 295                 300
Ser Ser Ser Pro Pro Gln Val Thr Ser Asp Thr Pro Ala Ser Ser Ser
305                 310                 315                 320
Ser Pro Pro Gln Val Thr Ser Asp Thr Pro Ala Ser Ser Ser Ser Pro
                325                 330                 335
Pro Gln Val Thr Ser Asp Thr Pro Ser Ser Ser Ser Pro Pro Gln
                340                 345                 350
Val Thr Ser Asp Thr Pro Ala Ser Ser Ser Leu Pro Gln Val Thr Ser
                355                 360                 365
Asp Thr Pro Ala Ser Ser Pro Pro Gln Val Thr Ser Asp Thr Pro
    370                 375                 380
Ala Ser Ser Pro Pro Gln Val Thr Ser Asp Thr Pro Ala Ser Ser
385                 390                 395                 400
Ser Pro Pro Gln Val Thr Ser Asp Thr Pro Ala Ser Ser Pro Pro
                405                 410                 415
Gln Val Thr Ser Asp Thr Ser Ala Ser Ser Pro Pro Gln Val Thr
                420                 425                 430
Ser Asp Thr Pro Ala Ser Ser Pro Pro Gln Val Thr Ser Asp Thr
                435                 440                 445
Pro Ala Ser Ser Ile Thr Pro Gln Val Thr Thr Asp Thr Pro Val Ser
    450                 455                 460
Ser Ser Pro Pro Gln Val Thr Ser Asp Thr Pro Ala Ser Ser Ser Pro
```

-continued

```
              465                 470                 475                 480
          Pro Gln Val Thr Ser Asp Thr Pro Ala Ser Ser Ser Pro Leu Gln Val
                          485                 490                 495
          Thr Ser Asp Thr Thr Ala Ser Ser Ser Pro Pro Gln Val Thr Ser Asp
                          500                 505                 510
          Thr Pro Ala Ser Ser Ser Ser Pro Leu Gln Val Thr Ser Asp Thr Pro
                          515                 520                 525
          Ala Ser Ser Ile Thr Pro Gln Val Thr Ser Asp Thr Pro Val Ser Ser
                          530                 535                 540
          Ser Pro Pro Gln Val Thr Ser Asp Thr Pro Ala Ser Ser Ser Ser Pro
          545                 550                 555                 560
          Pro Gln Val Thr Ser Asp Thr Pro Ala Ser Ser Ser Pro Pro Gln
                          565                 570                 575
          Val Thr Ser Asp Thr Pro Ser Ser Ser Ser Pro Pro Gln Val Thr
                          580                 585                 590
          Ser Asp Thr Pro Ala Ser Ser Ser Leu Pro Gln Val Thr Ser Asp Thr
                          595                 600                 605
          Pro Ala Ser Ser Ser Pro Pro Gln Val Thr Ser Asp Thr Pro Ala Ser
                          610                 615                 620
          Ser Ser Pro Pro Gln Val Thr Ser Asp Thr Pro Ala Ser Ser Ser Ser
          625                 630                 635                 640
          Pro Leu Gln Val Thr Ser Asp Thr Pro Val Pro Asn Ser Pro Pro Trp
                          645                 650                 655
          Pro Val Ile Thr Glu Val Thr Arg Leu Glu Ser Thr Ile Pro Thr Gly
                          660                 665                 670
          Arg Ser Leu Ala Asp Ile Thr Leu Asn Ala Lys Glu Asp Ser Pro Pro
                          675                 680                 685
          Gly Val Ile Ser Thr His Pro Gln Met Ser Phe Gln Ser Ser Thr Asn
                          690                 695                 700
          Gln Leu Pro Ile Ala Arg Ile Ala Ser Gly Asn Ser Ser Phe Gln Trp
          705                 710                 715                 720
          Val Met Gly Trp Gln Leu Gln Pro Pro Ala Pro Arg Ile Phe Ile Val
                          725                 730                 735
          Phe Ala Pro Gln Ser Val Lys Ala Thr Ile Arg Ser Arg Ser His Leu
                          740                 745                 750
          Ser Ser Pro Thr Ile Phe Ser Pro Gln Gln Val Ile Glu Glu Thr Ala
                          755                 760                 765
          Gly Lys Leu Ile Leu Ala Asn Pro Ala Ser Gln Ala His Ser Glu Phe
                          770                 775                 780
          Gln Lys Ala Cys Ser Ile Leu Gln Arg Leu Arg Asp Phe Leu Pro Thr
          785                 790                 795                 800
          Ser Ser Thr Ser Ala Gln Val Ser Val Ala Ser Leu Leu Ile Asp Leu
                          805                 810                 815
          Ser Glu Gln Leu Leu Thr Leu Pro Phe Gln Arg Asn Asn Ser Trp Ser
                          820                 825                 830
          Ser His Thr Pro Ala Val Ser Cys Pro Phe Gln Pro Leu Gly Ser Leu
                          835                 840                 845
          Leu Thr Thr Lys Lys Asn Ser His Gln Met Ala Gln Gln Asp Thr Glu
                          850                 855                 860
          Gln Val Glu Asp Met Leu Glu Thr Ser Leu Met Ala Leu Gly Glu Ile
          865                 870                 875                 880
          His Arg Thr Phe Cys Gln Gln Ser Leu Cys Pro Gln Ser Ala Val Thr
                          885                 890                 895
```

-continued

```
Leu Ala Ser Pro Thr Ala Thr Leu Val Leu Ser Ser Gln Asn Val Ser
              900                 905                 910

Ser Leu Pro Leu Ser Thr Tyr Thr Leu Gly Glu Pro Ala Pro Leu Arg
              915                 920                 925

Leu Gly Phe Pro Ser Ala Glu Ala Leu Lys Glu Leu Leu Asp Lys His
              930                 935                 940

Pro Gly Val Asn Leu Gln Val Thr Gly Leu Ala Phe Asn Pro Phe Glu
945                 950                 955                 960

Thr Ser Asp Asp Ser Asn Ile Val Gly Ser Ile Gly Asn Val Leu Leu
                  965                 970                 975

Ser Ser Glu Tyr Gln Leu Ile Arg Val His Asp Leu Ile Glu Asp Ile
              980                 985                 990

Glu Ile Val Leu Trp Arg Asn Ala  Ser Met Glu Thr Gln  Pro Thr Ser
              995                 1000                1005

Leu Asn  Thr Ser Thr Asp Cys  Phe Thr Ile Ser Val  Asn Ile Thr
     1010                 1015                 1020

Ser Leu  Glu Lys Thr Leu Ile  Val Thr Ile Glu Pro  Glu Ser Pro
     1025                 1030                 1035

Leu Leu  Met Thr Leu His Leu  Gly Phe Gln Asp Lys  Pro Gly His
     1040                 1045                 1050

Thr His  Phe Tyr Leu Asn Ile  Ser Leu Pro Arg Gly  Gln Val Trp
     1055                 1060                 1065

Gln Lys  Asp Glu Glu Tyr Thr  Trp Val Leu Thr Pro  Glu Ser Leu
     1070                 1075                 1080

Trp Tyr  Gly Thr Gly Thr Tyr  Tyr Ile Met Ala Val  Glu Asn Lys
     1085                 1090                 1095

Ser Ala  Glu Thr Ala Gln His  Thr Pro Val Leu Val  Ser Val Val
     1100                 1105                 1110

Thr Ala  Val Thr Gln Cys Tyr  Phe Trp Asp Arg Tyr  Asn Arg Thr
     1115                 1120                 1125

Trp Lys  Ser Asp Gly Cys Gln  Val Gly Pro Lys Ser  Thr Ile Leu
     1130                 1135                 1140

Lys Thr  Gln Cys Leu Cys Asp  His Leu Thr Phe Phe  Ser Ser Asp
     1145                 1150                 1155

Phe Phe  Ile Val Pro Arg Thr  Val Asp Val Glu Asn  Thr Ile Lys
     1160                 1165                 1170

Leu Leu  Leu His Val Ser Asn  Asn Pro Val Gly Val  Ser Leu Leu
     1175                 1180                 1185

Ala Ser  Leu Leu Gly Phe Tyr  Ile Leu Leu Ala Thr  Trp Ala Trp
     1190                 1195                 1200

Arg Lys  Asp Gln Ala Asp Thr  Gln Lys Val Lys Val  Thr Val Leu
     1205                 1210                 1215

Ala Asp  Asn Asp Pro Ser Ser  Ala Phe His Tyr Leu  Ile Gln Val
     1220                 1225                 1230

Tyr Thr  Gly Tyr Arg Arg Arg  Ala Ala Thr Thr Ala  Lys Val Val
     1235                 1240                 1245

Ile Thr  Leu Tyr Gly Ser Glu  Gly His Ser Glu Pro  His His Leu
     1250                 1255                 1260

Cys Asp  Pro Gln Lys Thr Val  Phe Glu Arg Gly Ala  Leu Asp Val
     1265                 1270                 1275

Phe Leu  Leu Ser Thr Gly Ser  Trp Leu Gly Asp Leu  His Gly Leu
     1280                 1285                 1290
```

-continued

```
Arg Leu Trp His Asp Asn Ser Gly Asn Ser Pro Ser Trp Tyr Val
1295                1300                1305

Ser Gln Val Val Ser Asp Met Thr Val Lys Lys Lys Cys His
1310                1315                1320

Phe Gln Cys Asn Cys Trp Leu Ala Met Asp Leu Gly Asn Cys Glu
1325                1330                1335

Arg Asp Arg Val Phe Thr Pro Ala Ser Arg Ser Glu Leu Ser Ser
1340                1345                1350

Phe Arg His Leu Phe Ser Ser Thr Ile Val Glu Lys Phe Thr Gln
1355                1360                1365

Asp Tyr Leu Trp Leu Ser Val Ala Thr Arg His Pro Trp Asn Gln
1370                1375                1380

Phe Thr Arg Val Gln Arg Leu Ser Cys Cys Met Thr Leu Leu Leu
1385                1390                1395

Cys Asp Met Val Ile Asn Val Met Phe Trp Lys Met Gly Gly Ser
1400                1405                1410

Thr Ala Lys Arg Gly Glu Arg Leu Gly Pro Leu Ala Val Thr Leu
1415                1420                1425

Ser Glu Leu Leu Val Ser Ile Gln Thr Ser Val Ile Leu Phe Pro
1430                1435                1440

Ile His Leu Val Phe Gly Arg Leu Phe Gln Leu Val His Pro Pro
1445                1450                1455

Glu Val Leu Pro Pro Leu Pro Leu Ser Gln Ala Ala Cys Pro Ser
1460                1465                1470

Val Leu Val Arg Glu Thr Pro Ser Leu Thr Gln Val Val Lys Glu
1475                1480                1485

Leu Lys Glu Thr Val Gly Phe Leu Leu Arg Arg Asn Thr His Leu
1490                1495                1500

Leu Ser Glu Cys Glu Gln Ser Ser Trp Ser Ser Cys Asp Ile Asn
1505                1510                1515

Thr Leu Val Lys Leu Leu Ser Gly Leu Val Tyr Ser His Leu Glu
1520                1525                1530

Asp Gln Gly Cys His Gln Gln Thr Glu Ser Arg Trp Glu Asp Gly
1535                1540                1545

Val Ser Glu Ser His Ser His Phe Cys Arg Tyr Leu Leu Arg Val
1550                1555                1560

Leu Gln Ser Leu Lys Leu Arg Leu Gly Ala Leu Ala Ala Val Gln
1565                1570                1575

Glu His Gln Pro Tyr Asp Phe Ser Glu Ala Val Ser Gln Leu Gln
1580                1585                1590

Asn Leu Gln Glu Leu Leu Arg Thr Gln Thr Leu Pro Lys Glu Pro
1595                1600                1605

Arg Pro Cys Arg His Ser Thr Ser Phe Pro Ile Leu Asn Thr Glu
1610                1615                1620

Gly Gly Lys Lys Pro Val Pro Phe Cys Leu Phe Arg Trp Leu Arg
1625                1630                1635

Tyr Ser Cys Trp Leu Leu Leu Gly Val Ile Ser Leu Thr Ser Ala
1640                1645                1650

Phe Phe Ile Thr Leu Tyr Ser Leu Glu Leu Ser Arg Asp Gln Ala
1655                1660                1665

Thr Ser Trp Val Ile Ser Met Met Leu Ser Val Leu Gln Asp Ile
1670                1675                1680

Phe Ile Cys Gln Pro Ile Lys Val Ile Phe Leu Thr Leu Leu Phe
```

-continued

```
           1685                1690                1695

Ser Leu Met Ala Asn His Met Pro Trp Leu Thr Lys Asp Lys Glu
    1700                1705                1710

His His Ala Arg Arg Ile Val Ala Leu Trp Ala Lys Cys Pro Ser
    1715                1720                1725

Ser Ala Pro Gly Leu Arg Asp Lys Asn Pro Ile Tyr Thr Ala
    1730                1735                1740

Pro Ala Met Asn His Leu Asp Arg Arg Thr Lys Lys Val Trp Arg
    1745                1750                1755

Lys Arg Leu Phe Leu Leu Thr Ala Gly Ser Leu Val Gln Ile Leu
    1760                1765                1770

Phe Leu Thr Leu Leu Met Thr Thr Val Tyr Ser Ala Lys Asp Ser
    1775                1780                1785

Ser Arg Phe Phe Leu His Arg Ala Val Trp Lys Arg Phe Ser His
    1790                1795                1800

Gly Phe Ser Glu Ile Lys Ala Val Glu Asp Phe Tyr Pro Trp Ala
    1805                1810                1815

Asn Arg Thr Leu Leu Pro Asn Leu Tyr Gly Asp Tyr Arg Glu Glu
    1820                1825                1830

His His Ser Ala Glu Gln Arg Gly His Leu Leu Arg Leu Ala Pro
    1835                1840                1845

Thr Tyr Gln His Asp Thr Arg Val Asp Phe Ser Ala Leu Ala Val
    1850                1855                1860

Arg Val Pro Leu Phe Arg Gly Arg Gly Leu Gly Pro Ala Leu Asp
    1865                1870                1875

Asp Arg Ser Glu Cys Ser Glu Gln Cys Leu Ala Gln Gly Phe Ile
    1880                1885                1890

Thr Asp Gly Asn Ser Phe Leu Leu Gly Asn Val Leu Leu Arg Gln
    1895                1900                1905

Ile Leu Phe Pro Asn Asp Thr His Ser Pro Val Ser Leu His Glu
    1910                1915                1920

His Met Asn Ser Tyr Pro Gln His Gln Glu Asp Arg Glu Asn Tyr
    1925                1930                1935

Gly Ala Gly Trp Val Pro Pro Asp Thr Asn Ile Thr Lys Ala Asp
    1940                1945                1950

Ser Ile Trp His Tyr Gln Ser Pro Glu Ser Leu Gly Gly Tyr Pro
    1955                1960                1965

Ile Gln Gly Glu Val Thr Thr Tyr Ser Gly Gly Gly Tyr Val Val
    1970                1975                1980

Arg Leu Gly Arg Asn His Ser Ala Ala Thr Arg Val Leu Gln His
    1985                1990                1995

Leu Glu Gln Arg His Trp Leu Asp His Tyr Thr Lys Ala Leu Phe
    2000                2005                2010

Val Glu Phe Thr Val Phe Asn Ala Asn Val Asn Leu Leu Cys Met
    2015                2020                2025

Val Thr Leu Ile Leu Glu Ser Ser Gly Val Gly Thr Phe Phe Thr
    2030                2035                2040

Ser Leu Arg Leu Asp Ser Leu Thr Ser Leu Gln Ser Ser Glu Arg
    2045                2050                2055

Gly Phe Ala Trp Ile Ile Ser Gln Val Ala Tyr Tyr Leu Leu Val
    2060                2065                2070

Cys Tyr Tyr Ala Phe Val Gln Gly Cys Arg Leu Lys Arg Gln Gly
    2075                2080                2085
```

```
Leu Ala Phe Phe Thr Arg Arg Arg Asn Ile Leu Asp Thr Ser Ile
    2090            2095                2100

Ile Leu Thr Ser Phe Ser Ile Leu Gly Leu Asn Met Gln Ser Leu
    2105            2110                2115

Ser Leu Leu His Thr Asn Met Gln Gln Tyr Arg Arg Asp Pro Asp
    2120            2125                2130

Gly Phe Ile Ser Phe Ser Glu Ala Leu Arg Val Asn Ser Val Ala
    2135            2140                2145

Thr His Leu Met Gly Phe Leu Leu Leu Phe Ala Thr Val Arg Val
    2150            2155                2160

Trp Asp Leu Leu Arg His His Ala Arg Leu Gln Val Ile Asn Lys
    2165            2170                2175

Thr Leu Thr Lys Ala Trp Asp Glu Val Leu Gly Phe Ile Met Ile
    2180            2185                2190

Ile Met Ile Leu Leu Ser Ser Tyr Ala Met Thr Phe Asn Leu Leu
    2195            2200                2205

Phe Gly Trp Ser Ile Ser Asp Tyr Gln Ser Phe Phe Ser Ser Val
    2210            2215                2220

Val Thr Val Val Gly Leu Leu Val Gly Ile Pro Lys His Lys Glu
    2225            2230                2235

Val Val Ala Leu Ser Pro Val Leu Gly Ser Phe Leu Val Leu Ser
    2240            2245                2250

Asn Ile Ile Leu Met Gly Leu Val Ile Ile Asn Leu Phe Val Ser
    2255            2260                2265

Ala Ile Leu Ile Val Phe Gly Lys Glu Arg Lys Ala Cys Glu Lys
    2270            2275                2280

Glu Ala Thr Leu Thr Asp Met Leu Leu Gln Lys Leu Ser Ser Leu
    2285            2290                2295

Leu Gly Ile Arg Gln His Gln Lys Pro Ala Ser Glu Lys His Ala
    2300            2305                2310

Asp Ser Thr Gly Tyr
    2315

<210> SEQ ID NO 16
<211> LENGTH: 2151
<212> TYPE: PRT
<213> ORGANISM: Mus musculus

<400> SEQUENCE: 16

Met Leu Leu Gln Arg Arg Ser Trp Leu Trp Leu Tyr Ile Arg Ile Gly
1               5                   10                  15

Val Ile Leu Gly Asp Ile Leu Gly Arg Lys Pro Ser Ile Arg Glu Gln
                20                  25                  30

His Gly Gly Asn Ser Cys Tyr Gln Leu Asn Arg Leu Phe Cys Asp Phe
            35                  40                  45

Gln Glu Ala Asp Asn Tyr Cys His Ala Gln Arg Gly Arg Leu Ala His
        50                  55                  60

Thr Trp Asn Pro Lys Leu Arg Gly Phe Leu Lys Ser Phe Leu Asn Glu
65                  70                  75                  80

Glu Thr Val Trp Trp Val Arg Gly Asn Leu Thr Leu Pro Gly Ser His
                85                  90                  95

Pro Gly Ile Asn Gln Thr Gly Gly Asp Asp Val Leu Arg Asn Gln Lys
            100                 105                 110

Pro Gly Glu Cys Pro Ser Val Val Thr His Ser Asn Ala Val Phe Ser
```

-continued

```
            115                 120                 125
Arg Trp Asn Leu Cys Ile Glu Lys His His Phe Ile Cys Gln Ala Ala
130                 135                 140
Ala Phe Pro Pro Gln Gly Ala Ser Ile Trp Arg Asn Glu Phe Gly Pro
145                 150                 155                 160
Gly Pro Leu Leu Pro Met Lys Arg Arg Gly Ala Glu Thr Glu Arg His
                165                 170                 175
Met Ile Pro Gly Asn Gly Pro Pro Leu Ala Met Cys His Gln Pro Ala
                180                 185                 190
Pro Pro Glu Leu Phe Glu Thr Leu Cys Phe Pro Ile Asp Pro Ala Ser
            195                 200                 205
Ser Ala Pro Pro Lys Ala Thr His Arg Met Thr Ile Thr Ser Leu Thr
210                 215                 220
Gly Arg Pro Gln Val Thr Ser Asp Thr Leu Ala Ser Ser Pro Pro
225                 230                 235                 240
Gln Gly Thr Ser Asp Thr Pro Ala Ser Ser Pro Pro Gln Val Thr
                245                 250                 255
Ser Ala Thr Ser Ala Ser Ser Pro Pro Gln Gly Thr Ser Asp Thr
                260                 265                 270
Pro Ala Ser Ser Pro Pro Gln Val Thr Ser Ala Thr Ser Ala Ser
            275                 280                 285
Ser Ser Pro Pro Gln Gly Thr Ser Asp Thr Pro Ala Ser Ser Pro
            290                 295                 300
Pro Gln Val Thr Ser Ala Thr Ser Ala Ser Ser Pro Pro Gln Gly
305                 310                 315                 320
Thr Ser Asp Thr Pro Ala Ser Ser Pro Pro Gln Val Thr Ser Ala
                325                 330                 335
Thr Ser Ala Ser Ser Pro Pro Gln Gly Thr Ser Asp Thr Pro Ala
                340                 345                 350
Ser Ser Ser Pro Pro Gln Gly Thr Leu Asp Thr Pro Ser Ser Ser
            355                 360                 365
Pro Pro Gln Gly Thr Ser Asp Thr Pro Ala Ser Ser Pro Pro Gln
        370                 375                 380
Gly Thr Ser Glu Thr Pro Ala Ser Asn Ser Pro Pro Gln Gly Thr Ser
385                 390                 395                 400
Glu Thr Pro Gly Phe Ser Ser Pro Pro Gln Val Thr Thr Ala Thr Leu
                405                 410                 415
Val Ser Ser Pro Pro Gln Val Thr Ser Glu Thr Pro Ala Ser Ser
                420                 425                 430
Ser Pro Thr Gln Val Thr Ser Glu Thr Pro Ala Ser Ser Pro Thr
        435                 440                 445
Gln Val Thr Ser Asp Thr Pro Ala Ser Asn Ser Pro Pro Gln Gly Thr
        450                 455                 460
Ser Asp Thr Pro Gly Phe Ser Ser Pro Thr Gln Val Thr Thr Ala Thr
465                 470                 475                 480
Leu Val Ser Ser Pro Pro Gln Val Thr Ser Asp Thr Pro Ala Ser
                485                 490                 495
Ser Ser Pro Pro Gln Val Thr Ser Asp Thr Pro Ala Ser Ser Pro
            500                 505                 510
Pro Gln Val Thr Ser Glu Thr Pro Ala Ser Ser Ser Pro Pro Gln Val
        515                 520                 525
Thr Ser Asp Thr Ser Ala Ser Ile Ser Pro Pro Gln Val Ile Ser Asp
        530                 535                 540
```

-continued

```
Thr Pro Ala Ser Ser Ser Pro Gln Val Thr Ser Glu Thr Pro Ala
545                 550                 555                 560

Ser Ser Ser Pro Thr Asn Met Thr Ser Asp Thr Pro Ala Ser Ser
                565                 570                 575

Pro Thr Asn Met Thr Ser Asp Thr Pro Ala Ser Ser Ser Pro Thr Asn
            580                 585                 590

Met Thr Ser Asp Thr Pro Ala Ser Ser Ser Pro Pro Trp Pro Val Ile
                595                 600                 605

Thr Glu Val Thr Arg Pro Glu Ser Thr Ile Pro Ala Gly Arg Ser Leu
            610                 615                 620

Ala Asn Ile Thr Ser Lys Ala Gln Glu Asp Ser Pro Leu Gly Val Ile
625                 630                 635                 640

Ser Thr His Pro Gln Met Ser Phe Gln Ser Ser Thr Ser Gln Ala Leu
                645                 650                 655

Asp Glu Thr Ala Gly Glu Arg Val Pro Thr Ile Pro Asp Phe Gln Ala
                660                 665                 670

His Ser Glu Phe Gln Lys Ala Cys Ala Ile Leu Gln Arg Leu Arg Asp
            675                 680                 685

Phe Leu Pro Thr Ser Pro Thr Ser Ala Gln Val Ser Val Ala Asn Leu
690                 695                 700

Leu Ile Asp Leu Ser Glu Gln Leu Leu Val Leu Pro Phe Gln Lys Asn
705                 710                 715                 720

Asn Ser Trp Ser Ser Gln Thr Pro Ala Val Ser Cys Pro Phe Gln Pro
                725                 730                 735

Leu Gly Arg Leu Thr Thr Thr Glu Lys Ser Ser His Gln Met Ala Gln
            740                 745                 750

Gln Asp Met Glu Gln Val Glu Asp Met Leu Glu Thr Ser Leu Met Ala
            755                 760                 765

Leu Gly Glu Ile His Arg Ala Phe Cys Gln Gln Ser Leu Cys Pro Gln
770                 775                 780

Ser Ala Val Thr Leu Ala Ser Pro Ser Ala Thr Leu Met Leu Ser Ser
785                 790                 795                 800

Gln Asn Val Ser Thr Leu Pro Leu Ser Thr Tyr Thr Leu Gly Glu Pro
                805                 810                 815

Ala Pro Leu Thr Leu Gly Phe Pro Ser Ala Glu Ala Leu Lys Glu Leu
            820                 825                 830

Leu Asn Lys His Pro Gly Val Asn Leu Gln Val Thr Gly Leu Ala Phe
            835                 840                 845

Asn Pro Phe Lys Thr Leu Asp Asp Lys Asn Ile Val Gly Ser Ile Gly
850                 855                 860

Asn Val Gln Leu Ser Ser Ala Tyr Gln Ser Ile Arg Val His Asp Leu
865                 870                 875                 880

Ile Glu Asp Ile Glu Ile Met Leu Trp Arg Asn Ala Ser Met Glu Thr
                885                 890                 895

Gln Pro Thr Ser Leu Asn Thr Ser Thr Asp His Phe Thr Ile Ser Val
            900                 905                 910

Asn Ile Thr Ser Leu Glu Lys Thr Leu Ile Val Thr Ile Glu Pro Glu
            915                 920                 925

Ser Pro Leu Leu Met Thr Leu His Leu Gly Phe Gln Asp Gln Leu Ala
930                 935                 940

His Thr His Phe Tyr Leu Asn Ile Ser Leu Pro Arg Asp Gln Val Trp
945                 950                 955                 960
```

-continued

```
Gln Lys Asp Glu Glu Tyr Thr Trp Val Leu Thr Pro Glu Asn Leu Trp
            965                 970                 975

Tyr Gly Thr Gly Thr Tyr Tyr Ile Met Ala Val Glu Asn Lys Ser Thr
            980                 985                 990

Glu Ala Ala Gln His Thr Pro Val Leu Val Ser Val Val Thr Ala Val
            995                 1000                1005

Thr Gln Cys Tyr Phe Trp Asp Arg Tyr Asn Arg Thr Trp Lys Ser
        1010                1015                1020

Asp Gly Cys Gln Val Gly Pro Lys Ser Thr Ile Leu Lys Thr Gln
        1025                1030                1035

Cys Leu Cys Asp His Leu Thr Phe Phe Ser Ser Asp Phe Phe Ile
        1040                1045                1050

Val Pro Arg Thr Val Asp Val Glu Asn Thr Ile Lys Leu Leu Leu
        1055                1060                1065

His Val Thr Asn Asn Pro Val Gly Val Ser Leu Leu Ser Ser Leu
        1070                1075                1080

Leu Gly Phe Tyr Ile Leu Leu Ala Met Trp Ala Ser Arg Lys Asp
        1085                1090                1095

Arg Glu Asp Met Gln Lys Val Lys Val Thr Val Leu Ala Asp Asn
        1100                1105                1110

Asp Pro Ser Ser Ala Ser His Tyr Leu Ile Gln Val Tyr Thr Gly
        1115                1120                1125

Tyr Arg Arg Ala Ala Thr Thr Ala Lys Val Val Ile Thr Leu
        1130                1135                1140

Tyr Gly Ser Glu Gly His Ser Glu Pro His His Leu Cys Asp Pro
        1145                1150                1155

Glu Lys Thr Val Phe Glu Arg Gly Ala Leu Asp Val Phe Leu Leu
        1160                1165                1170

Ser Thr Gly Ser Trp Leu Gly Asp Leu His Gly Leu Arg Leu Trp
        1175                1180                1185

His Asp Asn Ser Gly Asp Ser Pro Ser Trp Tyr Val Ser Gln Val
        1190                1195                1200

Ile Val Ser Asp Met Thr Thr Arg Lys Lys Trp His Phe Gln Cys
        1205                1210                1215

Asn Cys Trp Leu Ala Val Asp Leu Gly Asn Cys Glu Arg Asp Arg
        1220                1225                1230

Val Phe Thr Pro Ala Ser Arg Ser Glu Leu Ser Ser Phe Arg His
        1235                1240                1245

Leu Phe Ser Ser Thr Ile Val Glu Lys Phe Thr Gln Asp Tyr Leu
        1250                1255                1260

Trp Leu Ser Val Ala Thr Arg His Pro Trp Asn Gln Phe Thr Arg
        1265                1270                1275

Val Gln Arg Leu Ser Cys Cys Met Ala Leu Leu Leu Cys Asp Met
        1280                1285                1290

Val Ile Asn Ile Met Phe Trp Lys Met Gly Gly Thr Thr Ala Lys
        1295                1300                1305

Arg Gly Thr Glu Gln Leu Gly Pro Leu Ala Val Thr Leu Ser Glu
        1310                1315                1320

Leu Leu Val Ser Ile Gln Thr Ser Ile Ile Leu Phe Pro Ile His
        1325                1330                1335

Leu Ile Phe Gly Arg Leu Phe Gln Leu Ile His Pro Pro Glu Ala
        1340                1345                1350

Leu Pro Gln Leu Pro Phe Ile Gln Ala Ala Trp Pro Pro Ala Leu
```

```
                1355                1360                1365
Val Cys Glu Ser Pro Ser Leu Thr Gln Val Val Lys Glu Leu Lys
    1370                1375                1380
Glu Thr Val Gly Phe Leu Leu Arg Arg Asn Thr Gln Leu Leu Ser
    1385                1390                1395
Glu Cys Glu Pro Ser Ser Cys Ser Ser Cys Asp Ile Asn Lys Leu
    1400                1405                1410
Ala Lys Leu Leu Ser Gly Leu Ile Tyr Cys His Leu Glu Asp Glu
    1415                1420                1425
Gly Cys His Gln Gln Thr Glu Ser His Trp Glu Asp Ala Val Ser
    1430                1435                1440
Glu Asn His Tyr His Phe Cys Arg Tyr Leu Leu Gln Leu Leu Arg
    1445                1450                1455
Arg Leu Lys Ala His Leu Glu Ala Leu Gly Ala Thr Gln Asp His
    1460                1465                1470
Gln Ser Cys Asp Phe Ser Glu Ala Val Ser Gln Leu Gln Asn Leu
    1475                1480                1485
Gln Glu Leu Leu Glu Thr Gln Thr Leu Arg Arg Gly Pro Gly Pro
    1490                1495                1500
Cys Arg His Ser Thr Ser Phe Pro Ile Leu Ser Pro Gly Glu Gly
    1505                1510                1515
Lys Lys Pro Met Ser Phe Cys Leu Phe Arg Trp Leu Lys Cys Ser
    1520                1525                1530
Cys Trp Leu Leu Leu Gly Val Ile Ser Leu Ala Ser Ala Phe Phe
    1535                1540                1545
Ile Thr Leu Tyr Ser Leu Glu Leu Asp Lys Asp Gln Ala Thr Ser
    1550                1555                1560
Trp Val Ile Ser Met Met Leu Ser Val Leu Gln Asp Ile Phe Ile
    1565                1570                1575
Ser Gln Pro Ile Lys Val Ile Phe Leu Thr Leu Leu Phe Ser Leu
    1580                1585                1590
Met Ala Asn His Met Pro Trp Leu Asn Lys Asp Lys Glu Gln His
    1595                1600                1605
Ala Arg Arg Ile Val Ala Leu Trp Ala Lys Cys Pro Trp Ser Ala
    1610                1615                1620
Pro Gly Leu Arg Asp Lys Asn Asn Pro Ile Tyr Thr Ala Pro Ala
    1625                1630                1635
Met Asn Asn Leu Ala Lys Pro Thr Arg Lys Ala Trp Lys Lys Gln
    1640                1645                1650
Leu Ser Lys Leu Thr Gly Gly Thr Leu Val Gln Ile Leu Phe Leu
    1655                1660                1665
Thr Leu Leu Met Thr Thr Val Tyr Ser Ala Lys Asp Ser Ser Arg
    1670                1675                1680
Phe Phe Leu His Arg Ala Ile Trp Lys Arg Phe Ser His Arg Phe
    1685                1690                1695
Ser Glu Ile Lys Thr Val Glu Asp Phe Tyr Pro Trp Ala Asn Gly
    1700                1705                1710
Thr Leu Leu Pro Asn Leu Tyr Gly Asp Tyr Arg Gly Phe Ile Thr
    1715                1720                1725
Asp Gly Asn Ser Phe Leu Leu Gly Asn Val Leu Ile Arg Gln Thr
    1730                1735                1740
Arg Ile Pro Asn Asp Ile Phe Phe Pro Gly Ser Leu His Lys Gln
    1745                1750                1755
```

-continued

```
Met Lys Ser Pro Pro Gln His Gln Glu Asp Arg Glu Asn Tyr Gly
    1760                1765                1770

Ala Gly Trp Val Pro Pro Asp Thr Asn Ile Thr Lys Val Asp Ser
    1775                1780                1785

Ile Trp His Tyr Gln Asn Gln Glu Ser Leu Gly Gly Tyr Pro Ile
    1790                1795                1800

Gln Gly Glu Leu Ala Thr Tyr Ser Gly Gly Tyr Val Val Arg
    1805                1810                1815

Leu Gly Arg Asn His Ser Ala Ala Thr Arg Val Leu Gln His Leu
    1820                1825                1830

Glu Gln Arg Arg Trp Leu Asp His Cys Thr Lys Ala Leu Phe Val
    1835                1840                1845

Glu Phe Thr Val Phe Asn Ala Asn Val Asn Leu Leu Cys Ala Val
    1850                1855                1860

Thr Leu Ile Leu Glu Ser Ser Gly Val Gly Thr Phe Leu Thr Ser
    1865                1870                1875

Leu Gln Leu Asp Ser Leu Thr Ser Leu Gln Ser Ser Glu Arg Gly
    1880                1885                1890

Phe Ala Trp Ile Val Ser Gln Val Val Tyr Tyr Leu Leu Val Cys
    1895                1900                1905

Tyr Tyr Ala Phe Ile Gln Gly Cys Arg Leu Lys Arg Gln Arg Leu
    1910                1915                1920

Ala Phe Phe Thr Arg Lys Arg Asn Leu Leu Asp Thr Ser Ile Val
    1925                1930                1935

Leu Ile Ser Phe Ser Ile Leu Gly Leu Ser Met Gln Ser Leu Ser
    1940                1945                1950

Leu Leu His Lys Lys Met Gln Gln Tyr His Cys Asp Arg Asp Arg
    1955                1960                1965

Phe Ile Ser Phe Tyr Glu Ala Leu Arg Val Asn Ser Ala Val Thr
    1970                1975                1980

His Leu Arg Gly Phe Leu Leu Leu Phe Ala Thr Val Arg Val Trp
    1985                1990                1995

Asp Leu Leu Arg His His Ala Gln Leu Gln Val Ile Asn Lys Thr
    2000                2005                2010

Leu Ser Lys Ala Trp Asp Glu Val Leu Gly Phe Ile Leu Ile Ile
    2015                2020                2025

Val Val Leu Leu Ser Ser Tyr Ala Met Thr Phe Asn Leu Leu Phe
    2030                2035                2040

Gly Trp Ser Ile Ser Asp Tyr Gln Ser Phe Phe Arg Ser Ile Val
    2045                2050                2055

Thr Val Val Gly Leu Leu Met Gly Thr Ser Lys His Lys Glu Val
    2060                2065                2070

Ile Ala Leu Tyr Pro Ile Leu Gly Ser Leu Leu Val Leu Ser Ser
    2075                2080                2085

Ile Ile Leu Met Gly Leu Val Ile Ile Asn Leu Phe Val Ser Ala
    2090                2095                2100

Ile Leu Ile Ala Phe Gly Lys Glu Arg Lys Ala Cys Glu Lys Glu
    2105                2110                2115

Ala Thr Leu Thr Asp Met Leu Leu Gln Lys Leu Ser Ser Leu Leu
    2120                2125                2130

Gly Ile Arg Leu His Gln Asn Pro Ser Glu Glu His Ala Asp Asn
    2135                2140                2145
```

```
Thr Gly Tyr
    2150

<210> SEQ ID NO 17
<211> LENGTH: 1732
<212> TYPE: PRT
<213> ORGANISM: Homo sapiens

<400> SEQUENCE: 17

Met Phe Phe Lys Gly Gly Ser Trp Leu Trp Leu Tyr Ile Arg Thr Ser
1               5                   10                  15

Ile Ile Leu Gly Ser Glu Leu Asn Ser Pro Ala Pro His Gly Gln Asn
            20                  25                  30

Asn Cys Tyr Gln Leu Asn Arg Phe Gln Cys Ser Phe Glu Glu Ala Gln
        35                  40                  45

His Tyr Cys His Val Gln Arg Gly Phe Leu Ala His Ile Trp Asn Lys
    50                  55                  60

Glu Val Gln Asp Leu Ile Arg Asp Tyr Leu Glu Gly Lys Lys Trp
65                  70                  75                  80

Trp Ile Gly Gln Asn Val Met Pro Leu Lys Lys His Gln Asp Asn Lys
                85                  90                  95

Tyr Pro Ala Asp Val Ala Ala Asn Gly Pro Pro Lys Pro Leu Ser Cys
            100                 105                 110

Thr Tyr Leu Ser Arg Asn Phe Ile Arg Ile Ser Ser Lys Gly Asp Lys
        115                 120                 125

Cys Leu Leu Lys Tyr Tyr Phe Ile Cys Gln Thr Gly Asp Phe Leu Asp
    130                 135                 140

Gly Asp Ala His Tyr Glu Arg Asn Gly Asn Asn Ser His Leu Tyr Gln
145                 150                 155                 160

Arg His Lys Lys Thr Lys Arg Gly Val Ala Ile Ala Arg Asp Lys Met
                165                 170                 175

Pro Pro Gly Pro Gly His Leu Pro Thr Thr Cys His Tyr Pro Leu Pro
            180                 185                 190

Ala His Leu Ser Lys Thr Leu Cys His Pro Ile Ser Gln Phe Pro Ser
        195                 200                 205

Val Leu Ser Ser Ile Thr Ser Gln Val Thr Ser Ala Ala Ser Glu Pro
    210                 215                 220

Ser Ser Gln Pro Leu Pro Val Ile Thr Gln Leu Thr Met Pro Val Ser
225                 230                 235                 240

Val Thr His Ala Gly Gln Ser Leu Ala Glu Thr Thr Ser Ser Pro Lys
                245                 250                 255

Glu Glu Gly His Pro Asn Thr Phe Thr Ser Tyr Leu Gln Val Ser Leu
            260                 265                 270

Gln Lys Ala Ser Gly Gln Val Ile Asp Glu Ile Ala Gly Asn Phe Ser
        275                 280                 285

Arg Ala Val His Gly Leu Gln Ala Leu Asn Lys Leu Gln Glu Ala Cys
    290                 295                 300

Glu Phe Leu Gln Lys Leu Thr Ala Leu Thr Pro Arg Phe Ser Lys Pro
305                 310                 315                 320

Ala Gln Val Asn Leu Ile Asn Ser Leu Ile Tyr Leu Ser Glu Glu Leu
                325                 330                 335

Leu Arg Ile Pro Phe Gln Asn Asn Asn Ser Leu Gly Phe Lys Val Pro
            340                 345                 350

Pro Thr Val Cys Pro Phe His Ser Leu Asn Asn Val Thr Lys Ala Gly
        355                 360                 365
```

```
Glu Gly Ser Trp Leu Glu Ser Lys Arg His Thr Glu Pro Val Glu Asp
    370                 375                 380

Ile Leu Glu Met Ser Leu Val Glu Phe Gly Asn Ile Gly Glu Ala Phe
385                 390                 395                 400

Leu Glu Gln Asn Gln Ser Pro Glu Ser Ser Val Thr Leu Thr Ser Ala
                405                 410                 415

Asn Ala Thr Leu Leu Ser Arg Gln Asn Ile Ser Thr Leu Pro Leu
                420                 425                 430

Ser Ser Tyr Thr Leu Gly His Pro Ala Pro Val Arg Leu Gly Phe Pro
            435                 440                 445

Ser Ala Leu Ala Leu Lys Glu Leu Leu Asn Lys His Pro Gly Val Asn
    450                 455                 460

Val Gln Ile Thr Gly Leu Ala Phe Asn Pro Phe Lys Asp Leu Asp Asn
465                 470                 475                 480

Arg Asn Ile Val Gly Ser Ile Gly Ser Val Leu Leu Ser Ala Asn Arg
                485                 490                 495

Lys Leu Leu Gln Val His Asp Leu Met Glu Asp Ile Glu Ile Met Leu
            500                 505                 510

Trp Arg Asn Val Ser Leu Glu Thr His Pro Thr Ser Leu Asn Met Ser
    515                 520                 525

Thr His Gln Leu Thr Ile Thr Val Asn Val Thr Ser Leu Glu Lys Ser
530                 535                 540

Leu Ile Val Ser Ile Asp Pro Asp Ser Pro Leu Leu Met Thr Leu Tyr
545                 550                 555                 560

Leu Gly Phe Gln Tyr Gln Pro Asn Cys Thr His Phe His Leu Asn Ile
            565                 570                 575

Thr Leu Pro Lys Asp Lys Val Trp Gln Lys Asp Glu Glu Tyr Thr Trp
            580                 585                 590

Val Leu Asn Pro Glu His Leu Gln His Gly Ile Gly Thr Tyr Tyr Ile
            595                 600                 605

Thr Ala Val Leu Ser Glu Arg Gln Glu Gly Ala Gln Gln Thr Pro Ser
    610                 615                 620

Leu Val Ser Val Ile Thr Ala Val Thr Gln Cys Tyr Tyr Trp Glu Ile
625                 630                 635                 640

His Asn Gln Thr Trp Ser Ser Ala Gly Cys Gln Val Gly Pro Gln Ser
                645                 650                 655

Thr Ile Leu Arg Thr Gln Cys Leu Cys Asn His Leu Thr Phe Phe Ala
            660                 665                 670

Ser Asp Phe Phe Val Val Pro Arg Thr Val Asn Val Glu Asp Thr Ile
            675                 680                 685

Lys Leu Phe Leu Arg Val Thr Asn Asn Pro Val Gly Val Ser Leu Leu
    690                 695                 700

Ala Ser Leu Leu Gly Phe Tyr Val Ile Thr Val Trp Ala Arg Lys
705                 710                 715                 720

Lys Asp Gln Ala Asp Met Gln Lys Val Lys Val Thr Val Leu Ala Asp
                725                 730                 735

Asn Asp Pro Ser Ala Gln Phe His Tyr Leu Ile Gln Val Tyr Thr Gly
                740                 745                 750

Tyr Arg Arg Ser Ala Ala Thr Thr Ala Lys Val Val Ile Thr Leu Tyr
            755                 760                 765

Gly Ser Glu Gly Arg Ser Glu Pro His His Leu Cys Asp Pro Gln Lys
770                 775                 780
```

-continued

```
Thr Val Phe Glu Arg Gly Gly Leu Asp Val Phe Leu Thr Thr Trp
785                 790                 795                 800

Thr Ser Leu Gly Asn Leu His Ser Leu Arg Leu Trp His Asp Asn Ser
        805                 810                 815

Gly Val Ser Pro Ser Trp Tyr Val Ser Gln Val Ile Val Cys Asp Met
            820                 825                 830

Ala Val Lys Arg Lys Trp His Phe Leu Cys Asn Cys Trp Leu Ala Val
                835                 840                 845

Asp Leu Gly Asp Cys Glu Leu Asp Arg Val Phe Ile Pro Val Ser Lys
    850                 855                 860

Arg Glu Leu Phe Ser Phe Arg His Leu Phe Ser Ser Met Ile Val Glu
865                 870                 875                 880

Lys Phe Thr Gln Asp Tyr Leu Trp Leu Ser Ile Ala Thr Arg His Pro
                885                 890                 895

Trp Asn Gln Phe Thr Arg Val Gln Arg Leu Ser Cys Cys Met Thr Leu
            900                 905                 910

Leu Leu Cys Asn Met Val Ile Asn Val Met Phe Trp Lys Ile Asn Ser
        915                 920                 925

Thr Thr Ala Lys Arg Asp Glu Gln Met Arg Pro Phe Ala Val Ala Trp
    930                 935                 940

Ser Glu Leu Leu Val Ser Ile His Thr Ala Val Ile Leu Phe Pro Ile
945                 950                 955                 960

Asn Leu Val Ile Gly Arg Leu Phe Pro Leu Ile Glu Pro Gln Glu Thr
                965                 970                 975

Leu Pro Leu Phe Pro Pro Ile Gln Ala Ser Cys Leu Ser Asp Ala Ser
            980                 985                 990

Val Glu Pro Leu Ser Ala Thr Met  Val Val Glu Glu Leu  Lys Glu Thr
            995                 1000                 1005

Val Arg  Phe Leu Leu Arg  Arg Asn Thr Tyr Leu Leu  Ser Lys Cys
    1010                 1015                 1020

Glu Gln  Pro Pro Trp Ser  Ser Trp Asp Ile Thr Lys  Leu Val Lys
    1025                 1030                 1035

Leu Leu  Ser Ser Leu Val Ser  Ser His Leu Glu Gly  Gln Gly Cys
    1040                 1045                 1050

His Gln  Gln Gly Glu Arg His  Trp Ala Arg Val Val  Pro Glu Asn
    1055                 1060                 1065

His His  His Phe Cys Cys Tyr  Leu His Arg Val Leu  Gln Arg Leu
    1070                 1075                 1080

Lys Ser  His Leu Gly Thr Leu  Gly Leu Thr Gln Gly  His Gln Ser
    1085                 1090                 1095

Cys Asp  Phe Leu Asp Ala Ala  Ser Gln Leu Gln Lys  Leu Gln Glu
    1100                 1105                 1110

Leu Leu  Glu Thr His Ile Leu  Pro Thr Glu Gln Glu  Pro Ser Arg
    1115                 1120                 1125

Glu Val  Thr Ser Phe Ala Ile  Leu Ser Ser Glu Glu  Gly Lys Lys
    1130                 1135                 1140

Pro Ile  Ser Asn Gly Leu Ser  Lys Trp Leu Thr Ser  Val Cys Trp
    1145                 1150                 1155

Leu Leu  Leu Gly Phe Thr Ser  Leu Ala Ser Ala Phe  Phe Thr Ala
    1160                 1165                 1170

Leu Tyr  Ser Leu Glu Leu Ser  Lys Asp Gln Ala Thr  Ser Trp Met
    1175                 1180                 1185

Ile Ser  Ile Ile Leu Ser Val  Leu Gln Asn Ile Phe  Ile Ser Gln
```

-continued

|     | 1190 |     |     | 1195 |     |     | 1200 |     |     |     |     |
|---|---|---|---|---|---|---|---|---|---|---|---|
| Pro | Val | Lys | Val | Phe | Phe | Thr | Phe | Leu | Tyr | Ser | Leu | Met | Met |
|     | 1205 |     |     | 1210 |     |     | 1215 |     |     |     |

Ser Arg Met Pro Arg Leu Asn Lys Glu Asn Glu Gln Gln Thr Lys
　　1220　　　　　　1225　　　　　　1230

Arg Ile Leu Ala Leu Leu Ala Lys Cys Ser Ser Val Pro Gly
　　1235　　　　　　1240　　　　　　1245

Ser Arg Asp Lys Asn Asn Pro Val Tyr Val Ala Pro Ala Ile Asn
　　1250　　　　　　1255　　　　　　1260

Ser Pro Thr Lys His Pro Glu Arg Thr Leu Lys Lys Lys Lys Leu
　　1265　　　　　　1270　　　　　　1275

Phe Lys Leu Thr Gly Asp Ile Leu Val Gln Ile Leu Phe Leu Thr
　　1280　　　　　　1285　　　　　　1290

Leu Leu Met Thr Ala Ile Tyr Ser Ala Lys Asn Ser Asn Arg Phe
　　1295　　　　　　1300　　　　　　1305

Tyr Leu His Gln Ala Ile Trp Lys Thr Phe Ser His Gln Phe Ser
　　1310　　　　　　1315　　　　　　1320

Glu Ile Lys Leu Leu Gln Asp Phe Tyr Pro Trp Ala Asn His Ile
　　1325　　　　　　1330　　　　　　1335

Leu Leu Pro Ser Leu Tyr Gly Asp Tyr Arg Gly Lys Asn Ala Val
　　1340　　　　　　1345　　　　　　1350

Leu Glu Pro Ser His Cys Lys Cys Gly Val Gln Leu Ile Phe Gln
　　1355　　　　　　1360　　　　　　1365

Ile Pro Arg Thr Lys Thr Tyr Glu Lys Val Asp Glu Gly Gln Leu
　　1370　　　　　　1375　　　　　　1380

Ala Phe Cys Asp Asn Gly His Thr Cys Gly Arg Pro Lys Ser Leu
　　1385　　　　　　1390　　　　　　1395

Phe Pro Gly Leu His Leu Arg Arg Phe Ser Tyr Ile Cys Ser Pro
　　1400　　　　　　1405　　　　　　1410

Arg Pro Met Val Leu Ile Pro Thr Asp Glu Leu His Glu Arg Leu
　　1415　　　　　　1420　　　　　　1425

Thr Ser Lys Asn Glu Asn Gly Phe Ser Tyr Ile Met Arg Gly Ala
　　1430　　　　　　1435　　　　　　1440

Phe Phe Thr Ser Leu Arg Leu Glu Ser Phe Thr Ser Leu Gln Met
　　1445　　　　　　1450　　　　　　1455

Ser Lys Lys Gly Cys Val Trp Ser Ile Ile Ser Gln Val Ile Tyr
　　1460　　　　　　1465　　　　　　1470

Tyr Leu Leu Val Cys Tyr Tyr Ala Phe Ile Gln Gly Cys Gln Leu
　　1475　　　　　　1480　　　　　　1485

Lys Gln Gln Lys Trp Arg Phe Phe Thr Gly Lys Arg Asn Ile Leu
　　1490　　　　　　1495　　　　　　1500

Asp Thr Ser Ile Ile Leu Ile Ser Phe Ile Leu Leu Gly Leu Asp
　　1505　　　　　　1510　　　　　　1515

Met Lys Ser Ile Ser Leu His Lys Lys Asn Met Ala Arg Tyr Arg
　　1520　　　　　　1525　　　　　　1530

Asp Asp Gln Asp Arg Phe Ile Ser Phe Tyr Glu Ala Val Lys Val
　　1535　　　　　　1540　　　　　　1545

Asn Ser Ala Ala Thr His Leu Val Gly Phe Pro Val Leu Leu Ala
　　1550　　　　　　1555　　　　　　1560

Thr Val Gln Leu Trp Asn Leu Leu Arg His Ser Pro Arg Leu Arg
　　1565　　　　　　1570　　　　　　1575

Val Ile Ser Arg Thr Leu Ser Arg Ala Trp Asp Glu Val Val Gly
　　1580　　　　　　1585　　　　　　1590

-continued

```
Phe Leu Leu Ile Ile Leu Ile Leu Leu Thr Gly Tyr Ala Ile Ala
    1595                1600               1605

Phe Asn Leu Leu Phe Gly Cys Ser Ile Ser Asp Tyr Arg Thr Phe
    1610                1615               1620

Phe Ser Ser Ala Val Thr Val Val Gly Leu Leu Met Gly Ile Ser
    1625                1630               1635

His Gln Glu Glu Val Phe Ala Leu Asp Pro Val Leu Gly Thr Phe
    1640                1645               1650

Leu Ile Leu Thr Ser Val Ile Leu Met Val Leu Val Val Ile Asn
    1655                1660               1665

Leu Phe Val Ser Ala Ile Leu Met Ala Phe Gly Lys Glu Arg Lys
    1670                1675               1680

Ser Leu Lys Lys Glu Ala Ala Leu Ile Asp Thr Leu Leu Gln Lys
    1685                1690               1695

Leu Ser Asn Leu Leu Gly Ile Ser Trp Pro Gln Lys Thr Ser Ser
    1700                1705               1710

Glu Gln Ala Ala Thr Thr Ala Val Gly Ser Asp Thr Glu Val Leu
    1715                1720               1725

Asp Glu Leu Pro
    1730

<210> SEQ ID NO 18
<211> LENGTH: 19
<212> TYPE: PRT
<213> ORGANISM: Mus musculus

<400> SEQUENCE: 18

Lys Leu Lys Met Leu Glu Arg Lys Gly Glu Leu Ala Pro Ser Pro Gly
1               5                   10                  15

Met Gly Glu

<210> SEQ ID NO 19
<211> LENGTH: 19
<212> TYPE: PRT
<213> ORGANISM: Mus musculus

<400> SEQUENCE: 19

Asp Phe Gln Glu Ala Asp Asn Tyr Cys His Ala Gln Arg Gly Arg Leu
1               5                   10                  15

Ala His Thr
```

MAMMALIAN SOUR/ACID TASTE AND CSF RECEPTOR GENES, POLYPEPTIDES AND ASSAYS

CROSS REFERENCE TO RELATED APPLICATIONS

This application is a continuation-in-part of U.S. Ser. No. 11/176,958 to Zuker and Huang, entitled "A NOVEL ION CHANNEL PREFERENTIALLY EXPRESSED IN MAMMALIAN TASTE RECEPTOR CELLS," filed Jul. 6, 2005. This application is also related to U.S. Ser. No. 60/741,352 to Zuker and Huang entitled "TASTE RECEPTOR GENES AND PROTEINS," filed Nov. 30, 2005. The subject application claims priority to and benefit of each of these prior applications, each of which are incorporated herein by reference in their entirety.

STATEMENT OF GOVERNMENT SUPPORT

This Invention was made with government support under grant NIH R01 DC04861 awarded by the National Institute of Health. The United States government has certain rights in the invention.

FIELD OF THE INVENTION

The invention includes the surprising discovery that polycystin-2L1 is a taste receptor protein of the mammalian sour (acid) taste receptor system. Polycystin-2L1 is also expressed in neurons surrounding the central canal of the spinal cord and brain stem and is involved in the cerebro-spinal fluid (CSF) chemosensory system. Polycystin-2L1 is a transmembrane ion channel protein encoded by the gene PKD2L1. PKD1L3 is co-expressed with PKD2L1 in cells of the CV and foliate papillae and polycystin-1L3 may be a functional partner of Polycystin-2L1.

BACKGROUND OF THE INVENTION

Taste transduction is one of the most sophisticated forms of chemotransduction in animals (Avenet and Lindemann, 1989; Margolskee, 1993; Lindemann, *Physiol. Rev.* 76:718-766, 1996; Kinnamon et al., *Annu. Rev. Physiol.* 54:715-731, 1992; and Gilbertson et al., *Curr. Opin. Neurobiol.* 10: 519-527, 2000). Gustatory signaling is found throughout the animal kingdom, from simple metazoans to the most complex of vertebrates; its main purpose is to provide a reliable signaling response to non-volatile ligands.

Mammals are believed to have five basic types of taste modalities: salty, sour (acid), sweet, umami (the taste of MSG), and bitter. Each of these is thought to be mediated by distinct signaling pathways leading to receptor cell depolarization, generation of a receptor or action potential and release of neurotransmitter and synaptic activity (Roper, (1989) *Ann. Rev. Neurosci.* 12:329-353).

In general, the identification of new taste receptors is highly desirable. The identification of a taste receptor provides methods and systems for screening for new tastants, such as the identification of new artificial tastants (sweeteners, sour flavors, salt substitutes, etc.) and for the identification of activity modulators that produce a greater receptor response to specified amounts of a tastant. For example, the use of sour or other flavor enhancers may be useful in reducing the amount of sour or other flavoring needed to provoke, enhance, reduce or eliminate a sour receptor taste cell response, which may thus be useful as a flavor modulator. Similarly, acid is used as a preservative; the ability to reduce the flavor impact of such preservatives can be useful in food storage and packaging applications.

Relatively recently, the receptors for bitter, sweet and umami were cloned and shown to be encoded by two families of G-protein coupled receptors (Nelson et al., 2000; Nelson et al., 2001; Zhang et al., 2003; Zhao et al., 2003; Mueller et al., 2005). In contrast, most of the molecular components of the sour and salty pathways are previously unknown. Electrophysiological studies suggested that sour and salty tastants may modulate taste cell function by direct entry of $H^+$ and $Na^+$ ions through specialized membrane channels on the apical surface of the cell. Thus, ion channels selectively expressed in taste receptor cells could be candidates for mediators of salt and sour tastes. Alternatively, ion channels can function as a final critical signaling component in the activation of taste cells (akin to the role of TRPM5 in sweet, umami and bitter cells; Zhang et al., 2003).

Many other families of cell receptors are also known to function in a variety of signal transduction events associated with cell sensation. For example, the polycystins (e.g., polycystin-1, or "PC-1" and polycystin-2, or "PC-2," encoded by PKD1 and PKD2, respectively) are integral membrane proteins with large extracellular N termini that are thought to possess a number of functions, including mechanosensation in renal and nodal cilia (reviewed in Nauli and Zhou 2004 "Polycystins and Mechanosensation in renal and nodal cilia" *Bioessays* 26.8 844-856 *Wiley Periodicals*). The polycystins fall into two basic classes of proteins, the PC-1-like proteins, which are receptor-like molecules and the PC-2-like proteins, which are ion channels (these proteins can also collectively form ion channel pore complexes). Several studies have found overlapping and interdependent roles for these proteins in various systems, particularly in kidney cells. Mutations in various of these genes cause polycystic kidney disease.

SUMMARY OF THE INVENTION

The invention includes the surprising discovery that the PC-2-like protein polycystin-2L1 (PC-2-L1), encoded by PKD2L1, is a sour/acid taste receptor protein and also functions as a pH sensor in neurons in contact with the cerebrospinal fluid (CSF). Previously, the function of this protein was unassigned, but was expected to be primarily involved in kidney function. The surprising discovery of a significant role for PKD2L1 in chemosensation, both in the taste system and in the CSF, provides assays for the identification and isolation of polycystin-2L1 activity modulators, e.g., in taste sensation and pH sensing in the CSF. It also provides a functional platform for taste- or pH related behavioral or physiological effects mediated by polycystin-2L1. Polycystin-3L1 ("PC-1-L3," encoded by PKD1L3) has also been found to be a likely partner for polycystin-2L1 in some, though not all tissues expressing PKD2L1. Accordingly, assays of the invention can also identify tastant and activity modulators, etc., of PC-1-L3. The discovery that PKD1L3 may have a role in chemosensation is also surprising. The surprising discovery that PC-1-L3 and PC-2-L1 are specifically co-expressed in certain taste receptor cells, suggesting that they form taste receptor protein complexes (e.g., including PC-1-L3 and/or PC-2-L1) in those cells (e.g., in the form of receptors and/or ion channels and/or receptor/channel complexes) provides receptor targets for tastant and activity modulator identification and for studies on any taste-related behavioral effects mediated by either of these proteins, separately, and/or in combination.

Assays of the invention can be cell or tissue based, e.g., screening of natural or transgenic cells, or transfected cells or tissues expressing PKD2L1 for receptor activity in response to test compounds, or can be based on behavioral or physiological whole animal studies. For animals studies, transgenic non-human animals (e.g., mice) can be produced, including PKD2L1 and/or PKD1L3 knock-outs and transgenic animals comprising heterologous PKD2L1 and/or PKD1L3 genes, e.g., to facilitate behavioral and tastant studies for a PKD2L1 or PKD1L3 gene of interest. For example, a PKD2L1 and/or PKD1L3 knock-out mouse can be made transgenic with the PKD2L1 and/or PKD1L3 gene from a human, and the resulting transgenic mouse can be used to study responses to putative human polycystin-2L1 and/or polycystin-1L3 tastants and/or activity (e.g., pH sensing) modulators. In addition, the invention provides for the identification of taste and pH receptor defects at a molecular level (e.g., thorough detection of PKD1L3 and/or PKD2L1 polymorphisms) and for the correction of these defects by gene therapy or pharmacological. Corresponding systems and kits are also included. Further details regarding these and other features of the invention are found herein.

Accordingly, in one aspect, methods of screening a test compound, such as a putative tastant or modulator of an activity of polycystin-2L1 and/or polycystin-1L3 polypeptides, or polypeptide complexes are provided. In the methods, a compound that binds to or modulates an activity of a polycystin-2L1 and/or polycystin-1L3 taste (e.g., acid or sour tastant sensing), CSF pH or other receptor or sensor system polypeptide or polypeptide complex is provided. A biological or biochemical sample comprising the polypeptide or complex is contacted with a test compound and binding of the test compound to the polypeptide or complex, or modulation of the activity of the polypeptide or complex by the test compound is detected. This identifies whether the compound binds to or modulates the activity of the polypeptide or polypeptide complex.

Related methods of modulating an activity of a cell expressing a polycystin-2L1 or polycystin 1L3 polypeptide or complex, are also a feature of the invention. These methods include contacting the cell with a compound that binds to or modulates an activity of the polycystin-2L1 polypeptide, e.g., as identified herein. In addition to modulating activity, such compounds can be used for labeling the cell to detect PC-2-L1, PC-1-L3, PKD1L2 and/or PKD2L1, e.g., using in situ hybridization experiments. Examples of modulators/labels include antibodies against the polypeptide or complex and nucleic acids that hybridize to PKD1L3 or PKD2L1 (including probes, anti-sense RNAs, SiRNAs, MiRNAs, tncRNAs, smRNAs, and/or other probes or DNA or RNA interference moieties).

Typically, the methods herein can be used in a high throughput fashion to screen one or more biological sample comprising one or more polycystin-2L1 and/or polycystin-1L3 taste receptor polypeptide(s) with a plurality of test compounds. Binding of the test compounds to the polycystin-2L1 and/or polycystin-1L3 receptor polypeptide(s)/complex, or modulation of the activity of the polypeptide(s)/complex by the test compounds is detected, e.g., in a high throughput screen, thereby identifying compounds that bind to or modulate the activity of polypeptide(s). The polypeptide(s) can include taste receptor polypeptides, CSF pH sensing receptor polypeptides, and/or the like.

For these methods, the biological sample can be moved into contact with the test compound, or vice versa, depending on the format of the method that is selected. For example, either the test compound or the polypeptide can be fixed in position, e.g., in a solid phase or liquid phase array, and the appropriate polypeptide or test compound can be contacted to the fixed component. Alternately, both polypeptide and test compound can be in a mobile phase, e.g., in a microfluidic device. Thus, "contacting" in these methods refers to the polypeptide and test compound being brought into contact with each other, regardless of which component is moved to achieve contact of the relevant components.

Regardless of assay format, one or more biological sample comprising one or more PC-1-L2, PC-1-L3 or PC-2-L1/PC-1-L3 polypeptide or complex can be contacted with a plurality of test compounds. Binding of the test compounds to the polypeptide or complex, or modulation of the activity of the polypeptide by the test compounds can then be detected, thereby identifying one or more compound that binds to or modulates the activity of the polypeptide or complex. High throughput cell or in vitro formats that achieve testing of 100, 1,000, 10,000 or more test compounds per hour can be used, as can lower throughput formats, such as in vivo assays using heterologous mice. Test compounds can be pre-screened for any desired property, including toxicity, bio-distribution, oral availability, or the like.

The test compounds can be from a pre-screened library, e.g., of compounds prescreened for any property of interest (toxicity, ingestibility, three dimensional chemical structure, type of molecule (ion, acid, sour tastant, natural product, etc.)). For example, the test compounds can be, e.g., selected from libraries of naturally occurring compounds, ions, salt substitutes, tastants, small organic molecules, peptides, peptide mimetics, weak acids, strong acids, CO, $CO_2$, acetic acid, a specific blocker of carbonic anhydrase, MK-417, an ion channel agonist, an ion channel antagonist, an ion channel enhancer, a non-specific $Ca^+$ channel blocker, Nifedipine and/or structurally related compounds, V1erapamil and/or structurally related compounds, gadolinium and/or structurally related compounds, and/or a stretch-induced channel blocker, or the like. Whether identified from a pre-screened or random collection of compounds, any compound that is identified as having a desired activity in any screen herein can be modified to reduce toxicity, enhance activity, or the like. In one preferred embodiment, the test compound enhances an activity of the PC-1-L3 or PC-2-L1 polypeptide or complex, e.g., by potentiating an activity of the polypeptide or complex. In another preferred aspect, the test compound inhibits or blocks an activity of the polypeptide or complex.

The precise activity of the test compound with respect to polycystin-2L1 and/or polycystin-1L3 can vary. In one embodiment, the test compound enhances an activity of the polycystin-2L1 and/or polycystin-1L3 polypeptide or complex. Alternately, the test compound can potentiate an activity of the polycystin-2L1 and/or polycystin-1L3 polypeptide or complex. The test compound can inhibit or block an activity of the polycystin-2L1 and/or polycystin-1L3 polypeptide.

For any assay herein, suitable sources of polycystin-2L1 and/or polycystin-1L3 are available, e.g., human, rat, dog or murine polycystin-2L1 taste receptor polypeptides and available PC-1-L3 polypeptides (or PKD2L1 and/or PKD1L3 genes that encode such polypeptides).

In addition, transgenic livestock or domesticated animals can be made recombinant for a given polycystin-2L1 and/or polycystin-1L3 polypeptide, or a modified form thereof, thereby changing the feeding behavior of the transgenic animal, e.g., to enhance yield of a domesticated or livestock animal.

In a preferred embodiment, the assay methods of the invention are cell-based, or use preparations of cellular materials. In these embodiments, the biological sample comprises or is derived from a cell that expresses the polycystin-2L1 and/or polycystin-1L3 polypeptide(s)/complexes. Most typically, such cells are provided by expressing a PKD2L1 and/or PKD1L3 gene naturally or in a recombinant cell. The PKD2L1 and/or PKD1L3 gene may be, though is not necessarily, heterologous to the recombinant cell.

The cell in these methods is typically selected for ease of manipulation and convenience of the practitioner and can be, e.g., a human, rodent, *Xenopus* or insect cell, and can be a cell in culture or a primary cell. The cell can also be, e.g., a taste bud cell, a cell (e.g., a neuronal cell) that is in contact with CSF, or can be, e.g., a kidney cell, or can be derived from any of these cells, e.g., where receptor activity is to be studied in a cellular context similar to one in which the receptor is expressed in vivo. Typically, however, the cell can be any cell typically used in culture, e.g., a mammalian cell (e.g., CHO), an insect cell (e.g., Snyder or KT), a *Xenopus* oocyte, or the like.

In the methods, whether a cell based or cell free format is used, binding can be detected between the polycystin-2L1 and/or polycystin-1L3 taste receptor polypeptide and a test compound moiety such as a potentiator of the polycystin-2L1 and/or polycystin-1 L3 receptor polypeptide, an antagonist of the polycystin-2L1 and/or polycystin-1 L3 receptor polypeptide, an agonist of the polycystin-2L1 and/or polycystin-1L3 receptor polypeptide, an inverse agonist of the polycystin-2L1 and/or polycystin-1L3 receptor polypeptide, a ligand that specifically binds to the polycystin-2L1 and/or polycystin-1L3 receptor polypeptide, and/or an antibody that specifically binds to the polycystin-2L1 and/or polycystin-1 L3 receptor polypeptide.

In general, detection of polycystin-2L1 and/or polycystin-1L3 binding to or activity modulation by the test compound can be performed in vitro, in situ or in vivo. Typically, a signal resulting from the binding or activity of the polycystin-2L1 and/or polycystin-1L3 receptor polypeptide is detected. Such signals that can be detected include polycystin-2L1 and/or polycystin-1L3 conformation-dependent signals, e.g., where a conformation of the polycystin-2L1 and/or polycystin-1L3 receptor polypeptide or complex is modified by binding of the test compound to the polycystin-2L1 and/or polycystin-1L3 receptor polypeptide or complex, or wherein formation of a polycystin-2L1 and/or polycystin-1 L3 complex is detected. Other detection modalities that can be used include detecting one or more of: $H^+$ flux, $Na^+$ flux, $Ca^{2+}$ flux, ion flux, depolarization of a cell, cell membrane voltage changes, cell membrane conductivity changes, a kinase activity triggered upon binding of a compound to the polypeptide or complex, generation, breakdown or binding of a phorbol ester by the polypeptide or complex, binding of diacylglycerol or other lipids by the polypeptide or complex, cAMP activity of the polypeptide or complex, cGMP activity of the polypeptide or complex, GTPgammaS binding by the polypeptide or complex, phospholipase C activity induced by the polypeptide or complex, activity of an enzyme involved in cellular ionic balance, binding of polycystin-2L1 and/or polycystin-1L3 polypeptides to each other or to another PC-1 like or PC-2 like protein (including other PC-1 or PC-2 proteins), formation of homo or heterodimers, e.g., with other polycystin proteins (including, e.g., between polycystin-2L1 and polycystin-1L3), or monitoring a transcriptional reporter activity.

In one optional aspect, the polycystin-2L1 and/or polycystin-1L3 polypeptide can be incorporated into a biosensor, e.g., for detection of compounds that activate or bind to the polycystin-2L1 and/or polycystin-1L3 polypeptide. This can be used as a component of an artificial device, e.g., for chemodetection. For example, in one implementation, the biosensor comprises a Chem-FET operably coupled to the polycystin-2L1 and/or polycystin-1L3 receptor polypeptide or to a complex thereof.

As in the methods discussed herein, the invention also provides compositions comprising recombinant cells that includes a heterologous PKD1-L3 gene and/or a heterologous PKD2-L1 gene or genes. As in other aspects herein, the cell can be, e.g., a human, rodent or insect cell. The cell can be a clinically relevant target, e.g., a neuronal cell, a kidney cell, or a taste receptor cell, or can be a cell that is easy to culture or manipulate in vitro. Any of the various permutations of these genes noted herein optionally apply to this embodiment as well, e.g., wherein the PKD1-L3 gene or the PKD2-L1 gene are human, murine, or the like e.g., wherein the genes are heterologous to the recombinant cell. In one example, the PKD1-L3 and the PKD2-L1 genes are expressed in the recombinant cell and a PC-2-L1/PC-1-L3 complex is formed in the cell, or in or on a membrane of the cell.

Similarly, in a related aspect, the invention provides an isolated or recombinant polypeptide complex that includes at least one of: a recombinant PC-1-L3 polypeptide and/or a recombinant PC-2-L1 polypeptide. Typically, the complex further includes at least one of: a PC-1-L3 polypeptide, a PC-2-L1 polypeptide, a recombinant PC-1-L3 polypeptide and/or a recombinant PC-2-L1 polypeptide. For example, in one embodiment, an isolated or recombinant polypeptide complex of the invention includes recombinant human PC-1-L3 polypeptide and a recombinant human PC-2-L1 polypeptide. The isolated or recombinant polypeptide can be (and typically is) expressed in one or more recombinant cell(s).

Systems for practicing the methods herein are also a feature of the invention. For example, systems for detecting compounds that bind to or modulate an activity of a polycystin-2L1 or polycystin-1L3 polypeptide or complex are provided. In one implementation, the system includes a biological sample comprising the polypeptide or complex and a source of a plurality of test compounds. Typically, the system further includes a detector that detects binding of one or more of the test compounds (tastants, putative modulators of taste sensation or CNS pH sensor activity, etc.) to the polycystin-2L1 and/or polycystin-1L3 receptor polypeptide or complex, or modulation of the activity of the polypeptide by one or more of the test compounds, thereby identifying a putative compound that binds to or modulates the activity of the polycystin-2L1 and/or polycystin-1L3 receptor polypeptide or complex.

Features noted above for the method claims are applicable here as well, e.g., use of various cells or cell components to provide or constitute the biological sample, e.g., a cell comprising a heterologous gene encoding the polycystin-2L1 and/or polycystin-1L3 polypeptide or complex. Example cells include mammalian cells, insect cells, *Xenopus* cells, taste receptor cells, cells in contact with the CSF, kidney cells, and/or the like. Similarly as above, the modulator can include any activity modulating compound, e.g., an agonist, enhancer, antagonist, or inverse agonist.

The source of biological samples, genes, test compounds, etc., can be any of those noted above or herein with respect to methods of the invention. For example, in one aspect, the test compounds include a library of tastant compounds. This library can be of, e.g., compounds of interest, and can, optionally, be pre-screened or pre-selected for any desirable property (structure, binding to a PC protein, bioavailability, toxicity, etc.). Thus, for example, the source of test compounds optionally comprises a library of potential sour tastant compounds, e.g., any of those already noted, e.g., of small molecules that cover a large amount of chemical diversity, a library natural compounds, a library of peptides or peptidomimetics, a library pre-screened for compounds of a given activity or structure, etc. The format of the source can be, e.g., a multi-well plate, a microfluidic device, a solid phase array, or the like.

The detector can employ any available detection system, e.g., can be a patch clamp device, an optical detection device, or the like. For example, the detector can include a fluorescence detector that detects FRET, changes in membrane potential or flow of a dye into or out of the cell, or the like. Patch clamping, FRET based sensors, transmembrane flow of ion sensitive dyes, expression in oocytes and voltage clamping are all useful embodiments.

In another aspect, methods of detecting a behavior (e.g., a taste-induced behavior) or a physiological response (e.g., a response dependent on pH of the CSF) modulated by a polycystin-2L1 and/or polycystin-1L3 polypeptide are provided. The methods include introducing a heterologous PKD2L1 and/or PKD1L3 gene into an animal and expressing an encoded heterologous polycystin-2L1 and/or polycystin-1L3 taste receptor polypeptide in a taste bud of the animal or in a cell of the animal in contact with the CSF. A putative polycystin-2L1 and/or polycystin-1L3 tastant or modulator of the polypeptide is provided to the animal, and a feeding behavior or physiological response of the animal is monitored in response to the presence of the putative polycystin-2L1 taste receptor tastant or modulator. For example, feeding behavior or respiration rate can be monitored.

Optionally, the gene includes a native or heterologous promoter that is active in the taste bud or in neurons proximal to the CSF of the animal (or both). Examples of heterologous promoters include a PKD2L1 promoter, a PKD1L3 promoter, a T1R-gene promoter, T2R-gene promoter, TRPM5- gene promoter, a PLCB2 gene promoter, a repeater gene promoter, a gustducin gene promoter, a Gi2 gene promoter, a cytokeratin-19 gene promoter, a promoter for a gene that is naturally selectively expressed in a taste receptor cell of the tongue or palate epithelium, or a known promoter of a gene promiscuously expressed in central or peripheral neurons (e.g., as described in Gray PA Fu H et al (2004). "Mouse Brain Organization Revealed through Direct Genome Scale Transcription Factor Expression Analysis." *Science* 306, 2255-57).

Optionally, the animal is a mouse or other commonly used laboratory animal (rat, rabbit, etc.) and the heterologous gene is a human PKD2L1 or PKD1L3 gene. The animal optionally is a knock out animal for an endogenous PKD2L1 or PKD1L3 taste receptor gene. The recombinant (e.g., transgenic) animal thus optionally provides the human PKD2L1 and/or PKD1L3 taste receptor gene in an animal model, providing one of skill with a model system for detecting the behavioral influence of test compounds on the human polypeptides/complexes in an established animal model.

Many formats for detecting, e.g., taste-induced behavior modulated by PC-2-L1 and/or PC-1-L3 receptor polypeptides and/or complexes are provided. In one example format, a putative tastant or modulator is provided on a licking or feeding device (licking stick, solution with the tastant or modulator, food with the tastant of modulator, etc.) to the animal and licking or feeding behavior of the animal on the device is monitored. Typically, in this or other formats testing for taste induced behaviors, the putative tastant or modulator is provided to the animal in conjunction with a control compound and the relative frequency of feeding behavior between the putative tastant and the control compound is determined.

In an alternate embodiment, the modulator is fed to the animal, or is injected into the animal when a physiological response is to be monitored. For example, a modulatory effect on pH sensing in the CSF can be monitored. In this embodiment, a physiological response to the putative modulator (test compound), such as an effect on respiration response to CSF pH, is monitored after administration of the test compound.

Observations of behavioral or physiological responses can be adjusted for various controls, or compared to behavior changes or physiological responses induced by known tastants or modulators. For example, the putative tastant or modulator can be provided to the animal in conjunction with a control compound and the relative frequency of feeding behavior caused by the putative tastant can be compared to the control compound.

Any of the various tastants or modulators noted above or herein can be applied to these methods as well, e.g., the taste receptor tastant or modulator can include an agonist, enhancer, antagonist, or inverse agonist of a PC-2-L1 or PC-1-L3 polypeptide or polypeptide complex.

Systems for practicing the methods are also a feature of the invention. For example, the system can include a non-human animal comprising a heterologous PKD2L1 and/or PKD1L3 receptor gene that is expressed in a taste bud of the animal, or in the CSF or kidney of the animal. The system can further include a source of a putative tastant or modulator that is accessible or deliverable to the animal and a detector that detects a behavior or physiological response of the animal in response to the presence of the putative tastant or modulator. Optionally, the system further includes an analysis module operably linked to the detector, e.g., an analysis module (e.g., software in a computer) that analyzes information received from the detector.

The detector optionally comprises a camera that detects movement by the animal. In an alternate aspect, the detector includes a device that monitors respiration rate and/or oxygen consumption by the animal. An analysis module operably linked to the detector analyzes information received from the detector.

In yet another aspect, the invention includes a recombinant taste bud cell comprising a heterologous PKD2L1 taste receptor gene, or a heterologous polycystin-2L1 taste receptor polypeptide. Typically, the taste bud cell is in culture, or is present in a recombinant non-human animal.

Similarly, a knock out non-human animal (e.g., a mouse) comprising a defect in a native PKD2L1 or PKD1L3 gene or in native gene expression is a feature of the invention. Optionally, the animal comprises a heterologous PKD2L1 or PKD1L3 gene (e.g., a human PKD2L1 or PKD1L3 gene) that is expressed in the taste-bud or in cells in contact with the CSF of the animal. Thus, for example, the animal can be a knock-out or double-knock out mouse deficient in endogenous PC-2-L1 and/or PC-1-L3 taste receptor polypeptide expression, e.g., a mouse that expresses a heterologous human PC-1-L3 taste receptor polypeptide and/or a heterologous human polycystin 2-L1 polypeptide.

Another related feature of the invention is a non-human animal comprising a cell ablation corresponding to cells that naturally express PKD2L1 or PKD1L3 in taste buds or in cells in contact with CSF of the animal.

Methods of detecting a molecular basis for a taste or CSF receptor function abnormality are also provided. For example, the abnormality can take the form of reduced responsiveness to a receptor stimulus. The methods include determining whether a biological sample from a patient comprises a polymorphism in a gene encoding polycystin-2L1 or an abnormality in expression of polycystin-2L1, and/or in a gene encoding polycystin-1L3 or an abnormality in expression of polycystin-1L3. The polymorphism (e.g., a single nucleotide polymorphism (SNP), a rearrangement, a splicing variant, an expression variant, or the like) is then correlated with an abnormality in taste receptor function, thereby determining whether the patient has a genetic basis for a taste receptor function abnormality. Polymorphisms that include or result in an abnormality in expression of polycystin-2L1 or polycystin-1L3 can include, e.g., an abnormal form or abnormal tissue distribution of polycystin-2L1 or polycystin-1L3 mRNA or protein.

In another aspect, a method of rescuing a taste bud or CSF contacting cell that has altered or missing polycystin-2L1 or polycystin-1L3 taste or CSF receptor function is provided. The method includes introducing a nucleic acid encoding the recombinant polypeptide homologous to polycystin-2L1 or polycystin-1L3 into the cell, and expressing the recombinant polypeptide, thereby providing polycystin-2L1 or polycystin-1L3 function to the cell. The cell can be in cell culture, in a tissue, in a taste bud, in a cell in contact with CSF, in a mammal, etc.

In an additional aspect, the invention provides an antibody that binds to a polycystin-2L1 or polycystin-3L1 polypeptide when expressed in a taste bud or in a cell in contact with the CSF. Optionally, the antibody modulates (e.g., enhances or inhibits) an activity of the polypeptide.

Kits for practicing the above methods are also a feature of the invention. The kits can include, e.g., a PKD2L1 or PKD1L3 nucleic acid, e.g., a vector comprising a PKD2L1 or PKD1L3 gene, a polycystin-2L1 or polycystin-1L3 polypeptide, recombinant cells expressing the genes or polypeptides, transgenic animals, etc., as noted above. The kits can further include instructions for using the other kit components to practice the methods herein, system components, packaging materials for packaging the components noted above, etc.

BRIEF DESCRIPTION OF THE FIGURES

FIG. 2A-2B provide an alignments of sequences for human, rat, and mouse PKD2L1 (SEQ ID NOs:14, 12, and 13, respectively) and clone ID529 (SEQ ID NO:2).

FIG. 4 is an alignment of rat, mouse, and human PKD1L3 sequences (SEQ ID NOs:15, 16, and 17, respectively).

FIG. 7A-C shows a diagram of the central canal, a labeled photomicrograph and a series of traces showing pH responses of PKD2L1-expressing cells surrounding the central canal.

FIG. 8, panels A and B show in situ hybridization images.

DEFINITIONS

Figure 1:
FIG. 1 shows results from the RNA in situ hybridization in circumvallate taste papillae.

Before describing the present invention in detail, it is to be understood that this invention is not limited to particular technical or biological systems or components, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "polycystin-2L1 polypeptide" or a polycystin-2L1 receptor polypeptide is a polypeptide that is the same as, a splice-variant of, or homologous to a human polycystin-2L1 or murine polycystin-2L1, or that is derived from such a polypeptide (e.g., through cloning, recombination, mutation, or the like). The polypeptide can be full length or can be a fragment of a full length protein. A polycystin-2L1 fragment typically includes at least 10 contiguous amino acids corresponding to a native polycystin-2L1 protein, such as a human murine, dog or rat polycystin-2L1. The polycystin-2L1 receptor polypeptide can be naturally occurring or recombinant, and can be unpurified, purified, or isolated, and can exist, e.g., in vitro, in vivo, or in situ. In one typical useful embodiment, the polycystin-2L1 receptor polypeptide is a transmembrane protein. As described herein, in useful embodiments, the polycystin-2L1 receptor polypeptide can be a sour/acid receptor, in any of a variety of contexts, including as a taste receptor polypeptide, as a CSF receptor polypeptide or as an acid receptor in other systems, e.g., in the kidney.

A "polycystin-2L1 taste receptor polypeptide" is a polypeptide that is the same as, a splice-variant of, or homologous to a human polycystin-2L1 or murine polycystin-2L1 and that is expressed in taste receptor cells, or that is derived from such a polypeptide that is expressed in such taste receptor cells (e.g., through cloning, recombination, mutation, or the like). The polypeptide can be full length or can be a fragment of a full length protein. A polycystin-2L1 fragment typically includes at least 10 contiguous amino acids corresponding to a native polycystin-2L1 protein, such as a human murine, dog or rat polycystin-2L1. The polycystin-2L1 taste receptor polypeptide can be naturally occurring or recombinant, and can be unpurified, purified, or isolated, and can exist, e.g., in vitro, in vivo, or in situ. In one typical useful embodiment, the polycystin-2L1 taste receptor polypeptide is a transmembrane protein.

A "polycystin-2L1 CSF receptor polypeptide" is a polypeptide that is the same as, a splice-variant of, or homologous to a human polycystin-2L1 or murine polycystin-2L1 and that is expressed in cells that are in contact with the CSF, or that is derived from such a polypeptide that is expressed in such CSF-contacting cells (e.g., through cloning, recombination, mutation, or the like). The polypeptide can be full length or can be a fragment of a full length protein. A polycystin-2L1 fragment typically includes at least 10 contiguous amino acids corresponding to a native polycystin-2L1 protein, such as a human murine, dog or rat polycystin-2L1. The polycystin-2L1 taste receptor polypeptide can be naturally occurring or recombinant, and can be unpurified, purified, or isolated, and can exist, e.g., in vitro, in vivo, or in situ. In one typical useful embodiment, the polycystin-2L1 taste receptor polypeptide is a transmembrane protein.

A "polycystin-1L3 polypeptide" or "polycystin-1L3 receptor polypeptide" is a polypeptide that is the same as, a splice-variant of, or homologous to a human polycystin-1L3 or murine polycystin-1L3, or that is derived from such a polypeptide (e.g., through cloning, recombination, mutation, or the like). The polypeptide can be full length or can be a fragment of a full length protein. A polycystin-1L3 fragment typically includes at least 10 contiguous amino acids corresponding to a native polycystin-1L3 protein, such as a human murine, dog or rat polycystin-1L3. The polycystin-1L3 receptor polypeptide can be naturally occurring or recombinant, and can be unpurified, purified, or isolated, and can exist, e.g., in vitro, in vivo, or in situ. In one typical useful embodiment, the polycystin-1L3 receptor polypeptide is a transmembrane protein. As described herein, in useful embodiments, the polycystin-1 L3 receptor polypeptide can be a component of a sour/acid receptor, in any of a variety of contexts, including as a taste receptor polypeptide, as a CSF receptor polypeptide or as an acid receptor in other systems, e.g., in the kidney.

A "polycystin-1L3 taste receptor polypeptide" is a polypeptide that is the same as, a splice-variant of, or homologous to a human polycystin-1L3 or murine polycystin-1L3 and that is expressed in taste receptor cells, or that is derived from such a polypeptide that is expressed in such taste receptor cells (e.g., through cloning, recombination, mutation, or the like). The polypeptide can be full length or can be a fragment of a full length protein. A polycystin-1L3 fragment typically includes at least 10 contiguous amino acids corresponding to a native polycystin-1L3 protein, such as a human murine, dog or rat polycystin-1L3. The polycystin-1L3 taste receptor polypeptide can be naturally occurring or recombinant, and can be unpurified, purified, or isolated, and can exist, e.g., in vitro, in vivo, or in situ. In one typical useful embodiment, the polycystin-2L1 taste receptor polypeptide is a transmembrane protein.

A "PKD2L1 gene" is a nucleic acid that encodes a polycystin-2L1 polypeptide. Typically, the gene includes regulatory sequences that direct expression of the gene in one or more cells of interest. Optionally, the PKD2L1 gene is a native gene that includes regulatory and coding sequences that naturally direct expression of a polycystin-2L1 polypeptide.

A "PKD1L3 gene" is a nucleic acid that encodes a polycystin-1L3 polypeptide. Typically, the gene includes regulatory sequences that direct expression of the gene in one or more cells of interest. Optionally, the PKD1L3 gene is a native gene that includes regulatory and coding sequences that naturally direct expression of a polycystin-1L3 polypeptide.

A biological sample comprising the polycystin-2L1 or polycystin-3L1 polypeptide includes any sample comprising the polypeptide that is derived from a biological source, e.g., cells, tissues, organisms, cells, secretions, etc. These samples can include, e.g., cells expressing the receptor, membranes containing the receptor, receptor bound to a chemical matrix, receptor bound to solid surface (e.g., for plasmon resonance), etc. A biochemical source can include biological sources and/or non-biological sources, such as purely synthetic preparations of materials.

A "tastant" is a compound that can be tasted by the relevant organism. These typically include compounds that can stimulate or inhibit one or more activity of one or more taste receptor, taste cells or other sensory cells and/or nerves in the oral cavity. A tastant can be any molecule, including ions, peptides, nucleotides, natural compounds, small organic molecules, etc. that leads to modulation of taste receptor or taste cell activity or a change taste cell function either on its own or in the presence of other compounds.

A "modulator" is a compound that modulates an activity of a given polypeptide, polypeptide complex or receptor, e.g., a taste receptor polypeptide complex, e.g., in response to a tastant, or a CSF receptor or polypeptide or polypeptide complex in response to a change in pH. The term "modulate" with respect to a polycystin-2L1 polycystin-1L3 polypeptide refers to a change in an activity or property of the polypeptide. For example, modulation can cause an increase or a decrease in a protein activity, a binding characteristic, membrane permeability or any other biological, functional, or immunological properties of such proteins. The change in activity can arise from, for example, an increase or decrease in expression of one or more genes that encode these proteins, the stability of an mRNA that encodes the protein, translation efficiency, or from a change in activity of the protein itself. For example, a molecule that binds to polycystin-2L1 or polycystin-1L3 can cause an increase or decrease in a biological activity of the polypeptide. Example modulators include polycystin-2L1 or polycystin-1L3 allosteric enhancers, agonists, antagonists, inverse agonists, or partial agonists, polycystin-2L1 or polycystin-1L3 ligands, antibodies to polycystin-2L1, polycystin-1L3, or complexes thereof, etc.

A "prescreened" compound is a compound that is preselected for a property of interest, such as toxicity, lack of toxicity, bioavailability, chemical structure, type of molecule (natural product, ion, ion channel agonist/antagonist/inverse agonist, etc.), or the like. For example, an "ingestible compound" is a compound that can be safely ingested in an amount that triggers a taste receptor or taste cell response by the compound. Certain compounds such as agonists or enhancers can have such a desired response when present at very low doses, while others are present in higher amounts. In addition, certain ingestible compounds such as enhancers optionally have no taste of their own, but enhance the action of natural or chemically synthesized tastants on a taste receptor or taste cell.

A "transmembrane potential" is the work needed to move a unit of charge across a membrane such as a cell membrane.

A "cationic membrane permeable dye" is a dye which has a positive charge under specified pH (e.g., physiological pH) where the dye can cross a selected membrane such as the membrane of an intact cell. An "anionic membrane permeable dye" is a dye which has a negative charge at a specified pH (e.g., physiological pH) and which is membrane permeable and whose distribution between the inside and outside of the space bounded by the membrane or between the inside and outside of the membrane, depends on the transmembrane potential across the membrane. Similarly, a "neutral dye membrane permeable dye" is membrane permeable and has an overall neutral charge under the relevant conditions at issue, e.g., a specified pH (e.g., physiological pH).

A "voltage sensing composition" is a transmembrane potential indicator, e.g., comprising a fluorescent dye. Common voltage sensing compositions can include one or more cationic or anionic membrane permeable dye(s).

A membrane is "depolarized" when the transmembrane potential across the membrane becomes more positive inside. A membrane is "hyperpolarized" when the transmembrane potential becomes more negative inside.

A membrane is "permeable" to a given component (dye, ion, etc.) when that component can cross the membrane.

Permeability can be dependent upon the relevant conditions, e.g., temperature, ionic conditions, voltage potentials, or the like.

DETAILED DESCRIPTION

The ability to screen taste receptors or other components of a taste reception pathway for response to tastant stimuli is of considerable commercial value. Libraries of putative tastant or modulator compounds can be screened for activity against a given receptor to identify taste enhancers, sour tastants, and the like. The identification of new sour or other tastants is of value, e.g., to provide new flavors that can be added to foods and drinks. Similarly, compounds that modulate activity of a receptor can be used to make the receptor more (or less) sensitive to a tastant, which is particularly valuable when considering responsiveness to tastants that have associated health consequences upon consumption. For example, many preservatives utilize acids, which impact flavors. The ability to neutralize flavor effects facilitates the use of food preservatives.

Given the identification of polycystin-2L1 as a sour/acid taste receptor protein herein, and of polycystin-1L3 as a potential partner for polycystin-2L1, there are several ways in which these proteins can now be screened for responsiveness to test compounds (tastants, activity modulators, etc.), including in high-throughput cell-based assays, in animal behavioral models (e.g., using transgenic animals that express a human or other desirable heterologous polycystin-2L1 or polycystin-3L1 polypeptides), or the like. Modulators of the genes for these polypeptides can similarly be tested for effects on the expression of the proteins. Polymorphisms in the gene for polycystin-2L1 (PKD2L1) or polycystin-1L3 (PKD1L3) can also be detected to provide molecular tests for tasting and other disorders and defects in PKD2L1 and PKD1L3 can be rescued by gene therapy. In this regard, administration of a gene therapy vector to the tastebud is relatively simple, due to ready access to this tissue, and can be targeted to a considerable degree simply by controlling the site of vector administration. Systems and kits for practicing the methods, transgenic animals (PKD2L1 knock-outs and/or transgenics), and related features are also included within the scope of the invention. Further details regarding these various features of the invention are found herein, e.g., below.

In addition to the identification of polycystin-2L1 as a sour/acid taste receptor, polycystin-2L1 is also identified as a pH (e.g., acid level) sensor in certain neuronal cells that are in contact with the CSF. Thus, this invention provides for the surprising discovery of a previously unknown CSF pH sensor, both with respect to polycystin-2L1 and with respect to the specific neuronal pH acid sensing cells in contact with the CSF (e.g., those that express polycystin-2L1). This provides, e.g., a basis for assays that screen for modulators of polycystin-2L1 in the context of its role as a CSF pH sensor, as well as for the identification of defects in PKD2L1 that may affect pH sensing in the CSF.

pH sensation in the CSF regulates, e.g., respiration. Defects in respiration lead to a variety of disorders, including sudden infant death syndrome (SIDS), sleep apnea, persistent hiccups, fatigue, altitude sickness, hyperventilation, and many others. In addition, patients suffering from trauma, anesthesia, or surgery often develop difficulty breathing, which may benefit from administration of appropriate modulators. These and other features of the invention are further described herein.

Screening Test Compounds for Activity Against PC-2L1 and/or PC-1L3

In one aspect, methods of identifying a compound that binds to or modulates an activity of a polycystin-2L1 and/or polycystin-1L3 polypeptide (or complex) are provided. In these methods, a biological or biochemical sample comprising the polypeptide or complex is contacted with a test compound and binding of the test compound to the polypeptide or complex, or modulation of the activity of the polypeptide or complex by the test compound is detected, thereby identifying a compound that binds to or modulates the activity of the polypeptide or complex. Compounds identified by these methods are also a feature of the invention.

Desirably, a test compound can be, e.g., a potentiator or enhancer of the polypeptide or complex, an antagonist of the polypeptide or complex, an agonist of the polypeptide or complex, an inverse agonist of the polypeptide or complex, a ligand that specifically binds to the polypeptide or complex, an antibody that specifically binds to the polypeptide or complex, or the like.

Additional Details Regarding Screening Methods

High throughput methods of screening are particularly useful in identifying tastants or modulators of polycystin-2L1 or polycystin-1L3 polypeptide activity, and/or of PKD2L1 or PKD1L3 gene expression. Generally in these methods, one or more biological sample that includes one or more PKD2L1 or PKD1L3 gene, polycystin-2L1 or polycystin-1L3 polypeptide, or complex thereof, is contacted with a plurality of test compounds. Binding to or modulation of the polypeptide or gene by the test compounds is detected, thereby identifying one or more compound that binds to or modulates activity of the polypeptide, complex and/or gene.

Essentially any available compound library can be screened in such a high-throughput format against a biological or biochemical sample, such as a cell expressing a polycystin-2L1 or polycystin-1L3 taste receptor or CSF sensor polypeptide, and activity of the library members against the polypeptide or expression thereof can be assessed, optionally in a high-throughput fashion.

Many libraries of compounds are commercially available, e.g., from the Sigma Chemical Company (Saint Louis, Mo.), Aldrich chemical company (St. Louis Mo.), and many can be custom synthesized by a wide range of biotech and chemical companies. A variety of proprietary libraries also exist, including those specifically designed for screening of taste receptors, e.g., from Senomyx, Inc. (La Jolla Calif.).

In one desirable aspect, the plurality of test compounds comprise a plurality of compounds. Thus, the library to be screened can include a previously unscreened library of compounds, or can include a pre-screened library of compounds that are pre-screened for any property that is desired, e.g., toxicity, bioavailability, chemical structure, known activity (e.g., ion channel binding or modulating activity) ingestibility, or the like. Further details on available libraries are found below.

In general, test compounds that enhance or potentiate an activity of the polycystin-2L1 or polycystin-1L3 polypeptide or complex can be desirable, e.g., to enhance pH sensitivity for cells in contact with the CSF (e.g., to increase respiration, e.g., to reduce altitude effects), or as flavor enhancers, and can be screened for using the methods of the invention. However, test compounds that inhibit or block an activity of the polycystin-2L1 or polycystin-1L3 polypeptide or complex are also desirable, e.g., where taste sensation associated with a flavor would benefit from reduced responsiveness (e.g., in those cases where more than usual of the tastant is desirably consumed), or in cases where decreased pH responsiveness are desirable (e.g., to reduce hyperventilation).

Additional Details Regarding Assay Formats

In another aspect, the present invention relates to the use of the polycystin-2L1 or polycystin-1L3 polypeptides, complexes thereof, and/or coding nucleic acids in methods for identifying a compound, e.g., a tastant or modulator, that interacts/binds to the polypeptide. The test compound can be selected from natural or synthetic molecules such as ions, proteins or fragments thereof, carbohydrates, organic or inorganic compounds and/or the like. For example, the test compounds can be naturally occurring compounds, ions, sour substitutes, tastants, small organic molecules, peptides, peptide mimetics, a weak acid, CO, $CO_2$, acetic acid, specific blockers of carbonic anhydrase, MK-417, ion channel agonists, ion channel antagonists, ion channel enhancers, non-specific $Ca^+$ channel blockers, Nifedipine and/or structurally related compounds, V1erapamil and/or structurally related compounds, gadolinium and/or structurally related compounds, and/or stretch-induced channel blockers, etc. This can be achieved, e.g., by utilizing the polypeptides of the invention, including active fragments thereof, in cell-free or cell-based assays. A variety of formats are applicable, including measurement of second messenger effects (e.g., $H^+$ flux, $Na^+$ flux, $Ca^{2+}$ flux, ion flux, depolarization of the cell, cell membrane voltage changes, cell membrane conductivity changes, a kinase activity triggered upon binding of a compound to the polypeptide, generation, breakdown or binding of a phorbol ester by the polypeptide, binding of diacylglycerol or other lipids by the polypeptide, cAMP activity, cGMP activity, GTPgammaS binding, phospholipase C activity, activity of an enzyme involved in cellular ionic balance, binding of polycystin-2L1 or polycystin-1L3 to each other or to another polycystin-type protein, or a transcriptional reporter activity assay, e.g., using CRE, SRE, MRE, TRE, NFAT, and/or NFkB-response elements coupled to appropriate reporters.

In one embodiment, cell-free assays for identifying such compounds comprise a reaction mixture containing a polycystin-2L1 or polycystin-3L1 polypeptide or complex encoded by PKD2L1 and/or PKD1L3, or a variant thereof, and a test compound or a library of test compounds. Accordingly, one example of a cell-free method for identifying test compounds that specifically bind to a polycystin 2-L1 polypeptide or a polycystin-3 L1 polypeptide comprises contacting a such a protein or functional fragment thereof with a test compound or library of test compounds and detecting the formation of complexes by conventional methods. Similarly, the effect on PC-1-L3/PC-2-L1 complex formation by the test compound can also be determined by monitoring association of the polycystin proteins in the presence and absence of the test compound.

In one class of useful embodiments, a library of the test compounds can be synthesized on a solid substrate, e.g., a solid surface, plastic pins or some other surface. The test compounds are reacted with the polypeptide(s) and washed to elute unbound polypeptide(s). Bound polypeptide(s) is/are then detected by methods well known in the art. A reciprocal assay can also be used, e.g., in which polypeptide is applied directly onto plates and binding of the test compound to the polypeptide(s) is detected. Antibody or ligand binding to the polypeptide(s) can also be detected in either format.

Interaction between molecules can also be assessed using real-time BIA (Biomolecular Interaction Analysis, e.g., using devices from Pharmacia Biosensor AB), which detect surface plasmon resonance (an optical phenomenon). Detection depends on changes in the mass concentration of macromolecules at the biospecific interface and does not require specific labeling of the molecules. In one useful embodiment, a library of test compounds can be immobilized on a sensor surface, e.g., a wall of a micro-flow cell. A solution containing the polycystin-2L1 or polycystin-1L3 polypeptide or complex thereof is then continuously circulated over the sensor surface. An alteration in the resonance angle, as indicated on a signal recording, indicates the occurrence of an interaction. This general technique is described in more detail in the *BIAtechnology Handbook* by Pharmacia.

Optionally, the polycystin-2L1 or polycystin-1L3 polypeptide is immobilized to facilitate separation of complexes between the polypeptide(s) and a test compound from uncomplexed forms of the polypeptide. This also facilitates automation of the assay. Complexation of polycystin-2L1 or polycystin-1L3 polypeptide (or of polypeptide complexes thereof) can be achieved in any type of vessel, e.g., microtitre plates, microfluidic chambers or channels, micro-centrifuge tubes and test tubes. In one embodiment, the polycystin-2L1 or polycystin-1L3 polypeptide is fused to another protein, e.g., glutathione-S-transferase to form a fusion protein which can be adsorbed onto a matrix, e.g., glutathione Sepharose™ beads (Sigma Chemical. St. Louis, Mo.), which are then combined with the test compound and incubated under conditions sufficient to form test-compound-polypeptide complexes. Subsequently, the beads are washed to remove unbound label, and the matrix is immobilized and the radiolabel is determined.

Similar methods for immobilizing proteins on matrices use biotin and streptavidin. For example, the protein can be biotinylated using biotin NHS(N-hydroxy-succinimide), using well known techniques and immobilized in the well of streptavidin-coated plates.

Cell-free assays can also be used to identify tastants or other compounds (e.g., potential pH response modulators) that bind and/or modulate the activity of a polycystin-2L1 or polycystin-1L3 polypeptide or polypeptide complex. In one embodiment, the polypeptide or complex is incubated with a test compound and the transmembrane ion channel activity of the protein is determined. In another embodiment, the binding affinity of the protein to a target molecule is determined by standard methods.

Further Details Regarding Cell Based Assays

In addition to cell-free assays such as those described above, the polycystin-2L1 or polycystin-1L3 polypeptide, and/or complex thereof can be used in cell-based assay for identifying compounds that bind to, activate and/or modulate polycystin-2L1 or polycystin-1L3 polypeptide or complex activity.

For example, one method for identifying compounds which bind to polycystin-2L1 or polycystin-1L3 polypeptides or complexes comprise providing a cell that expresses one or more of these proteins, e.g., a human polycystin-2L1 and/or polycystin-1L3 polypeptide, combining a test compound with the cell and measuring the formation of a complex between the test compound and the human polycystin-2L1 or polycystin-1L3 polypeptide (or, e.g., between the test compound a polypeptide complex that includes both polypeptides). The cell can be a mammalian cell (e.g., a CHO cell), a yeast cell, a bacterial cell, an insect cell, a *Xenopus* oocyte, a human or other mammalian taste cell, a kidney cell or any other cell expressing the polycystin-2L1 or polycystin-1L3 polypeptide, whether that expression is natural to the cell or the result of recombinant introduction of a PKD2L1 or PKD1L3 gene of interest. Further details regarding appropriate cells is found below.

In another embodiment, taste cells, kidney cells, neuronal cells, or cells expressing heterologous polycystin-2L1 or polycystin-1L3 polypeptides or polypeptide complexes, or membrane preparations of such cells, can be utilized to screen for bioactivity of test compounds. The polycystin-2L1 polypeptides described herein are $Ca^{2+}$ permeable cation selective channels (pore forming channels). In addition, G-proteins such as PC-1 and PC 1-like proteins also interact with polycystin-2 proteins and may interact with polycystin-2L1 polypeptides. A variety of intracellular effectors have been identified as being $Ca^{2+}$/G-protein regulated including, but not limited to, $Ca^{2+}$-induced intraorganellar $Ca^{2+}$ release by ryanodine and/or IP3 receptors, adenyl cyclase, cyclic GMP, phospholipase C, phospholipase A2 and phosphodiesterases, etc.

Accordingly, the level of such second messengers produced by the aforementioned intracellular effectors, and thus activity of polycystin-2L1 polypeptides, can also be measured by techniques that are well known. For example, the level of cAMP produced by activation of adenyl cyclase can be measured by assays which monitor cAMP, either in vivo by using FRET or transcriptional reporters sensitive to cAMP, or in vitro by directly measuring cAMP production. The GTPase activity by G proteins such as or polycystin-1L3 can be measured, e.g., in plasma membrane preparations by measuring the hydrolysis of gamma $^{32}$P GTP, or in vivo by FRET or by monitoring activity of downstream effectors such as PLC, adenylate cyclase, etc. Breakdown of phosphatidylinositol-4,5-bisphosphate to 1,4,5-IP3 and diacylglycerol can be monitored by measuring the amount of diacylglycerol using thin-layer chromatography, or measuring the amount of IP3 using radiolabeling techniques or HPLC, or in vivo by activation of the IP3 receptor and release of calcium from internal stores. The generation of arachidonic acid by the activation of phospholipase A2 can be readily quantitated by well-known techniques.

Efflux of intracellular calcium or influx of calcium from outside the cell can be measured using conventional techniques, e.g., loading cells with a $Ca^{++}$ sensitive fluorescent dye such as fura-2 or indol-1, and measuring any change in $Ca^{++}$ using a fluorometer, such as Fluoskan Ascent Fluorescent Plate Reader or Flurometric Imaging Plate Reader. The signal pathways initiated by polycystin-2L1 or polycystin-1L3 polypeptides or complexes in response to sour, acid, base or other compounds can also be monitored by reporter gene assays.

Assays that monitor changes in membrane potential by (1) voltage measurements in *Xenopus* oocytes injected with mRNA encoding PKD2L1 and/or PKD1L3, (2) patch clamping in tissue culture cells expressing the receptor, and (3) fluorometric assays using voltage-sensitive dyes or ionic fluxes are preferred assays for monitoring membrane potential in the context of the present invention.

In other aspects, interactions between polycystin-2L1 or polycystin-1L3 and related proteins are monitored to detect activity or binding properties of polycystin2L1 or polycystin-1L3, or related complexes comprising polycystin-2L1 and/or polycystin-1L3. For example, PC2-like proteins (which are typically ion channels) often interact with PC-1 like proteins (which are typically G-proteins) to provide functional receptor complexes. Thus, in one aspect, interactions between polycystin-2L1 and polycystin-1L3 can be monitored. In addition, homodimers and heterodimers between different PC-1 and PC-2 proteins can exist. Accordingly, binding between polycystin 2L1 and other polycystins (including, but not limited to polycystin-1L3) can be monitored, e.g., by FRET or other protein-protein interaction technologies (cross-linking, etc.) to monitor homodimer and heterodimer formation, gating by PC-1 or PC-2 or related proteins, or the like.

As described, other assays such as melanophore assays, Phospholipase C assays, $Ca^{++}$ mobilization assays, beta-arrestin FRET assays, and transcriptional reporter assays, e.g., using CRE, SRE, MRE, TRE, NFAT, and/or NFkB-response elements coupled to appropriate reporters can be used. Detection using reporter genes coupled to appropriate response elements are particularly convenient. For example, the coding sequence to chloramphenicol acetyl transferase, beta galactosidase or other convenient markers are coupled to a response element that is activated by a second messenger that is activated by a protein of the invention, e.g., through $Ca^{++}$ release. Cells expressing the marker in response to application of an appropriate test compound are detected by cell survival, or by expression of a colorimetric marker, or the like, according to well established methods.

Any of a variety of potential modulators of polycystin-2L1 or polycystin-1L3, or PKD2L1 or PKD1L3 activity or expression can be screened for. For example, potential modulators (ions, sour substitutes, small organic molecules, peptides, peptide mimetics, acids, bases, weak acids, $CO_2$, acetic acid, blockers of carbonic anhydrase, MKb417, small molecules, organic molecules, inorganic molecules, proteins, hormones, transcription factors, or the like) can be contacted to a cell and an effect on a polycystin-2L1 or polycystin-1L3 polypeptides or complexes and/or PKD2L1 or PKD1L3 gene activity and/or expression monitored by any of the assays described herein or known in the art.

Furthermore, expression of PKD2L1 or PKD1L3 can be detected, e.g., via northern analysis or quantitative (e.g., real time) RT-PCR, before and after application of potential expression modulators. Similarly, promoter regions of a PKD2L1 and/or PKD1L3 gene(s) of interest (e.g., generally sequences in the region of the start site of transcription, e.g., within 5 KB of the start site, e.g., 1 KB, or less e.g., within 500BP or 250BP or 100 BP of the start site) can be coupled to reporter constructs (CAT, beta-galactosidase, luciferase or any other available reporter) and can be similarly be tested for expression activity modulation by the potential modulator. In either case, the assays can be performed in a high-throughput fashion, e.g., using automated fluid handling and/or detection systems, in a serial or parallel fashion. Similarly, activity modulators can be tested by contacting a potential modulator to an appropriate cell using any of the activity detection methods herein, regardless of whether the activity that is detected is the result of activity modulation, expression modulation or both.

In any of the assays herein, control compounds can be administered and the activity of the control compounds compared to those of the test compounds to verify that changes in activity resulting from application of the test compound are not artifacts. For example, control compounds can include the various dyes, buffers, adjuvants, carriers, or the like that the test compounds are typically administered with, but lacking a putative test compound.

Details Regarding Transmembrane Potential Measurements and Transmembrane Dyes

As noted above, the invention optionally includes monitoring transmembrane potential (TM potential) to track ion channel activity of polycystin 2L1 or polycystin 1L3. In general, the distribution of a permeable ion between the inside and outside of a cell or other membrane depends on the transmembrane potential of the cell membrane. In particular, for ions separated by a semi-permeable membrane, the electrochemical potential difference ($\Delta\mu_j$) which exists across the membrane, is given by $\Delta\mu_j = 2.3\ RT\ \log\ [j_I]/[j_o] + zE_RF$, where R is the universal gas constant, T is an absolute temperature of the composition, F is Faraday's constant in coulombs, $[j_I]$ is the concentration of an ion (j) on an internal or intracellular side of the at least one membrane, $[j_o]$ is the concentration of j on an external or extracellular side of the at least one membrane, z is a valence of j and $E_R$ is a measured transmembrane potential. Thus, the calculated equilibrium potential difference ($E_j$) for ion $j = -2.3RT(zF)^{-1}\ \log[j_I]/[j_o]$ (this is often referred to as the "Nernst equation"). See, Selkurt, ed. (1984) *Physiology* 5th *Edition*, Chapters 1 and 2, Little, Brown, Boston, Mass. (ISBN 0-316-78038-3); Stryer (1995) *Biochemistry* 4th *edition* Chapters 11 and 12, W.H. Freeman and Company, NY (ISBN 0-7167-2009-4); Haugland (1996) *Handbook of Fluorescent Probes and Research Chemicals Sixth Edition* by Molecular Probes, Inc. (Eugene Oreg.) Chapter 25 (Molecular Probes, 1996) and http://www.probes.com/handbook/sections/2300.html (Chapter 23 of the on-line 1999 version of the *Handbook of Fluorescent Probes and Research Chemicals Sixth Edition* by Molecular Probes, Inc.) (Molecular Probes, 1999) and Hille (1992) Ionic Channels of Excitable Membranes, second edition, Sinauer Associates Inc. Sunderland, Mass. (ISBN 0-87893-323-9) (Hille), for an introduction to transmembrane potential and the application of the Nernst equation to transmembrane potential. In addition to the Nernst equation, various calculations which factor in the membrane permeability of an ion, as well as Ohm's law, can be used to further refine the model of transmembrane potential difference, such as the "Goldman" or "constant field" equation and Gibbs-Donnan equilibrium. See Selkurt, ed. (1984) *Physiology* 5th *Edition*, Chapter 1, Little, Brown, Boston, Mass. (ISBN 0-316-78038-3) and Hille at e.g., chapters 10-13.

Increases and decreases in resting transmembrane potential—referred to as membrane depolarization and hyperpolarization, respectively—play a central role in many physiological processes, including ion-channel gating. Potentiometric optical probes (typically potentiometric dyes) provide a tool for measuring transmembrane potential and changes in transmembrane potential over time (e.g., transmembrane potential responses following the addition of a composition which affects transmembrane potential) in membrane containing structures such as organelles, cells and in vitro membrane preparations. In conjunction with probe imaging techniques (e.g., visualization of the relevant dyes), dye probes are used to map variations in transmembrane potential across cells membranes.

Potentiometric probes include cationic or zwitterionic styryl dyes, cationic rhodamines, anionic oxonols, hybrid oxonols and merocyanine 540. The class of dye determines factors such as accumulation in cells, response mechanism and cell toxicity. See, Molecular Probes 1999 and the reference cited therein; Plasek et al. (1996) "Indicators of Transmembrane potential: a Survey of Different Approaches to Probe Response Analysis." *J Photochem Photobiol*, Loew (1994) "Characterization of Potentiometric Membrane Dyes." *Adv Chem Ser* 235, 151 (1994); Wu and Cohen (1993) "Fast Multisite Optical Measurement of Transmembrane potential" *Fluorescent and Luminescent Probes for Biological Activity*, Mason, Ed., pp. 389-404; Loew (1993) "Potentiometric Membrane Dyes." *Fluorescent and Luminescent Probes for Biological Activity*, Mason, Ed., pp. 150-160; Smith (1990) "Potential-Sensitive Molecular Probes in Membranes of Bioenergetic Relevance." *Biochim Biophys Acta* 1016, 1; Gross and Loew (1989) "Fluorescent Indicators of Transmembrane potential: Microspectrofluorometry and Imaging." *Meth Cell Biol* 30, 193; Freedman and Novak (1989) "Optical Measurement of Transmembrane potential in Cells, Organelles, and Vesicles" *Meth Enzymol* 172, 102 (1989); Wilson and Chused (1985) "Lymphocyte Transmembrane potential and Ca$^{+2}$-Sensitive Potassium Channels Described by Oxonol Dye Fluorescence Measurements" *Journal of Cellular Physiology* 125:72-81; Epps et al. (1993) "Characterization of the Steady State and Dynamic Fluorescence Properties of the Potential Sensitive dye bis-(1.3-dibutylbarbituric acid) trimethine oxonol (DiBAC$_4$(3) in model systems and cells" *Chemistry of Physics and Lipids* 69:137-150, and Tanner et al. (1993) "Flow Cytometric Analysis of Altered Mononuclear Cell Transmembrane potential Induced by Cyclosporin" *Cytometry* 14:59-69.

Potentiometric dyes are typically divided into at least two categories based on their response mechanism. The first class of dyes, referred to as fast-response dyes (e.g., styrylpyridinium dyes; see, e.g., Molecular Probes (1999) at Section 23.2), operate by a change in the electronic structure of the dye, and consequently the fluorescence properties of the dye, i.e., in response to a change in an electric field which surrounds the dye. Optical response of these dyes is sufficiently fast to detect transient (millisecond) potential changes in excitable cells, e.g., isolated neurons, cardiac cells, and even intact brains. The magnitude of the potential-dependent fluorescence change is often small; fast-response probes typically show a 2-10% fluorescence change per 100 mV.

The second class of dyes, referred to as slow-response (or "Nernstian") dyes (See, e.g., Molecular Probes, 1999 at Section 23.3), exhibit potential-dependent changes in membrane distribution that are accompanied by a fluorescence change. The magnitude of their optical responses is typically larger than that of fast-response probes. Slow-response probes, which include cationic carbocyanines, rhodamines and anionic oxonols, are suitable for detecting changes in a variety of transmembrane potentials of, e.g., nonexcitable cells caused by a variety of biological phenomena, including ion channel permeability. The structures of a variety of available slow response dyes are found e.g., at table 25.3 of Molecular Probes (1996).

Many slow, Nernstian dyes such as carbocyanines, rhodamines and oxonols are used to measure transmembrane potential by virtue of voltage-dependent dye redistribution and fluorescence changes resulting from the redistribution. Fluorescence changes which may be caused by redistribution include: a change of the concentration of the fluorophore within the cell or vesicle, a change in the dye fluorescence due to aggregation or a change in dye fluorescence due to binding to intracellular or intravesicular sites. Typically, 10-15 minutes of equilibration time is used to allow the dyes to redistribute across the cell membrane after changing the transmembrane potential.

Examples of available anionic dyes that can be used for measurement of transmembrane potential include the anionic bis-isoxazolone oxonols which accumulate in the cytoplasm of depolarized cells by a Nernst equilibrium-dependent uptake from the extracellular solution. Of the oxonols studied in one reference ("Kinetics of the Potential-Sensitive Extrinsic Probe Oxonol VI in Beef Heart Submitochondrial Particles." J. C. Smith, B. Chance. *J Membrane Biol* 46, 255 (1979)), oxonol VI gave the largest spectral shifts, with an isosbestic point at 603 nm. Oxonol VI responds to changes in potential more rapidly than oxonol V.

The three common bis-barbituric acid oxonols, often referred to as DiBAC dyes, form a family of spectrally distinct potentiometric probes with excitation maxima at approximately 490 nm (DiBAC$_4$(3), 530 nm (DiSBAC$_2$(3)) and 590 nm (DiBAC$_4$(5)). DiBAC$_4$(3) has been used in many publications that cite using a "bis-oxonol" (Molecular Probes, 1999, chapter 23). The dyes enter depolarized cells where they bind to intracellular proteins or membranes and exhibit enhanced fluorescence and red spectral shifts. Increased depolarization results in more influx of the anionic dye and thus an increase in fluorescence. DiBAC$_4$(3) has particularly high voltage sensitivity. The long-wavelength DiSBAC$_2$(3) has frequently been used in combination with the UV light-excitable Ca$^{2+}$ indicators indo-1 or fura-2 for the simultaneous measurements of transmembrane potential and Ca$^{2+}$ concentrations (id. at Table 23.2).

Classes of cationic membrane permeable dyes that can be used as ion sensing compositions include, e.g., indo-carbocyanine dyes, thio-carbocyanine dyes, oxa-carbocyanine dyes (see Molecular Probes on-line catalogue, updated as of Aug. 10, 2000, at section 23.3, entitled "Slow-Response Dyes;" http://www.probes.com/handbook/sections/2303.html). See also, Sims, et al. (1974) "Studies on the Mechanism by Which Cyanine Dyes Measure Membrane Potential in Red Blood Cells and Phosphatidylcholine Vesicles," *Biochemistry* 13, 3315; Cabrini and Verkman (1986) "Potential-Sensitive Response Mechanism of DiS-C3 (5) in Biological Membranes," *Membrane Biol* 92, 171; Guillet and Kimmich (1981) "DiO-C3-(5) and DiS-C3-(5): Interactions with RBC, Ghosts and Phospholipid Vesicles," *J Membrane Biol* 59, 1; Rottenberg and Wu (1998) "Quantitative Assay by Flow Cytometry of the Mitochondrial Membrane Potential in Intact Cells," *Biochim Biophys Acta* 1404, 393 (1998).

Other useful transmembrane dyes include amino napthylethylenyl pyridinium dyes, and dialkyl amino phenyl polyphenyl pyridinium dyes. The amino napthylethylenyl pyridinium dyes include the ANEP type dyes, e.g., listed in the Molecular Probes catalog (Di-4-ANEPPS, Di-8-ANEPPS, Di-2-ANEPEQ, Di-8-ANEPEQ and Di-12-ANEPEQ). Dialkyl amino phenyl polyphenyl pyridinium dyes include the RH type dyes listed in the Molecular Probes catalog (RH160, RH237, RH 421, RH 704, RH 414, and RH 461).

In general, changes in the level of fluorescence of the biological sample (e.g., containing PC-1-L3 and/or PC-2-L1 and/or coding nucleic acids)-test compound mixture detected, where the change in fluorescence is indicative of a change in transmembrane potential. Typically, the assay methods described herein are used to detect the effect of the test compound on the transmembrane potential of a cell or other membrane. Where one is seeking to determine the effect of a test compound on a cell's transmembrane potential, e.g., through a change in ion flux, transport, membrane permeability, or the like, one can expose the cell, membrane, etc., to the test compound and the cell etc., is examined for the presence of a previously absent fluorescent signal (or the absence of a previously present fluorescent signal). Of particular interest are the effects of tastant compounds and potential modulators on cellular functioning, as determinable from TMP measurements.

For example, in one assay format, a dye is contacted to a biological sample. In accordance with these methods, the sample can be placed into a reaction vessel, such as a microwell dish, and the level of fluorescence from the composition is measured, optionally over a period of time. This can be used to provide an initial or background level of fluorescence indicative of an existing transmembrane potential for the biological sample. A selected test compound is then added to the biological sample (or these procedures are carried out in parallel, providing control and experimental samples). The test compound can be tested alone, or is added before, together or after addition of a tastants to determine its effect on tastant responses (e.g. enhancement or inhibition). Following the stimulus, the fluorescence level of the biological sample is again measured (typically over time) and compared to the initial fluorescent level or the fluorescence level in a control cell population (e.g., which is exposed to a control TMP modulator). Any change in the level of fluorescence not attributable to dilution by the test compound (as determined from an appropriate control) is then attributable to the effect the test compound has on the cell's transmembrane potential, or rate of TMP change in response to depolarization or hyperpolarization events.

A suitable negative control can be used in the assay, such as a biological sample that does not include the PC-1-L3 and/or PC-2-L1 and/or a coding nucleic acid, to ensure that the effect being observed is caused by the relevant protein or complex. Similarly, a suitable positive control can be used in the assay, such as a test compound known to effect the protein, gene or complex under study, to ensure that the biological sample components are suitably active.

These types of reactions are carried out in an appropriate reaction receptacle that allows measurement of fluorescence, in situ. As such, the receptacle is typically a transparent reaction vessel, such as a test tube, cuvette, a reaction well in a multiwell plate, or a transparent conduit, e.g., a capillary, microchannel or tube.

The assay methods of the present invention are particularly useful in performing high-throughput (greater than 1,000 compounds/day) and even ultra-high throughput (e.g., greater than 10,000 compounds/day) screening of chemical libraries, e.g., in searching for tastant/modulator leads. These experiments may be carried out in parallel by a providing a large number of reaction mixtures (e.g., cell suspensions as described herein) in separate receptacles, typically in a multiwell format, e.g., 96 well, 324 well or 1536 well plates. Different test compounds (library members) are added to separate wells, and the effect of the compound on the reaction mixture is ascertained, e.g., via the fluorescent signal. These parallelized assays are generally carried out using specialized equipment e.g., as described above to enable simultaneous processing of large numbers of samples, i.e., fluid handling by robotic pipettor systems and fluorescent detection by multiplexed fluorescent multi-well plate readers.

Patch Clamping

As noted above, monitoring of transmembrane dye flow is a preferred method of monitoring test compound effects on ion channels. A second preferred method uses voltage clamping, such as patch clamping. This is a particularly useful method e.g., when using *Xenopus* oocytes.

A voltage clamp allows for the measurement of ion currents flowing across a cell membrane. Originally, the voltage clamp used two electrodes and a feedback circuit for transmembrane measurements. In the original Cole-Marmount voltage clamp, both electrodes are placed inside a cell and transmembrane voltage is recorded through one of the electrodes (the "voltage electrode") relative to an outside reference (e.g., ground). The second electrode passes current into the cell and is termed the "current electrode".

Briefly, a "holding voltage" is maintained across the cell membrane. Anytime the cell makes a deviation from this holding voltage by passing an ion current across its membrane, an operational amplifier generates an "error signal". The error signal is the difference between the holding voltage specified by the experimenter and the actual voltage of the cell. The feedback circuit of the voltage clamp passes current into the cell (via the current electrode) in the polarity needed to reduce the error signal to zero. Thus, the current is applied in a polarity opposite current that the cell is passing across its membrane, and the clamp circuit provides a current that is the mirror image of the cellular current. This mirror or "clamp current" can be easily measured, giving an accurate reproduction of the currents flowing across the cell's membrane (although in the opposite polarity).

A modern variant of this general method is the "patch clamp" which uses a single electrode device. The patch clamp technique is in common use to monitor the flow of ions across a membrane (Neher E (1992) "Nobel lecture. Ion channels for communication between and within cells" *Neuron.* 8(4):605-12). The patch clamp technique involves applying a very finely drawn glass micropipette onto the surface of a cell to form an electrode. This electrode is pressed against a cell membrane and suction is applied to the inside of the electrode to pull the cell's membrane inside the tip of the electrode. This suction causes the cell to form a tight seal with the electrode (a "giga-ohm seal," as the electrical resistance of the seal is in excess of one giga-ohm). From this point, at least 4 different experimental approaches can be taken. First, the electrode can be left sealed to a patch of membrane (a "cell-attached patch"). This allows for the recording of currents through single ion channels in that patch of membrane. Second, the electrode can be withdrawn from the cell, ripping a patch of membrane off of the cell. This forms an "inside-out" patch. This is useful when the environment on the inside of an ion channel is to be studied. Third, the electrode can be withdrawn from the cell, allowing a blob of membrane to bud from the cell. When the electrode is pulled away, this blob will part from the cell and reform as a ball of membrane on the end of the electrode, with the outside of the membrane being the surface of the ball (thus the name "outside out patch"). Such "outside out" patching permits examination of the properties of an ion channel when it is protected from the outside environment, but not in contact with it's usual environment. Fourth, the electrode can be left in place, but harder suction is applied to rupture the portion of the cell's membrane that is inside the electrode, providing access to the intracellular space of the cell. This is known as "whole-cell recording". This method is also sometimes misnamed a "whole cell patch." The advantage of whole cell recording is that the sum total current that flows across the cell's membrane can be recorded.

Thus, the voltage clamping such as the patch clamp technique allows the recording of single ion-channel currents, or alternatively currents from entire small cells. In the context of the present invention, this provides a platform for the analysis of changes in currents that result from application of a test compound of modulator.

A modern variant of the classical patch clamp that can be adapted to the present invention is the planar patch clamp, which uses a planar array of PDMS electrodes that mimic a classical glass electrode (Klemic et al. (2002) "Micromolded PDMS Electrode Allows Patch Clamp Electrical Recording From Cells" *Biosensors and Bioelectronics* 597-604). This modern patch clamp is suited to high throughput patch clamp analysis, allowing many different cells to be analyzed for ion channel activity simultaneously. Patch clamp devices are also commercially available, e.g., from Axon Instruments.

Additional Screening System Details

Automated systems of the invention can facilitate the screening methods noted above (both in vitro and in vivo screening methods). That is, systems that facilitate cell or biochemical sample based screening for polycystin-2L1/PKD2L1 and/or polycystin-1L3/PKD1L3 expression and/or activity are a feature of the invention. Similarly, systems designed to monitor feeding/drinking/licking etc. behavior of animals, or physiological responses of animals (respiration rate, oxygen consumption, blood pH, etc.) including non-human transgenic laboratory animals, are also a feature of the invention. System features herein are generally applicable to the methods herein and vice-versa.

Biological/Biochemical Sources/Libraries

High-throughput automated systems that detect compounds that bind to and/or modulate an activity of a polycystin-2L1 or polycystin-1L3 polypeptide, or complex thereof, typically include a biological/biochemical sample (that includes the polypeptide or complex, e.g., any cell or other material described herein) and a source of a plurality of test compounds. A detector detects binding of one or more of the test compounds to the polycystin-2L1 or polycystin-1L3 polypeptide, or modulation of a level or activity of the polypeptide or complex (or mRNA transcript(s) corresponding to the polypeptide or polypeptide complex) by the test compounds, thereby identifying a putative modulator, tastant, acid receptor binding moiety, etc., that binds to or otherwise modulates an activity of the polycystin-2L1 or polycystin-1L3 polypeptide or complex.

The source of test compound for such systems and in the practice of the methods of the invention can be any commercially available or proprietary library of materials, including compound libraries from Senomyx (La Jolla, Calif.), Sigma (St. Louis Mo.), Aldrich (St. Louis Mo.), Agilent Technologies (Palo Alto, Calif.) or the like. The format of the library will vary depending on the system to be used. In one typical embodiment, libraries of sample materials are arrayed in microwell plates (e.g., 96, 384 or more well plates), which can be accessed by standard fluid handling robotics, e.g., using a pipettor or other fluid handler with a standard ORCA robot (Optimized Robot for Chemical Analysis) available from Beckman Coulter (Fullerton, Calif.). Standard commercially available workstations such as the Caliper Life Sciences (Hopkinton, Mass.) Sciclone ALH 3000 workstation and Rapidplate™ 96/384 workstation provide precise 96 and 384-well fluid transfers in a small, highly scalable format. Plate management systems such as the Caliper Life Sciences Twister® II Advanced Capability Microplate Handler for End-Users, OEM's and Integrators provide plate handling, storage and management capabilities for fluid handling, while the Presto™ AutoStack provides fast reliable access to consumables presenting trays of tips, reagents, microplates or deep wells to an automated device (e.g., the ALH 3000) without robotic arm intervention.

Microfluidic systems for handling and analyzing microscale fluid samples, including cell based and non-cell based approaches that can be used for analysis of test compounds on biological samples in the present invention are also available, e.g., the Caliper Life Sciences various LabChip® technologies (e.g., LabChip® 90 and 3000) and Agilent Technologies (Palo Alto, Calif.) 2100 and 5100 devices. Similarly, interface devices between microfluidic and standard plate handling technologies are also commercially available. For example, the Caliper Technologies LabChip® 3000 uses "sipper chips" as a "chip-to-world" interface that allows automated sampling from microtiter plates. To meet the needs of high-throughput environments, the LabChip® 3000 employs four or even twelve sippers on a single chip so that samples can be processed, in parallel, up to twelve at a time. Solid phase libraries of materials can also be conveniently accessed using sipper or pipetting technology, e.g., solid phase libraries can be gridded on a surface and dried for later rehydration with a sipper or pipette and accessed through the sipper or pipette.

As already noted, with regard to the systems and methods of the invention, the particular libraries of compounds can be any of those that now exist, e.g., those that are commercially available, or that are proprietary. A number of libraries of test compounds exist, e.g., those from Senomyx (La Jolla, Calif.) (which include libraries pre-screened for desirable tastant properties), Sigma (St. Louis Mo.), and Aldrich (St. Louis Mo.). Other current compound library providers include Actimol (Newark Del.), providing e.g., the Actiprobe 10 and Actiprobe 25 libraries of 10,000 and 25,000 compounds, respectively; BioMol (Philedelphia, Pa.), providing a variety of libraries, including natural compound libraries and the Screen-Well™ Ion Channel ligand library which are usefully screened against the receptors herein, as well as several other application specific libraries; Enamine (Kiev, Ukranie) which produces custom libraries of billions of compounds from thousands of different building blocks, TimTec (Newark Del.), which produces general screening stock compound libraries containing>100,000 compounds, as well as template-based libraries with common heterocyclic lattices, libraries for targeted mechanism based selections, including kinase modulators, GPCR Ligands, channel modulators, etc., privileged structure libraries that include compounds containing chemical motifs that are more frequently associated with higher biological activity than other structures, diversity libraries that include compounds pre-selected from available stocks of compounds with maximum chemical diversity, plant extract libraries, natural products and natural product-derived libraries, etc; AnalytiCon Discovery (Germany) including NatDiverse (natural product analogue screening compounds) and MEGAbolite (natural product screening compounds); Chembridge (San Diego, Calif.) including a wide array of targeted or general and custom or stock libraries; ChemDiv (San Diego, Calif.) providing a variety of compound diversity libraries including CombiLab and the International Diversity Collection; Comgenix (Hungary) including ActiVerse™ libraries; MicroSource (Gaylordsville, Conn.) including natural libraries, agro libraries, the NINDS custom library, the genesis plus library and others; Polyphor (Switzerland) including privileged core structures as well as novel scaffolds; Prestwick Chemical (Washington D.C.), including the Prestwick chemical collection and others that are pre-screened for biotolerance; Tripos (St. Louis, Mo.), including large lead screening libraries; and many others. Academic institutions such as the Zelinsky Institute of Organic Chemistry (Russian Federation) also provide libraries of considerable structural diversity that can be screened in the methods of the invention.

Detectors and Other System Components

Although the devices and systems specifically illustrated herein are generally described in terms of the performance of a few or one particular operation, it will be readily appreciated from this disclosure that these systems permit easy integration of additional operations. For example, the systems described will optionally include structures, reagents and systems for performing virtually any number of operations both upstream and downstream from the operations specifically described herein. Such upstream operations include sample handling and preparation operations, e.g., cell separation, extraction, purification, culture, amplification, cellular activation, labeling reactions, dilution, aliquotting, and the like. Similarly, downstream operations may include similar operations, including, e.g., separation of sample components, labeling of components, assays and detection operations, movement of components into contact with cells or other membrane preparations, or materials released from cells or membrane preparations, or the like.

Upstream and downstream assay and detection operations include, without limitation, cell fluorescence assays, cell activity assays, receptor/ligand assays, immunoassays, and the like. Any of these elements can be fixed incorporated into the systems herein.

Instrumentation for high throughput optical screening of cell assays is available. In addition to the systems noted herein, other automated approaches can also be practiced with the dyes and methods of the invention. For example, the FLIPR (Fluorescence Imaging Plate Reader) was developed to perform quantitative optical screening for cell based kinetic assays (Schroder and Neagle (1996) "FLIPR: A New Instrument for Accurate, High Throughput Optical Screening" *Journal of Biomolecular Screening* 1(2):75-80). This device can be adapted to the present invention, e.g., by using dyes to monitor TMP, as discussed above.

In general in the present invention, materials such as cells and dyes are optionally monitored and/or detected so that an activity such as TMP activity can be determined. Depending on the label signal measurements, decisions can be made regarding subsequent operations, e.g., whether to assay a particular tastant/modulator in detail to determine detailed receptor binding/activity kinetic information.

The systems described herein generally include fluid handling devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format. Patch clamps, or other features described herein are also optionally features of the invention.

Controllers

A variety of controlling instrumentation is optionally utilized in conjunction with the fluid handling elements described above, for controlling the transport and direction of fluids and/or materials (biological samples, test compounds, etc.) within the systems of the present invention. Controllers typically include appropriate software directing fluid and material transport in response to user instructions.

Typically, the controller systems are appropriately configured to receive or interface with a fluid handling or other system element as described herein. For example, the controller and/or detector, optionally includes a stage upon which a sample is mounted to facilitate appropriate interfacing between the controller and/or detector and the rest of the system. Typically, the stage includes an appropriate mounting/alignment structural elements, such as a nesting well, alignment pins and/or holes, asymmetric edge structures (e.g., to facilitate proper alignment of slides, microwell plates or microfluidic "chips"), and the like.

Detectors

Within the systems, detectors can take any of a variety of forms. The various fluid handling stations noted above often come with integrated detectors, e.g., optical or fluorescent detectors. However, other detectors such as patch clamp devices, fluorescence detectors that detects FRET, changes in membrane potential or flow of a dye into or out of the cell are also suitable, depending on the application.

Generally, devices herein optionally include signal detectors, e.g., which detect fluorescence, phosphorescence, radioactivity, pH, charge, absorbance, luminescence, temperature, magnetism or the like. As noted, fluorescent and patch clamp detection is especially preferred and generally used for detection of voltage changes, or flow of voltage sensitive compounds (however, as noted, upstream and downstream operations can be performed on cells, dyes, modulators or the like, which can involve other detection methods).

System signal detectors are typically disposed adjacent to a site of reaction or mixing between the biological/biochemical sample and the test compound. This site can be a test tube, microwell plate, microfluidic device, or the like. The site is within sensory communication of the detector. The phrase "within sensory communication" generally refers to the relative location of the detector that is positioned relative to the site so as to be able to receive a particular relevant signal from that container. In the case of optical detectors, e.g., fluorescence, FRET, or fluorescence polarization detectors, sensory communication typically means that the detector is disposed sufficiently proximal to the container that optical, e.g., fluorescent signals, are transmitted to the detector for adequate detection of those signals. Typically this employs a lens, optical train or other detection element, e.g., a CCD, that is focused upon a relevant portion of the container to efficiently gather and record these optical signals.

Example detectors include patch-clamp stations, photo multiplier tubes, spectrophotometers, a CCD array, a scanning detector, a microscope, a galvo-scann or the like. Cells, dyes or other components which emit a detectable signal can be flowed past or moved into contact with the detector, or, alternatively, the detector can move relative to an array of samples (or, the detector can simultaneously monitor a number of spatial positions corresponding to samples, e.g., as in a CCD array).

The system typically includes a signal detector located proximal to the site of mixing/reaction. The signal detector detects the detectable signal, e.g., for a selected length of time (t). For example, the detector can include a spectrophotometer, or an optical detection element. Commonly, the signal detector is operably coupled to a computer, which deconvolves the detectable signal to provide an indication of the transmembrane potential, e.g., an indication of a change in the potential over time.

The detector can detect transmembrane potential (the work needed to move a unit of charge across a membrane such as a cell membrane), e.g., through detecting flow of a cationic membrane permeable dye, an anionic Nernstian dye, an anionic membrane permeable dye, or other voltage sensing composition across the membrane over time, e.g., in response to application of a test compound. Changes in the rate of depolarization and hyperpolarization are monitored in response to a test (e.g., putative modulator) compound, e.g., as compared to a control that does not include the test compound. Permeable dyes are particularly useful for monitoring ion flow, e.g., dyes that can equilibrate across the membrane relatively quickly, typically in about 1 hour, or less. Permeability can be dependent upon the relevant conditions, e.g., temperature, ionic conditions, voltage potentials, or the like.

Computer

Either or both of the controller system and/or the detection system are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of samples. Additionally, the software is optionally used to control flow of materials.

Biosensors

Biosensors of the invention are devices or systems that comprise the polypeptides of the invention (e.g., a polycystin-2L1 or polycystin-1L3 polypeptide) coupled to a readout that measures or displays one or more activity of the polypeptide. Thus, any of the above described assay components can be configured as a biosensor by operably coupling the appropriate assay components to a readout. The readout can be optical (e.g., to detect cell markers, ion-sensitive dyes, cell potential, or cell survival) electrical (e.g., coupled to a FET, a BIAcore, or any of a variety of others), spectrographic, or the like, and can optionally include a user-viewable display (e.g., a CRT or optical viewing station). The biosensor can be coupled to robotics or other automation, e.g., microfluidic systems, that direct contact of the test compounds to the proteins of the invention, e.g., for automated high-throughput analysis of test compound activity. A large variety of automated systems that can be adapted to use with the biosensors of the invention are commercially available. For example, automated systems have been made to assess a variety of biological phenomena, including, e.g., expression levels of genes in response to selected stimuli (Service (1998) "Microchips Arrays Put DNA on the Spot" *Science* 282:396-399). Laboratory systems can also perform, e.g., repetitive fluid handling operations (e.g., pipetting) for transferring material to or from reagent storage systems that comprise arrays, such as microtiter trays or other chip trays, which are used as basic container elements for a variety of automated laboratory methods. Similarly, the systems manipulate, e.g., microtiter trays and control a variety of environmental conditions such as temperature, exposure to light or air, and the like. Many such automated systems are commercially available. Examples of automated systems are available from Caliper Technologies (including the former Zymark Corporation, Hopkinton, Mass.), which utilize various Zymate systems which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). A number of automated approaches to high-throughput activity screening are provided by the Genomics Institute of the Novartis Foundation (La Jolla, Calif.); See GNF.org on the world-wide web. Microfluidic screening applications are also commercially available from Caliper Technologies Corp. For example, (e.g., LabMicrofluidic device® high throughput screening system (HTS) by Caliper Technologies, Mountain View, Calif. or the HP/Agilent technologies Bioanalyzer using LabChip™ technology by Caliper Technologies Corp. can be adapted for use in the present invention.

In an alternate embodiment, conformational changes are detected by coupling the polypeptides or complexes of the invention to an electrical readout, e.g., to a chemically coupled field effect transistor (a CHEM-FET) or other appropriate system for detecting changes in conductance or other electrical properties brought about by a conformational shift by the protein of the invention.

Further Details Regarding Methods of Monitoring Polycystin-2L1 and/or Polycystin-1L3 Induced Behavior or Physiological Response in Animal Models In addition to the various biological and biochemical sample-based screening methods noted herein, the invention also encompasses testing for Polycystin-2L1/PKD2L1 and/or polycystin-1L3/PKD1L3 activity in response to test compounds, in vivo. In one embodiment, this is accomplished by introducing a heterologous PKD2L1 or PKD1L3 gene into an animal and expressing an encoded heterologous polypeptide in a taste bud of the animal, and/or in neurons in contact with the CSF, kidney cells, or other relevant targets for cellular expression (optionally including any cell or tissue type that naturally expresses PKD2L1 or PKD1L3). A putative polycystin-2L1 or polycystin-1L3 tastant or modulator is provided to the animal, and one or more feeding behavior or physiological response of the animal is monitored in response to the presence of the putative polycystin-2L1 taste receptor tastant.

Optionally, the animal is a knock-out animal that has a reduced or eliminated function of an endogenous Polycystin-2L1 or polycystin-1L3, e.g., in taste bud cells or in neuronal cells that contact the CSF. Knock out animals are useful both for studies of PKD2L1/polycystin-2L1 and/or or polycystin-1L3/PKD1L3 function (for example, confirmation that an animal lacking PKD2L1 or PKD1L3 is deficient with respect to one or more taste perceptions, CSF pH monitoring functions, etc.) and as a target for delivery of a heterologous PKD2L1 or PKD1L3 gene. That is, in one aspect, the animal is made transgenic with a PKD2L1 or PKD1L3 gene of interest. For example, a PKD2L1 knock-out mouse that comprises a human transgene for human PKD2L1 will display a response to polycystin-2L1 tastants and modulators similar to a human, providing a good model system for studying response to polycystin-2L1 tastants and modulators. Similarly, a PKD1L3 knock-out mouse that comprises a human transgene for human PKD1L3 will display a response to polycystin-1L3 tastants and modulators similar to a human, providing a good model system for studying response to polycystin-1L3 tastants and modulators. Double knock outs of PKD2L1 and PKD1L3 are also useful for providing both genes from a heterologous (e.g., human) source. The heterologous gene(s) can be placed under the control of a heterologous promoter(s) that is active in taste bud cells, e.g., a polycystin-2L1taste receptor gene promoter, a polycystin-1L3 gene promoter, a T1R-gene promoter, T2R-gene promoter, TRPM5- gene promoter, a PLCB2 gene promoter, a repeater gene promoter, a gustducin gene promoter, a Gi2 gene promoter, a cytokeratin-19 gene promoter, or another promoter for a gene that is naturally selectively expressed in a taste receptor cell of the tongue or palate epithelium.

Feeding behavior or physiological response(s) of the animal in response to putative tastants and/or modulators can be monitored by available methods. For example, animals (e.g., a transgenic PKD2L1 knock out mouse that comprises a human PKD2L1 gene, or other configuration as noted above) will lick a device (stick, tube, plate, etc.) coated with a tastant, if the tastant is perceived as pleasurable to the animal. By monitoring increased (or decreased) licking behavior on such devices, the effect of a putative tastant or modulator on feeding behavior can be determined. Similarly, a putative tastant or modulator can be dissolved in a taste neutral fluid such as water and supplied to the animal (e.g., using a water bottle) to determine if drinking behavior increases, or if the fluid with the putative tastant is drunk preferentially (or avoided) as compared to the neutral fluid. For example, a neutrally flavored "control" can be a water bottle, while a test compound flavored "experimental" bottle can be placed in a control bottle. If the animal (mouse, rabbit, rat, etc.) feeds preferentially on the experimental bottle, then the animal can taste the test compound and perceives the flavor as pleasurable. If the experimental and control bottle are drunk equally, then the animal likely cannot taste the test compound. If the experimental bottle is drunk less than the control, then the animal can likely detect the test compound, and may detect it as being unpleasant. Similar experiments can be performed with a food source flavored with the test compound. Physiological responses that can be monitored in such animals also can include respiration rate, oxygen consumption, blood or urine pH, or the like. Measuring these responses utilizes standard techniques.

Modulatory activity can be similarly determined. That is, a potential modulator can be administered to the animal (e.g., applied to the taste bud, injected, or supplied in food or drink) and the increase or decrease in feeding/drinking/licking behavior towards a known sour tastant (sour) can be detected, or a physiological response can be detected, essentially as above. If administration of the modulator results in an increase in feeding/drinking/licking behavior towards the known tastant, or in a physiological response, then the modulator potentiates the response of that taste quality or physiological response. For example, if feeding/drinking/licking is decreased, then it likely inhibits activity of an attractive taste modality, or enhances activity of an aversive taste modality. Either activity can be useful, depending on whether an increase in feeding/drinking is desirable (as in certain livestock yield applications or to reduce adverse flavor effects of acid preservatives), or a decrease in feeding/drinking is desirable (e.g., to treat obesity, metabolic syndrome, high blood pressure, or the like by reducing calorie intake). Examples of modulators include taste or pH receptor agonists, enhancers, antagonists, inverse agonists, etc.

Behavioral Systems

As noted, a further aspect of the invention monitors animal behavior upon application of potential tastants or taste cell modulators. These systems include a non-human animal comprising a heterologous PKD2L1 or PKD1L3 gene that is expressed in a taste bud of the animal and a source of a putative polycystin-2L1 or polycystin-1L3 taste receptor tastant that is accessible to the animal. The system further includes a detector that detects a feeding behavior of the animal in response to the presence of the putative tastant.

Here again, the animal is typically a knock-out animal (e.g., a mouse) deficient in endogenous polycystin-2L1 or polycystin-1L3 polypeptide expression, that expresses a heterologous human polycystin-2L1 or polycystin-1L3 polypeptide. The source can include any of the configurations noted above with respect to the related methods, e.g., a lickable device, a fluid source comprising the tastant, or a food source comprising the tastant.

The detector will typically include a camera or motion sensor that monitors movement of the animal. Alternately, lickable devices can detect pressure against the device through conventional strain measurement devices, or electronically by detecting the completion of a circuit upon licking, or optically by detecting tongue movement. It is also possible to inset electrodes in muscles controlling oromotor activity and monitor their contraction/relaxation as a surrogate for feeding and gagging behavior.

An analysis module, e.g., a computer analyzes information from the detector and can statistically compile information regarding feeding/licking/drinking behavior. The analysis module can include a user viewable display that displays the results of the analysis to a user, e.g., a GUI.

Making Knock-Out Animals and Transgenics

A transgenic animal is typically an animal that has had DNA introduced into one or more of its cells artificially. This is most commonly done in one of two ways. First, DNA can be integrated randomly by injecting it into the pronucleus of a fertilized ovum. In this case, the DNA can integrate anywhere in the genome. In this approach, there is no need for homology between the injected DNA and the host genome. Second, targeted insertion can be accomplished by introducing heterologous DNA into embryonic stem (ES) cells and selecting for cells in which the heterologous DNA has undergone homologous recombination with homologous sequences of the cellular genome. Typically, there are several kilobases of homology between the heterologous and genomic DNA, and positive selectable markers (e.g., antibiotic resistance genes) are included in the heterologous DNA to provide for selection of transformants. In addition, negative selectable markers (e.g., "toxic" genes such as barnase) can be used to select against cells that have incorporated DNA by non-homologous recombination (i.e., random insertion).

One common use of targeted insertion of DNA is to make knock-out mice. Typically, homologous recombination is used to insert a selectable gene driven by a constitutive promoter into an essential exon of the gene that one wishes to disrupt (e.g., the first coding exon). To accomplish this, the selectable marker is flanked by large stretches of DNA that match the genomic sequences surrounding the desired insertion point. Once this construct is electroporated into ES cells, the cells' own machinery performs the homologous recombination. To make it possible to select against ES cells that incorporate DNA by non-homologous recombination, it is common for targeting constructs to include a negatively selectable gene outside the region intended to undergo recombination (typically the gene is cloned adjacent to the shorter of the two regions of genomic homology). Because DNA lying outside the regions of genomic homology is lost during homologous recombination, cells undergoing homologous recombination cannot be selected against, whereas cells undergoing random integration of DNA often can. A commonly used gene for negative selection is the herpes virus thymidine kinase gene, which confers sensitivity to the drug gancyclovir.

Following positive selection and negative selection if desired, ES cell clones are screened for incorporation of the construct into the correct genomic locus. Typically, one designs a targeting construct so that a band normally seen on a Southern blot or following PCR amplification becomes replaced by a band of a predicted size when homologous recombination occurs. Since ES cells are diploid, only one allele is usually altered by the recombination event so, when appropriate targeting has occurred, one usually sees bands representing both wild type and targeted alleles.

The embryonic stem (ES) cells that are used for targeted insertion are derived from the inner cell masses of blastocysts (early mouse embryos). These cells are pluripotent, meaning they can develop into any type of tissue.

Once positive ES clones have been grown up and frozen, the production of transgenic animals can begin. Donor females are mated, blastocysts are harvested, and several ES cells are injected into each blastocyst. Blastocysts are then implanted into a uterine horn of each recipient. By choosing an appropriate donor strain, the detection of chimeric offspring (i.e., those in which some fraction of tissue is derived from the transgenic ES cells) can be as simple as observing hair and/or eye color. If the transgenic ES cells do not contribute to the germline (sperm or eggs), the transgene cannot be passed on to offspring.

Transgenic animals are a useful tool for studying gene function and testing tastants and modulators. Human (or other selected) PKD2L1 or PKD1L3 genes can be introduced in place of endogenous PKD2L1 or PKD1L3 genes of a laboratory animal, making it possible to study function of the human (or other) taste or pH receptor in the easily manipulated and studied laboratory animal. It will be appreciated that there is not precise correspondence between receptor function of different animals (humans and mice perceive aspartame differently, for example), making the ability to study the human or other receptor of interest particularly useful. Although similar genetic manipulations can be performed in tissue culture, the interaction of PKD2L1/PKD1L3 and polycystin-2L1/polycystin-1L3 in the context of an intact organism provides a more complete and physiologically relevant picture of function than could be achieved in simple cell-based screening assays.

Further Details Regarding Cells Comprising PKD2L1/Polycystin-2L1/PKD1L3/Polycystin-1L3

As already noted, for several embodiments, biological samples to be tested for PKD2L1/PKD1L3 expression or polycystin-2L1/polycystin-1L3 expression or concentration are cells or are derived from cell preparations. The cells can be those associated with PKD2L1/polycystin 2L1 expression in vivo, such as taste bud, neuronal, or kidney cells. Alternately, the cells can be derived from a taste bud, neuronal or kidney cell, e.g., through culture.

However, one feature of the invention is the production of recombinant cells, e.g., expressing a heterologous PKD2L1/PKD1L3 gene. In these embodiments, the biological sample to be tested is derived from the recombinant cell, which is selected largely for ease of culture and manipulation. The cells can be, e.g., human, rodent, insect, *Xenopus*, etc. and will typically be a cell in culture (or an oocyte in the case of *Xenopus*).

PKD2L1/PKD1L3 nucleic acids are typically introduced into cells in cloning and/or expression vectors to facilitate introduction of the nucleic acid and expression of PKD2L1/PKD1L3 to produce polycystin-2L1/polycystin-3L1. Vectors include, e.g., plasmids, cosmids, viruses, YACs, bacteria, poly-lysine, etc. A "vector nucleic acid" is a nucleic acid molecule into which heterologous nucleic acid is optionally inserted which can then be introduced into an appropriate host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) artificial chromosomes. "Expression vectors" are vectors that comprise elements that provide for or facilitate transcription of nucleic acids which are cloned into the vectors. Such elements can include, e.g., promoters and/or enhancers operably coupled to a nucleic acid of interest.

In general, appropriate expression vectors are known in the art. For example, pET-14b, pCDNA1 Amp, and pVL1392 are available from Novagen and Invitrogen and are suitable vectors for expression in *E. coli*, COS cells and baculovirus infected insect cells, respectively. pcDNA-3, pEAK, and vectors that permit the generation of PKD2L1/PKD1L3 RNA for in vitro and in vivo expression experiments (e.g., in vitro translations and *Xenopus* oocyte injections) are also useful. These vectors are illustrative of those that are known in the art. Suitable host cells can be any cell capable of growth in a suitable media and allowing purification of the expressed protein. Examples of suitable host cells include bacterial cells, such as *E. coli, Streptococci, Staphylococci, Streptomyces* and *Bacillus subtilis* cells; fungal cells such as yeast cells, e.g., *Pichia*, and *Aspergillus* cells; insect cells such as *Drosophila* S2 and *Spodoptera* Sf9 cells, mammalian cells such as CHO, COS, and HeLa; and even plant cells.

Cells are transformed with PKD2L1 and/or PKD1L3 genes according to standard cloning and transformation methods. Polycystins can also be isolated from resulting recombinant cells using standard methods. General texts which describe molecular biological techniques for making nucleic acids, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning-A Laboratory Manual* (3nd Ed.), Vol. 1-3, Cold Spring Harbor Laboratory, Cold Spring Harbor, N.Y., 2000 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")).

In addition, a plethora of kits are commercially available for the preparation, purification and cloning of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms, or the like.

As noted, typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (above). A catalogue of Bacteria and Bacteriophages useful for cloning is provided, e.g., by the ATCC, e.g., *The ATCC Catalogue of Bacteria and Bacteriophage* published yearly by the ATCC. Additional basic procedures for sequencing, cloning and other aspects of molecular biology and underlying theoretical considerations are also found in Watson et al. (1992) *Recombinant DNA Second Edition, Scientific American Books, NY.*

In addition, essentially any nucleic acid (and virtually any labeled nucleic acid, whether standard or non-standard) can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); and Atlas and Parks (eds) *The Handbook of Microbiological Media* (1993) CRC Press, Boca Raton, Fla.

Additional Details Regarding Protein Purification and Handling

Purification of polycystin-2L1 and/or polycystin-1L3, can be accomplished using known techniques. Generally, the transformed cells expressing polycystin-2L1 and/or polycystin-1 L3 are lysed, crude purification occurs to remove debris and some contaminating proteins, followed by chromatography to further purify the protein to the desired level of purity. Cells can be lysed by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during intracellular synthesis, isolation or purification.

In general, polycystin 2L1 and/or polycystin-1L3 polypeptides, can be purified, either partially (e.g., achieving a 5×, 10×, 100×, 500×, or 1000× or greater purification), or even substantially to homogeneity (e.g., where the protein is the main component of a solution, typically excluding the solvent (e.g., water or DMSO) and buffer components (e.g., salts and stabilizers) that the polypeptide is suspended in, e.g., if the polypeptide is in a liquid phase), according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against polycyctin 2L1 and/or polycystin-1L3 are used as purification reagents, e.g., for affinity-based purification. Once purified, partially or to homogeneity, as desired, the polypeptides are optionally used e.g., as assay components, therapeutic reagents or as immunogens for antibody production.

In addition to other references noted herein, a variety of purification/protein purification methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Rydens (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Those of skill in the art will recognize that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

PKD2L1/PKD1L3 nucleic acids optionally comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) Cell 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the sequence of the invention is useful to facilitate purification.

Cell Rescue—Treatment

In one aspect, the invention includes rescue of a cell that is defective in function of one or more endogenous polycystin genes (e.g., PKD2L1/PKD1L3) or polypeptides (e.g., polycystin 2-L1, polycystin-1L3). This can be accomplished simply by introducing a new copy of the gene (or a heterologous nucleic acid that expresses the relevant protein) into a cell. Other approaches, such as homologous recombination to repair the defective gene (e.g., via chimeraplasty) can also be performed. In any event, rescue of function can be measured, e.g., in any of the assays noted herein. Indeed, this can be used as a general method of screening cells in vitro for activity. Accordingly, in vitro rescue of function is useful in this context for the myriad in vitro screening methods noted above, e.g., for the identification of tastants or modulators in cells. The cells that are rescued can include cells in culture, (including primary or secondary cell culture from patients, as well as cultures of well-established cells). Where the cells are isolated from a patient, this has additional diagnostic utility in establishing which sequence is defective in a patient that presents with a tasting defect.

In another aspect, cell rescue occurs in a patient, e.g., a human or veterinary patient, e.g., to remedy a tastant or CSF sensor defect. Thus, one aspect of the invention is gene therapy to remedy tasting or CSF pH sensor defects (or even simply to enhance tastant discrimination), in human or veterinary applications. In these applications, the nucleic acids of the invention are optionally cloned into appropriate gene therapy vectors (and/or are simply delivered as naked or liposome-conjugated nucleic acids), which are then delivered (generally topically to the taste buds, where these are the target, but optionally systemically), optionally in combination with appropriate carriers or delivery agents. Proteins can also be delivered directly, but delivery of the nucleic acid is typically preferred in applications where stable expression is desired.

Vectors for administration typically comprise PKD2L1 and/or PKD1L3 genes under the control of a promoter that is expressed in taste bud, neuronal or kidney cells. These can include native PKD2L1 and/or PKD1L3 promoters, or other taste bud or neuronal or kidney specific promoters such as a T1R-gene promoter, a T2R-gene promoter, a TRPM5-gene promoter, a PLCB2 gene promoter, a repeater gene promoter, a gustducin gene promoter, a Gi2 gene promoter, a cytokeratin-19 gene promoter, or a promoter for another gene that is naturally selectively expressed in a taste receptor cell of the tongue or palate epithelium. In the case of expression in neuronal cells (e.g., in contact with the CSF), a variety of genes are known to be promiscuously expressed in central or peripheral neurons. For example, Gray PA Fu H et al (2004) "Mouse Brain Organization Revealed through Direct Genome Scale Transcription Factor Expression Analysis." *Science* 306:2255-57 describe genes that can be used as sources of promoters. Similarly, Ruan et al (2005) "Nuclear receptors and their coregulators in kidney" *Kidney Int.* 68(6): 2444-61 describe appropriate sources of promoters for expression in kidney.

Compositions for administration, e.g., comprise a therapeutically effective amount of the gene therapy vector or other relevant nucleic acid, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering gene therapy vectors for topical use are well known in the art and can be applied to administration of the nucleic acids of the invention.

Therapeutic compositions comprising one or more nucleic acid of the invention are optionally tested in one or more appropriate in vitro and/or in vivo animal model of disease, to confirm efficacy, tissue metabolism, and to estimate dosages, according to methods well known in the art. In particular, dosages can initially be determined by activity, stability or other suitable measures of the formulation.

Administration is by any of the routes normally used for introducing a molecule into ultimate contact with cells of interest (taste bud, tongue, palate epithelium, neuronal cells in contact with the CSF, kidney cells, etc.). Practitioners can select an administration route of interest based on the cell target. For example, topical administration or direct injection into the taste buds or other tissues of the tongue or palette epithelium is simplest and therefore preferred for these targets. Similarly, injection into the CSF can be used where the target is neuronal cells in contact with the CSF. The nucleic acids of the invention are administered in any suitable manner, optionally with one or more pharmaceutically acceptable carriers. Suitable methods of administering such nucleic acids in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Compositions can be administered by a number of routes including, but not limited to: oral (in this case, topical and oral can be the same or different, e.g., topical delivery to the taste buds can be oral, as can systemic administration by the GI tract), intravenous, intraperitoneal, intramuscular, transdermal, subcutaneous, topical, sublingual, spinal, or rectal administration. Compositions can be administered via liposomes (e.g., topically), or via topical delivery of naked DNA or viral vectors. Such administration routes and appropriate formulations are generally known to those of skill in the art.

The compositions, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

The dose administered to a patient, in the context of the present invention, is sufficient to effect a beneficial therapeutic response in the patient over time, or, e.g., to provide sweet or glutamate tastant discrimination as perceived by the patient in an objective sweet or glutamate tastant test. The dose is determined by the efficacy of the particular vector, or other formulation, and the activity, stability or serum half-life of the polypeptide which is expressed, and the condition of the patient, as well as the body weight or surface area of the patient to be treated. The size of the dose is also determined by the existence, nature, and extent of any adverse side-effects that accompany the administration of a particular vector, formulation, or the like in a particular patient. In determining the effective amount of the vector or formulation to be administered in the treatment of disease, the physician evaluates local expression in the taste buds, or circulating plasma levels, formulation toxicities, progression of the relevant disease, and/or where relevant, the production of antibodies to proteins encoded by the polynucleotides. The dose administered, e.g., to a 70 kilogram patient are typically in the range equivalent to dosages of currently-used therapeutic proteins, adjusted for the altered activity or serum half-life of the relevant composition. The vectors of this invention can supplement treatment conditions by any known conventional therapy (e.g., diet restriction, etc.).

For administration, formulations of the present invention are administered at a rate determined by the LD-50 of the relevant formulation, and/or observation of any side-effects of the vectors of the invention at various concentrations, e.g., as applied to the mass or topical delivery area and overall health of the patient. Administration can be accomplished via single or divided doses.

If a patient undergoing treatment develops fevers, chills, or muscle aches, he/she receives the appropriate dose of aspirin, ibuprofen, acetaminophen or other pain/fever controlling drug. Patients who experience reactions to the compositions, such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

Detecting Polymorphisms

In one aspect, the invention includes detecting a polymorphism in a PKD2L1 or PKD1L3 gene (or a nucleic acid in linkage disequilibrium with such a polymorphism) to detect a taste receptor or CSF pH sensor or other abnormality caused by polymorphisms in these genes. CSF sensor abnormalities can lead, e.g., to disorders related to respiration, including sudden infant death syndrome (SIDS), sleep apnea, high altitude hypersensitivity, or the like. A "polymorphism" is a locus that is variable; that is, within a population, the nucleotide sequence at a polymorphism has more than one version or allele. The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. One example of a polymorphism is a "single nucleotide polymorphism" (SNP), which is a polymorphism at a single nucleotide position in a genome (the nucleotide at the specified position varies between individuals or populations). An allele "positively" correlates with a trait when it is linked to it and when presence of the allele is an indictor that the trait or trait form will occur in an individual comprising the allele. An allele negatively correlates with a trait when it is linked to it and when presence of the allele is an indicator that a trait or trait form will not occur in an individual comprising the allele.

In the present case, gene for tastant, pH sensor and other defects is identified (PKD2L1, PKD1L3). Polymorphisms within or linked to (in linkage disequilibrium with) these genes likely correlate to altered taste perception, pH sensor activity and the like. Thus, pH sensor defects, tastant defects or other abnormalities can be detected by detecting polymorphisms in the gene.

In general, markers corresponding to polymorphisms between members of a population can be detected by numerous methods well-established in the art (e.g., PCR-based sequence specific amplification, restriction fragment length polymorphisms (RFLPs), isozyme markers, northern analysis, allele specific hybridization (ASH), array based hybridization, amplified variable sequences of the genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. Any of these methods are readily adapted to high throughput analysis.

Additional Details Regarding Sequence Variations

A number of particular polycystin-2L1 and polycystin-1L3 polypeptides and coding nucleic acids are described herein by sequence (See, e.g., the Examples section below). These polypeptides and coding nucleic acids can be modified, e.g., by mutation as described herein, or simply by artificial synthesis of a desired variant. Several types of example variants are described below.

Splice Variants

Given the significant number of exons found, e.g., in PKD2L1 and PKD1L3, the presence of splice variants in taste receptor cells is likely. These can be expressed alone or in combination and can be detected or monitored by analysis of taste cell mRNA using PKD2L1 or PKD1L3 exon-specific primers and the polymerase chain reaction.

Silent Variations

Due to the degeneracy of the genetic code, any of a variety of nucleic acids sequences encoding polypeptides of the invention are optionally produced, some which can bear lower levels of sequence identity to the PKD2L1 or PKD1L3 nucleic acids in the Examples below. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAG GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |

TABLE 1-continued

Codon Table

| Amino acids | | | Codon |
|---|---|---|---|
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the co dons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations", discussed below. One of skill will recognize that each codon in a nucleic acid (except ATG, which is ordinarily the only codon for methionine) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a polycystin polypeptide of the invention. All such variations of every nucleic acid herein are specifically provided and described by consideration of the sequence in combination with the genetic code. One of skill is fully able to make these silent substitutions using the methods herein.

Conservative Variations

"Conservatively modified variations" or, simply, "conservative variations" of a particular nucleic acid sequence or polypeptide are those which encode identical or essentially identical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another.

TABLE 2

Conservative Substitution Groups

| | | |
|---|---|---|
| 1 Alanine (A) | Serine (S) | Threonine (T) |
| 2 Aspartic acid (D) | Glutamic acid (E) | |
| 3 Asparagine (N) | Glutamine (Q) | |
| 4 Arginine (R) | Lysine (K) | |
| 5 Isoleucine (I) | Leucine (L) | Methionine (M) Valine (V) |
| 6 Phenylalanine (F) | Tyrosine (Y) | Tryptophan (W) |

Thus, "conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

Finally, the addition or deletion of sequences which do not alter the encoded activity of a nucleic acid molecule, such as the addition or deletion of a non-functional sequence, is a conservative variation of the basic nucleic acid or polypeptide.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Antibodies

In another aspect, antibodies to polycystin-2L1 and polycystin-1L3 polypeptides can be generated using methods that are well known. The antibodies can be utilized for detecting and/or purifying polycystin-2L1 and/or polycystin-1 L3 polypeptides e.g., in situ to monitor localization of receptor, or simply in a biological sample of interest. Antibodies can optionally discriminate the polycystin 2L1 or polycystin-1L3 polypeptides from other polycystin homologues, and/or can be used in biosensor applications. Antibodies can also be used to block function of polycystin-2L1 and/or polycystin-1L3, in vivo, in situ or in vitro. As used herein, the term "antibody" includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a polycystin 2L1 or polycystin-1L3 polypeptide encoded by one of the disclosed sequences or conservative variant or fragment thereof, various host animals may be immunized by injection with the polypeptide, or a portion thereof. Such host animals may include, but are not limited to, rabbits, mice and rats, to name but a few. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Nat'l. Acad. Sci. USA* 81:6851-6855, 1984; Neuberger et al., *Nature* 312:604-608, 1984; Takeda et al., *Nature* 314:452-454, 1985) by splicing the genes from a mouse antibody molecule of appropriate antigen specificity, together with genes from a human antibody molecule of appropriate biological activity, can be used. A chimeric antibody is a molecule in which different portions are derived from different animal species, such as those having a variable or hypervariable region derived from a murine mAb and a human immunoglobulin constant region.

Alternatively, techniques described for the production of single-chain antibodies (U.S. Pat. No. 4,946,778; Bird, *Science* 242:423-426, 1988; Huston et al., *Proc. Nat'l. Acad. Sci. USA* 85:5879-5883, 1988; and Ward et al., *Nature* 334:544-546, 1989) can be adapted to produce differentially expressed gene-single chain antibodies. Single chain antibodies are formed by linking the heavy and light chain fragments of the Fv region via an amino acid bridge, resulting in a single-chain polypeptide.

In one aspect, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments which recognize specific epitopes may be generated by known techniques. For example, such fragments include, but are not limited to, the F(ab')$_2$ fragments, which can be produced by pepsin digestion of the antibody molecule, and the Fab fragments, which can be generated by reducing the disulfide bridges of the F(ab')$_2$ fragments. Alternatively, Fab expression libraries may be constructed (Huse et al., *Science* 246:1275-1281, 1989) to allow rapid and easy identification of monoclonal Fab fragments with the desired specificity.

The protocols for detecting and measuring the expression of the described polycystin 2L1 polypeptides herein, using the above mentioned antibodies, are well known in the art. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific and patent literature, and many employed commercially.

One method, for ease of detection, is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule and incubated for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay, in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the protein expressed by the gene of interest.

The most commonly used reporter molecules in this type of assay are either enzymes, fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product, rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of PLAB which is present in the serum sample.

Alternately, fluorescent compounds, such as fluorescein and rhodamine, can be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In one example, peptides for PKD2L1 and PKD1L3 were generated, and conjugated to carriers. Rabbits were immunized to make polyclonal antibodies. These antibodies were shown to bind PC-2-L1 and PC-1-L3 in situ (see also, Example 3, herein).

Regulating Gene Expression of PKD2L1/PKD1L3

Gene expression (e.g., transcription and/or translation) of PKD2L1 or PKD1 L3 can be regulated using any of a variety of techniques known in the art. For example, gene expression can be inhibited using an antisense nucleic acid or an interfering RNA. Inhibition of expression in particular cell-types can be used for further studying the in vitro or in vivo role of these genes, and/or as a mechanism for treating a condition caused by overexpression of a PKD1 L3 or PKD2L1 gene, and/or for treating a dominant effect caused by a particular allele of such a gene (polycystic kidney disease is caused by such dominant alleles in related PKD genes).

For example, use of antisense nucleic acids is well known in the art. An antisense nucleic acid has a region of complementarity to a target nucleic acid, e.g., a target gene, mRNA, or cDNA. Typically, a nucleic acid comprising a nucleotide sequence in a complementary, antisense orientation with respect to a coding (sense) sequence of an endogenous gene is introduced into a cell. The antisense nucleic acid can be RNA, DNA, a PNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for any gene whose coding sequence is known or can be determined by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. Nos. 6,500,615; 6,498,035; 6,395,544; 5,563,050; E. Schuch et al (1991) *Symp Soc. Exp Biol* 45:117-127; de Lange et al., (1995) *Curr Top Microbiol Immunol* 197:57-75; Hamilton et al. (1995) *Curr Top Microbiol Immunol* 197:77-89; Finnegan et al., (1996) *Proc Natl Acad Sci USA* 93:8449-8454; Uhlmann and A. Pepan (1990), *Chem. Rev.* 90:543; P. D. Cook (1991), *Anti-Cancer Drug Design* 6:585; J. Goodchild, Bioconjugate Chem. 1 (1990) 165; and, S. L. Beaucage and R. P. Iyer (1993), *Tetrahedron* 49:6123; and F. Eckstein, Ed. (1991), *Oligonucleotides and Analogues—A Practical Approach*, IRL Press.

Gene expression can also be inhibited by RNA silencing or interference. "RNA silencing" refers to any mechanism through which the presence of a single-stranded or, typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g., histone acetylation and heterochromatin formation leading to inhibition of transcription of the target mRNA).

The term "RNA interference" ("RNAi," sometimes called RNA-mediated interference, post-transcriptional gene silencing, or quelling) refers to a phenomenon in which the presence of RNA, typically double-stranded RNA, in a cell results in inhibition of expression of a gene comprising a sequence identical, or nearly identical, to that of the double-stranded RNA. The double-stranded RNA responsible for inducing RNAi is called an "interfering RNA." Expression of the gene is inhibited by the mechanism of RNAi as described below, in which the presence of the interfering RNA results in degradation of mRNA transcribed from the gene and thus in decreased levels of the mRNA and any encoded protein.

The mechanism of RNAi has been and is being extensively investigated in a number of eukaryotic organisms and cell types. See, for example, the following reviews: McManus and Sharp (2002) "Gene silencing in mammals by small interfering RNAs" Nature Reviews Genetics 3:737-747; Hutvagner and Zamore (2002) "RNAi: Nature abhors a double strand" Curr Opin Genet & Dev 200:225-232; Hannon (2002) "RNA interference" Nature 418:244-251; Agami (2002) "RNAi and related mechanisms and their potential use for therapy" Curr Opin Chem Biol 6:829-834; Tuschl and Borkhardt (2002) "Small interfering RNAs: A revolutionary tool for the analysis of gene function and gene therapy" Molecular Interventions 2:158-167; Nishikura (2001) "A short primer on RNAi: RNA-directed RNA polymerase acts as a key catalyst" Cell 107:415-418; and Zamore (2001) "RNA interference: Listening to the sound of silence" Nature Structural Biology 8:746-750. RNAi is also described in the patent literature; see, e.g., CA 2359180 by Kreutzer and Limmer entitled "Method and medicament for inhibiting the expression of a given gene"; WO 01/68836 by Beach et al. entitled "Methods and compositions for RNA interference"; WO 01/70949 by Graham et al. entitled "Genetic silencing"; and WO 01/75164 by Tuschl et al. entitled "RNA sequence-specific mediators of RNA interference."

In brief, double-stranded RNA introduced into a cell (e.g., into the cytoplasm) is processed, for example by an RNAse III-like enzyme called Dicer, into shorter double-stranded fragments called small interfering RNAs (siRNAs, also called short interfering RNAs). The length and nature of the siRNAs produced is dependent on the species of the cell, although typically siRNAs are 21-25 nucleotides long (e.g., an siRNA may have a 19 base pair duplex portion with two nucleotide 3' overhangs at each end). Similar siRNAs can be produced in vitro (e.g., by chemical synthesis or in vitro transcription) and introduced into the cell to induce RNAi. The siRNA becomes associated with an RNA-induced silencing complex (RISC). Separation of the sense and antisense strands of the siRNA, and interaction of the siRNA antisense strand with its target mRNA through complementary base-pairing interactions, optionally occurs. Finally, the mRNA is cleaved and degraded.

Expression of a target gene in a cell can thus be specifically inhibited by introducing an appropriately chosen double-stranded RNA into the cell. Guidelines for design of suitable interfering RNAs are known to those of skill in the art. For example, interfering RNAs are typically designed against exon sequences, rather than introns or untranslated regions. Characteristics of high efficiency interfering RNAs may vary by cell type. For example, although siRNAs may require 3' overhangs and 5' phosphates for most efficient induction of RNAi in Drosophila cells, in mammalian cells blunt ended siRNAs and/or RNAs lacking 5' phosphates can induce RNAi as effectively as siRNAs with 3' overhangs and/or 5' phosphates (see, e.g., Czauderna et al. (2003) "Structural variations and stabilizing modifications of synthetic siRNAs in mammalian cells" Nucl Acids Res 31:2705-2716). As another example, since double-stranded RNAs greater than 30-80 base pairs long activate the antiviral interferon response in mammalian cells and result in non-specific silencing, interfering RNAs for use in mammalian cells are typically less than 30 base pairs (for example, Caplen et al. (2001) "Specific inhibition of gene expression by small double-stranded RNAs in invertebrate and vertebrate systems" Proc. Natl. Acad. Sci. USA 98:9742-9747, Elbashir et al. (2001) "Duplexes of 21-nucleotide RNAs mediate RNA interference in cultured mammalian cells" Nature 411:494-498 and Elbashir et al. (2002) "Analysis of gene function in somatic mammalian cells using small interfering RNAs" Methods 26:199-213 describe the use of 21 nucleotide siRNAs to specifically inhibit gene expression in mammalian cell lines, and Kim et al. (2005) "Synthetic dsRNA Dicer substrates enhance RNAi potency and efficacy" Nature Biotechnology 23:222-226 describes use of 25-30 nucleotide duplexes). The sense and antisense strands of a siRNA are typically, but not necessarily, completely complementary to each other over the double-stranded region of the siRNA (excluding any overhangs). The antisense strand is typically completely complementary to the target mRNA over the same region, although some nucleotide substitutions can be tolerated (e.g., a one or two nucleotide mismatch between the antisense strand and the mRNA can still result in RNAi, although at reduced efficiency). The ends of the double-stranded region are typically more tolerant to substitution than the middle; for example, as little as 15 bp (base pairs) of complementarity between the antisense strand and the target mRNA in the context of a 21 mer with a 19 bp double-stranded region has been shown to result in a functional siRNA (see, e.g., Czauderna et al. (2003) "Structural variations and stabilizing modifications of synthetic siRNAs in mammalian cells" Nucl Acids Res 31:2705-2716). Any overhangs can but need not be complementary to the target mRNA; for example, TT (two 2'-deoxythymidines) overhangs are frequently used to reduce synthesis costs.

Although double-stranded RNAs (e.g., double-stranded siRNAs) were initially thought to be required to initiate RNAi, several recent reports indicate that the antisense strand of such siRNAs is sufficient to initiate RNAi. Single-stranded antisense siRNAs can initiate RNAi through the same pathway as double-stranded siRNAs (as evidenced, for example, by the appearance of specific mRNA endonucleolytic cleavage fragments). As for double-stranded interfering RNAs, characteristics of high-efficiency single-stranded siRNAs may vary by cell type (e.g., a 5' phosphate may be required on the antisense strand for efficient induction of RNAi in some cell types, while a free 5' hydroxyl is sufficient in other cell types capable of phosphorylating the hydroxyl). See, e.g., Martinez et al. (2002) "Single-stranded antisense siRNAs guide target RNA cleavage in RNAi" Cell 110:563-574; Amarzguioui et al. (2003) "Tolerance for mutations and chemical modifications in a siRNA" Nucl. Acids Res. 31:589-595; Holen et al. (2003) "Similar behavior of single-strand and double-strand siRNAs suggests that they act through a common RNAi pathway" Nucl. Acids Res. 31:2401-2407; and Schwarz et al. (2002) Mol. Cell 10:537-548.

Due to currently unexplained differences in efficiency between siRNAs corresponding to different regions of a given target mRNA, several siRNAs are typically designed and tested against the target mRNA to determine which siRNA is most effective. Interfering RNAs can also be produced as small hairpin RNAs (shRNAs, also called short hairpin RNAs), which are processed in the cell into siRNA-like molecules that initiate RNAi (see, e.g., Siolas et al. (2005) "Synthetic shRNAs as potent RNAi triggers" Nature Biotechnology 23:227-231).

The presence of RNA, particularly double-stranded RNA, in a cell can result in inhibition of expression of a gene comprising a sequence identical or nearly identical to that of the RNA through mechanisms other than RNAi. For example, double-stranded RNAs that are partially complementary to a target mRNA can repress translation of the mRNA without affecting its stability. As another example, double-stranded RNAs can induce histone methylation and heterochromatin formation, leading to transcriptional silencing of a gene comprising a sequence identical or nearly identical to that of the RNA (see, e.g., Schramke and Allshire (2003) "Hairpin RNAs and retrotransposon LTRs effect RNAi and chromatin-based gene silencing" Science 301:1069-1074; Kawasaki and Taira (2004) "Induction of DNA methylation and gene silencing by short interfering RNAs in human cells" Nature 431: 211-217; and Morris et al. (2004) "Small interfering RNA-induced transcriptional gene silencing in human cells" Science 305:1289-1292).

Short RNAs called microRNAs (miRNAs) have been identified in a variety of species. Typically, these endogenous RNAs are each transcribed as a long RNA and then processed to a pre-miRNA of approximately 60-75 nucleotides that forms an imperfect hairpin (stem-loop) structure. The pre-miRNA is typically then cleaved, e.g., by Dicer, to form the mature miRNA. Mature miRNAs are typically approximately 21-25 nucleotides in length, but can vary, e.g., from about 14 to about 25 or more nucleotides. Some, though not all, miRNAs have been shown to inhibit translation of mRNAs bearing partially complementary sequences. Such miRNAs contain one or more internal mismatches to the corresponding mRNA that are predicted to result in a bulge in the center of the duplex formed by the binding of the miRNA antisense strand to the mRNA. The miRNA typically forms approximately 14-17 Watson-Crick base pairs with the mRNA; additional wobble base pairs can also be formed. In addition, short synthetic double-stranded RNAs (e.g., similar to siRNAs) containing central mismatches to the corresponding mRNA have been shown to repress translation (but not initiate degradation) of the mRNA. See, for example, Zeng et al. (2003) "MicroRNAs and small interfering RNAs can inhibit mRNA expression by similar mechanisms" Proc. Natl. Acad. Sci. USA 100:9779-9784; Doench et al. (2003) "siRNAs can function as miRNAs" Genes & Dev. 17:438-442; Bartel and Bartel (2003) "MicroRNAs: At the root of plant development?" Plant Physiology 132:709-717; Schwarz and Zamore (2002) "Why do miRNAs live in the miRNP?" Genes & Dev. 16:1025-1031; Tang et al. (2003) "A biochemical framework for RNA silencing in plants" Genes & Dev. 17:49-63; Meister et al. (2004) "Sequence-specific inhibition of microRNA- and siRNA-induced RNA silencing" RNA 10:544-550; Nelson et al. (2003) "The microRNA world: Small is mighty" Trends Biochem. Sci. 28:534-540; Scacheri et al. (2004) "Short interfering RNAs can induce unexpected and divergent changes in the levels of untargeted proteins in mammalian cells" Proc. Natl. Acad. Sci. USA 101:1892-1897; Sempere et al. (2004) "Expression profiling of mammalian microRNAs uncovers a subset of brain-expressed microRNAs with possible roles in murine and human neuronal differentiation" Genome Biology 5:R13; Dykxhoorn et al. (2003) "Killing the messenger: Short RNAs that silence gene expression" Nature Reviews Molec. and Cell Biol. 4:457-467; McManus (2003) "MicroRNAs and cancer" Semin Cancer Biol. 13:253-288; and Stark et al. (2003) "Identification of *Drosophila* microRNA targets" PLoS Biol. 1:E60.

The cellular machinery involved in translational repression of mRNAs by partially complementary RNAs (e.g., certain miRNAs) appears to partially overlap that involved in RNAi, although, as noted, translation of the mRNAs, not their stability, is affected and the mRNAs are typically not degraded.

The location and/or size of the bulge(s) formed when the antisense strand of the RNA binds the mRNA can affect the ability of the RNA to repress translation of the mRNA. Similarly, location and/or size of any bulges within the RNA itself can also affect efficiency of translational repression. See, e.g., the references above. Typically, translational repression is most effective when the antisense strand of the RNA is complementary to the 3' untranslated region (3' UTR) of the mRNA. Multiple repeats, e.g., tandem repeats, of the sequence complementary to the antisense strand of the RNA can also provide more effective translational repression; for example, some mRNAs that are translationally repressed by endogenous miRNAs contain 7-8 repeats of the miRNA binding sequence at their 3' UTRs. It is worth noting that translational repression appears to be more dependent on concentration of the RNA than RNA interference does; translational repression is thought to involve binding of a single mRNA by each repressing RNA, while RNAi is thought to involve cleavage of multiple copies of the mRNA by a single siRNA-RISC complex.

Guidance for design of a suitable RNA to repress translation of a given target mRNA can be found in the literature (e.g., the references above and Doench and Sharp (2004) "Specificity of microRNA target selection in translational repression" Genes & Dev. 18:504-511; Rehmsmeier et al. (2004) "Fast and effective prediction of microRNA/target duplexes" RNA 10:1507-1517; Robins et al. (2005) "Incorporating structure to predict microRNA targets" Proc Natl Acad Sci 102:4006-4009; and Mattick and Makunin (2005) "Small regulatory RNAs in mammals" Hum. Mol. Genet. 14:R121-R132, among many others) and herein. However, due to differences in efficiency of translational repression between RNAs of different structure (e.g., bulge size, sequence, and/or location) and RNAs corresponding to different regions of the target mRNA, several RNAs are optionally designed and tested against the target mRNA to determine which is most effective at repressing translation of the target mRNA (preferably, without inducing endonucleolytic cleavage and degradation of the target mRNA).

Further Details Regarding Polycystin Variants

Any of a variety of polycystin 2L1/polycystin-1L3 polypeptides and coding PKD2L1/PKD1L3 nucleic acids can be used in the present invention. These include human polycystin-2L1/polycystin-1L3 polypeptides and coding PKD2L1/PKD1L3 genes, murine polycystin-2L1/polycystin-1L3 polypeptides and coding PKD2L1/PKD1L3 genes, and polypeptides and coding nucleic acids from a domesticated or livestock animal. Examples of such polypeptides and coding PKD2L1/PKD1L3 genes are available, including polycystin-2L1 and PKD2L1 for mice, humans and dogs. Examples of such sequences are provided in the Examples section below and are further available in public databases.

The sequence of any available PKD2L1 or PKD1L3 genes and coded polypeptides can be modified by standard methods to provide variants of such available sequences, including conservative or non-conservative variants. Any available mutagenesis procedure can be used to modify a PKD2L1 or PKD1L3 gene. Such mutagenesis procedures optionally include selection of mutant nucleic acids and polypeptides for one or more activity of interest (e.g., increased responsiveness to tastant stimuli, which can be useful in producing transgenic animals, or for biosensor applications). Procedures that can be used include, but are not limited to: site-directed point mutatgenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, and many others known to persons of skill. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like. In another class of embodiments, modification is essentially random (e.g., as in classical DNA shuffling).

Additional information regarding mutation is found in the following publications and references cited within: Arnold, *Protein engineering for unusual environments, Current Opinion in Biotechnology* 4:450-455 (1993); Bass et al., *Mutant Trp repressors with new DNA-binding specificities, Science* 242:240-245 (1988); Botstein & Shortle, *Strategies and applications of in vitro mutagenesis, Science* 229:1193-1201 (1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA*, 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Sieber, et al., *Nature Biotechnology*, 19:456-460 (2001); Smith, *In vitro mutagenesis, Ann. Rev. Genet.* 19:423-462(1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond.* A 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); and Zoller & Smith, *Oligonucleotide-directed mutagenesis: a simple method using two oligonucleotide primers and a single-stranded DNA template, Methods in Enzymol.* 154:329-350 (1987). Additional details on many of the above methods can be found in *Methods in Enzymology* Volume 154, which also describes useful controls for trouble-shooting problems with various mutagenesis methods.

Kits

In an additional aspect, the present invention provides kits embodying the methods, composition, systems or apparatus herein. Kits of the invention optionally comprise one or more of the following: (1) a composition, system, system component as described herein; (2) instructions for practicing the methods described herein, and/or for using the compositions or operating the system or system components herein; (3) one or more polycystin 2L1 polypeptide or PKD2L1 nucleic acid; (4) a container for holding components or compositions, and, (5) packaging materials.

EXAMPLES

The following Examples serve to illustrate, but not to limit the invention. One of skill will recognize a variety of non-critical parameters that can be changed to achieve essentially similar results.

Example 1

A Novel Ion Channel Preferentially Expressed In Mammalian Taste Receptor Cells (PC-2-L1/PKD2L1)

Introduction

Taste transduction is one of the most sophisticated forms of chemotransduction in animals (Avenet & Lindemann (1989)

Perspectives in taste reception. 112, 1-8; Margolskee (1993) R. Bioessays 15, 645-650). Gustatory signaling is found throughout the animal kingdom, from simple metazoans to the most complex of vertebrates; its main purpose is to provide a reliable signaling response to non-volatile ligands. Mammals are believed to have five basic types of taste modalities: salty, sour, sweet, umami (the taste of MSG), and bitter. Each of these is thought to be mediated by distinct signaling pathways leading to receptor cell depolarization, generation of a receptor or action potential, and release of neurotransmitter and synaptic activity (Roper (1989) *Ann. Rev. Neurosci.* 12:329-353). Recently, the receptors for bitter, sweet and umami were cloned and shown to be encoded by two families of G-protein coupled receptors (Nelson et al. (2001) "Mammalian sweet taste receptors" *Cell* 106(3): 381-90; Nelson et al. (2002) "An amino-acid taste receptor" *Nature* 416(6877): 199-202; Zhang et al. (2003) "Coding of sweet, bitter, and umami tastes: different receptor cells sharing similar signaling pathways" *Cell;* 112(3):293-301; Zhao et al. (2003) "The receptors for mammalian sweet and umami taste" *Cell* 115(3):255-66; Mueller et al. (2005) "The receptors and coding logic for bitter taste" *Nature* 434 (7030): 225-9. In contrast, most of the molecular components of sour or salty pathways remain unknown. Electrophysiological studies suggest that sour and salty tastants modulate taste cell function by direct entry of H+ and Na+ ions through specialized membrane channels on the apical surface of the cell. Thus, ion channels selectively expressed in taste receptor cells are ideal candidates as mediators of salt and sour tastes. Alternatively, ion channels may function as the final critical signaling component in the activation of taste cells (akin to the role of TRPM5 in sweet, umami and bitter cells; Zhang et al. (2003) "Coding of sweet, bitter, and umami tastes: different receptor cells sharing similar signaling pathways" *Cell* 112(3):293-30).

The identification and isolation of taste signaling molecules, in particular receptors, ion channels and signaling components, would allow for pharmacological and genetic modulation of taste signaling pathways. For example, availability of receptor and channel molecules (which are accessible from outside of the cell) would permit the screening for high affinity agonists, antagonists, inverse agonists, and enhancers of taste cell activity. These could then be used in the pharmaceutical and food industry to custom tune, enhance, block, or modulate different tastes. In addition, these cDNAs serve as invaluable tools in the generation of taste (tongue-brain) topographic maps of sensory coding, and the dissection of taste-induced behaviors. Here we report the cloning and characterization of a taste-specific ion channel.

Overview

To discover novel receptors, ion channels and other membrane signaling molecules involved in signal transduction in taste receptor cells, we developed a novel bioinformatics/molecular screening strategy. Our approach relied on two empirical assumptions: First, receptors and ion channels are transmembrane proteins. Second, sensory receptors in the visual, olfactory, touch and taste systems are often selectively expressed in restricted numbers of tissues. Therefore, we searched the mouse genome for transmembrane proteins, and then screened for those with restricted expression. Chosen molecules were subjected to experimental validation by PCR amplification reactions using taste tissue and in situ hybridization studies against mouse tongues.

Using a Hidden Markov Model (TMHMM 2.0) and f_TMH (UCSD Supercomputing Center, Bourne lab), we screened the entire Ensembl mouse genome database for genes encoding putative transmembrane domains. In order to determine the tissue distribution for the chosen candidate genes, we used mouse Expression Sequence Tag (EST) databases (www.ncbi.nlm.nih.gov/BLAST) to identify gene transcripts (i.e., cDNAs) expressed in 3 tissues/organs or less. PCR amplification primers were then prepared against selected cDNAs and RT-PCR reactions using mRNA from taste and non-taste tissues were carried out. Candidates preferentially expressed in taste receptor cells were used for RNA in situ hybridization against various taste papillae. This strategy led to the isolation of a novel taste-specific ion channel.

Bioinformatics Screen

Using a Hidden Markov Model (TMHMM 2.0) and f_TM-HMM (UCSD Supercomputing Center, Bourne lab) we screened the entire Ensembl mouse genome database for genes encoding transmembrane domains. In order to determine the tissue distribution for candidate cDNAs encoding transmembrane proteins, we used mouse Expression Sequence Tag (EST) databases as an expression filter (www.ncbi.nlm.nih.gov/BLAST); each cDNA expressed in 3 tissues/organs or less, was chosen for further study.

Summary of results: (1) We identified 13,742 predicted and annotated transcripts encoding candidate transmembrane domains (Ensembl version mm.30). (2) 1077 genes were selected by EST analyses as being expressed in 3 tissues or less. (3) 884 genes were chosen and subjected to taste versus non-taste RT-PCR reactions using primers against the last exon and/or the 3' untranslated region (primers were designed using http://frodo.wi.mit.edu/cgi-bin/primer3/primer3_www.cgi). (4) 26 candidates were chosen for detailed in situ analysis.

Tissue Collection & RT-PCR Screen:

In order to determine if candidate cDNAs were selectively expressed in taste receptor cells—a goal of this example—we performed RT-PCR reactions using mRNA from taste and non-taste tissue.

Peeled, hand-dissected circumvallate and foliate taste papillae from ~20 mice were collected for each mRNA extraction (total of 120 mice were used). Tissue was stored in RNAlater (Qiagen), and mRNA was extracted using Micro-FastTrack 2.0 mRNA extraction kit (Invitrogen). cDNA was synthesized using SuperScript II first-strand cDNA synthesis kit (Invitrogen) using oligo(dT) as primers. cDNA synthesis and progress was monitored by using T1R3 (Nelson et al., 2001) and GAPDH as controls.

RT-PCR experiments were performed using a minimum of two independent RT preparations, each containing a mix of circumvallate and folliate mRNA (taste mRNA). As counter-screen, we sampled each candidate cDNA in two independent RT reactions using tongue epithelium devoid of taste receptor cells (non-taste mRNA). 98 of the 884 candidates showed specific RT-PCR reaction products in taste samples but not in any of the non-taste reactions.

Data-Mining & RNA in Situ Hybridization:

Candidates shown to be selectively enriched in taste tissue by RT-PCR were examined in detail using BLAST (http://www.ncbi.nlm.nih.gov/BLAST/) and motif search engines, and subjected to RNA in situ hybridizations experiments (see methods section in Hoon et al. (1999) "Putative mammalian taste receptors: a class of taste-specific GPCRs with distinct topographic selectivity" *Cell* 96:541-51 for details on in situ preparations). Male and female mouse tongues containing different taste papillae were used in all in situ studies. Clone ID 529-30/597-8 was shown to be expressed in selective subsets of taste receptor cells. FIG. 1 shows results from the RNA in situ hybridization in circumvallate taste papillae. Note the expression in subsets of taste cells, but not in surrounding non-taste tissue.

Clone ID529-30/597-8:

This gene was (a) isolated as one of the candidates of the bioinformatics screen, (b) found to be enriched in taste papillae using our RT-PCR screen, and (c) shown to be expressed in a selective subset of taste receptor cells.

Analyses of mouse, rat, and human sequence databases showed that the clone defined by PCR primers "CloneID529-30/597-8" encodes PKD2L1, a distant member of the Polycystin Kidney Disease family of proteins (Nomura, et al. (1998) "Identification of PKDL, a novel polycystic kidney disease 2-like gene whose murine homologue is deleted in mice with kidney and retinal defects" *J. Biol. Chem.* 273: 25967-25973), referred to as the TRPP family (Lin and Corey (2005) "TRP channels in mechanosensation" Curr Opin Neurobiol. 15(3):350-7. Review). PKD2L1 is most similar to PKD2. The human gene was first identified by Wu et al. (Wu et al. (1998) "Identification of PKD2L, a Human PKD2-Related Gene: Tissue-specific Expression and Mapping to Chromosome 10q25" *Genomics* 54(3) 564-568), and the mouse ortholog was isolated in a search for new members of the PKD family (Basora et al. (2002) "Tissue and Cellular Localization of a Novel Polycystic Kidney Disease-Like Gene Product, Polycystin-L" *J. Am. Soc. Nephrol* 13:293-301). An alignment of sequences for human, rat, and mouse PKD2L1 is provided in FIG. 2A-2B. Included in the alignment in FIG. 2A is the match to a PCR fragment isolated from taste receptor cells (corresponding to exons 2-5), and used as the probe in the in situ studies shown in FIG. 1A. FIG. 2B shows an alignment of mouse to rat and human, along with percent identity calculations between mouse and rat (~86% identical) and mouse and human (~80% identical).

```
Mouse PKD2L1 fragment isolated from taste tissue
(exons 2-5) (SEQ ID NO:1): DNA
ACAGCCGAGAACAGGGAGCTTTATGTCAAGACCACCCTGAGGGAGCTTGT

GGTATACATAGTGTTCCTCGTGGACGTCTGTCTGTTGACCTACGGAATGA

CAAGTTCTAGTGCCTATTACTACACCAAAGTGATGTCTGAGTTGTTCCTA

CACACCCCATCCGACTCTGGAGTCTCCTTCCAGACCATCAGCAGCATGTC

AGACTTCTGGGATTTTGCTCAGGGCCCACTCCTGGACAGTTTGTACTGGA

CAAAGTGGTACAACAACCAGAGCCTGGGGCGTGGCTCCCACTCCTTCATC

TACTATGAGAACCTGCTCCTGGGAGCCCCAAGGTTGCGGCAGCTGCGCGT

GCGCAATGACTCCTGTGTGGTTCATGAAGACTTCCGGGAGGACATTTTGA

ACTGTTATGATGTGTACTCGCCGGACAAAGAAGATCAGCTCCCCTTTGGA

CCTCTGAACGGCACAGCGTGGACATACCATTCCCAGAATGAGCTGGGTGG

CTCCTCCCACTGGGGCAGGCTCACAAGCTACAGCGGGGGTGGCTACTACT

TGGATCTTCCAGGATCCCGACAAGCCAGTGCAGAGGCCCTCCAAGGACTC

CAGGAGGGACTG
```

Taste tissue may also express PKD2L1 splice variants and may be present in PKD2L1 cDNA libraries.

```
Predicted Amino Acid sequence
                        (SEQ ID NO:2)
TAENRELYVKTTLRELVVYIVFLVDVCLLTYGMTSSSAYYYTKVMSELFL

HTPSDSGVSFQTISSMSDFWDFAQGPLLDSLYWTKWYNNQSLGRGSHSFI

YYENLLLGAPRLRQLRVRNDSCVVHEDFREDILNCYDVYSPDKEDQLPFG
```

```
                        -continued
PLNGTAWTYHSQNELGGSSHWGRLTSYSGGGYYLDLPGSRQASAEALQGL

QEGL mouse PKD2L1 predicted mRNA (full-length,
SEQ ID NO:3)
ATGAAAGTATGGAAAGCCCCAAGAATCAGGAGCTACAAACCCTGGGGAAC

AGAGCCTGGGACAATCCTGCCTACAGCGACCCTCCTTCCCCGAACAGGAC

GCTGAGGATCTGCACTGTCTCCAGTGTGGCTCTCCCTGAGACTCAACCCA

AAAAGCCAGAAGTCAGATGCCAGGAGAAGACACAGAGAACCCTGGTGTCC

AGCTGCTGTCTCCATATCTGTCGGAGCATCAGAGGACTGTGGGGACAAC

GCTGACTGAGAACACAGCCGAGAACAGGGAGCTTTATGTCAAGACCACCC

TAAGGGAGCTTGTGGTATACATAGTGTTCCTCGTGGACGTCTGTCTGTTG

ACCTACGGAATGACAAGTTCTAGTGCCTATTACTACACCAAAGTGATGTC

TGAATTGTTTCTACACACCCCATCCGACTCTGGAGTCTCCTTCCAAACCA

TCAGCAGCATGTCAGACTTCTGGGATTTTGCTCAGGGCCCACTCCTGGAC

AGTTTGTACTGGACAAAGTGGTACAACAACCAGAGCCTGGGGCGTGGCTC

CCACTCCTTCATCTACTATGAGAACCTGCTCCTGGGAGCCCCAAGGTTGC

GGCACGTGCGCGTGCGCAATGACTCCTGTGTGGTTCATGAAGACTTCCGG

GAGGACATTTTGAACTGTTATGATGTGTACTCGCCGGACAAAGAAGATCA

GCTCCCCTTTGGACCTCAGAACGGCACAGCGTGGACATACCATTCCCAGA

ATGAGCTGGGTGGCTCCTCCCACTGGGGCAGGCTCACAAGCTACAGCGGG

GGTGGCTACTACTTGGATCTTCCAGGATCCCGACAAGCCAGTGCAGAGGC

CCTCCAAGGACTCCAGGAGGGACTGTGGCTGGACAGGGGCACTCGGGTGG

TCTTTATCGACTTCTCCGTCTACAATGCCAACATCAATCTTTTCTGTATT

CTGAGACTGGTGGTAGAGTTTCCAGCCACAGGAGGGACCATCCCATCCTG

GCAGATCCGCACAGTTAAGCTGATCCGCTATGTGAATAACTGGGACTTCT

TCATTGTGGGCTGTGAAGTTGTCTTCTGTGTCTTCATCTTCTATTATGTG

GTGGAGGAAATCCTGGAAATCCACCTGCATCGGCTTCGCTACCTCAGCAG

CGTCTGGAACATTCTGGACCTGGTGGTCATCTTGCTCTCCATCGTGGCTG

TGGGTTTCCACATATTCCGAACCCTGGAAGTGAACCGACTGATGGGAAAG

CTTCTGCAACAGCCAGACACGTATGCAGACTTTGAGTTCCTGGCCTTCTG

GCAGACTCAGGACAATAACATGAACGCGGTCAACCTTTTCTTTGCTTGGA

TCAAGATATTCAAGTATATCAGCTTCAACAAGACCATGACACAGCTCTCC

TCCACCCTGGCTCGATGTGCCAAGGACATCCTGGGCTTCGCAGTCATGTT

CTTCATTGTCTTCTTCGCTTACGCCCAGCTTGGTTACCTGCTTTTTGGGA

CCCAAGTGGAAAACTTTAGCACTTTCGTCAAGTGCATTTTCACTCAGTTC

CGGATAATCCTTGGGGATTTTGACTACAATGCCATCGACAATGCCAACAG

AATCCTGGGCCCTGTGTACTTTGTCACCTATGTCTTCTTCGTCTTCTTCG

TGCTCCTGAACATGTTCCTGGCCATCATCAACGACACATACTCCGAGGTC

AAGGAGGAGCTGGCTGGCCAGAAGGATCAGTTGCAGCTTTCTGACTTCCT

GAAACAGAGCTACAACAAGACCCTACTAAGGCTGCGCCTGAGGAAAGAGC
```

-continued
GGGTTTCTGATGTGCAGAAGGTCCTGAAGGGTGGGGAACCAGAGATCCAG

TTTGAAGATTTCACCAGCACCTTGAGGGAACTGGGGCACGAGGAGCACGA

GATCACCGCTGCCTTCACCAGGTTTGATCAGGATGGGGACCACATACTGG

ATGAGGAGGAGCAGGAACAGATGCGGCAGGGACTGGAAGAGGAGAGGGTG

ACCCTCAATGCTGAGATTGAGAACCTAGGCCGGTCTGTTGGACACAGCCC

CCCAGGCGAATTGGGCGCGGAGGCTGCCAGAGGACAAAGCTGGGTTTCTG

GAGAAGAATTCGACATGCTCACAAGGAGAGTTCTGCAGCTGCAGTGTGTT

CTGGAAGGAGTTGTGTCCCAGATTGATGCTGTAGGCTCAAAGCTGAAGAT

GCTGGAGAGGAAAGGGGAGCTGGCTCCCTCCCCAGGAATGGGGGAACCAG

CTGTTTGGGAGAACCTGTATAATCCGTCCTAGT human PKD2L1 taste predicted mRNA sequence
(full-length, SEQ ID NO:4):
ATGAATGCTGTGGGAAGTCCTGAGGGGCAGGAGCTGCAAAAGCTGGGGAG

TGGAGCCTGGGACAACCCCGCCTACAGTGGTCCCCCTTCCCCACACGGGA

CGCTGAGAGTCTGCACCATCTCCAGCACGGGGCCTCTCCAGCCCCAACCC

AAGAAGCCTGAAGATGAACCCCAGGAGACGGCATACAGGACCCAGGTGTC

CAGCTGCTGCCTCCATATCTGTCAAGGCATCAGAGGACTTTGGGGAACAA

CCCTGACTGAGAACACAGCTGAGAACCGGGAACTTTATATCAAGACCACC

CTGAGGGAGCTGTTGGTATATATTGTGTTCCTGGTGGACATCTGTCTACT

GACCTATGGAATGACAAGCTCCAGTGCTTATTACTACACCAAAGTGATGT

CTGAGCTCTTCTTACATACTCCATCAGACACTGGAGTCTCCTTTCAGGCC

ATCAGCAGCATGGCGGACTTCTGGGATTTTGCCCAGGGCCCACTACTGGA

CAGTTTGTATTGGACCAAATGGTACAACAACCAGAGCCTGGGCCATGGCT

CCCACTCCTTCATCTACTATGAGAACATGCTGCTGGGGGTTCCGAGGCTG

CGGCAGCTAAAGGTCCGCAATGACTCCTGTGTGGTGCATGAAGACTTCCG

GGAGGACATTCTGAGCTGCTATGATGTCTACTCTCCAGACAAAGAAGAAC

AACTCCCCTTTGGGCCCTTCAATGGCACAGCGTGGACATACCACTCGCAG

GATGAGTTGGGGGGCTTCTCCCACTGGGGCAGGCTCACAAGCTACAGCGG

AGGTGGCTACTACCTGGACCTTCCAGGATCCCGACAGGGTAGTGCAGAGG

CTCTCCGGGCCCTTCAGGAGGGGCTGTGGCTGGACAGGGGCACTCGAGTG

GTGTTCATCGACTTCTCAGTCTACAATGCCAATATCAATCTTTTCTGTGT

CCTGAGGCTGGTGGTGGAGTTTCCAGCTACAGGAGGTGCCATCCCATCCT

GGCAAATCCGCACAGTCAAGCTGATCCGCTATGTCAGCAACTGGGACTTC

TTTATCGTTGGCTGTGAGGTCATCTTCTGCGTCTTCATCTTCTACTATGT

GGTGGAAGAGATCCTGGAGCTCCACATTCACCGGCTTCGCTACCTCAGCA

GCATCTGGAACATACTGGACCTGGTGGTCATCTTGCTCTCCATTGTGGCT

GTGGGCTTCCACATATTCCGAACCCTCGAGGTGAATCGGCTCATGGGGAA

GCTCCTGCAGCAGCCAAACACGTATGCAGACTTTGAGTTCCTCGCCTTCT

GGCAGACACAGTACAACAACATGAATGCTGTCAACCTCTTCTTCGCCTGG

-continued
ATCAAGATATTCAAGTACATCAGCTTCAACAAAACCATGACCCAGCTCTC

CTCCACGCTGGCCCGCTGTGCCAAGGACATCCTGGGCTTCGCCGTCATGT

TCTTCATTGTTTTCTTCGCCTATGCCCAACTCGGCTACCTGCTTTTCGGG

ACCCAAGTGGAAAACTTTAGCACTTTCATCAAGTGCATTTTCACTCAGTT

CCGGATAATCCTCGGGGACTTTGACTACAATGCTATCGACAATGCCAACC

GCATCCTGGGCCCTGCCTACTTTGTCACCTATGTCTTCTTCGTCTTCTTC

GTGCTCCTGAACATGTTCCTGGCCATCATCAATGACACATATTCAGAGGT

CAAGGAGGAGCTGGCTGGACAGAAGGATGAGCTGCAACTTTCTGACCTCC

TGAAACAGGGCTACAACAAGACCCTACTAAGACTGCGTCTGAGGAAGGAG

AGGGTTCGGATGTGCAGAAGGTCCTGCAGGGTGGGGAGCAGGAGATCCA

GTTTGAGGATTTCACCAACACCTTAAGGGAACTGGGACACGCAGAGCATG

AAATCACTGAGCTCACGGCCACCTTCACCAAGTTTGACAGAGATGGGAAT

CGTATTCTGGATGAGAAGGAACAGGAAAAAATGCGACAGGACCTGGAGGA

AGAGAGGGTGGCCCTCAACACTGAGATTGAGAAACTAGGCCGATCTATTG

TGAGCAGCCCACAAGGCAAATCGGGTCCAGAGGCTGCCAGAGCAGGAGGC

TGGGTTTCAGGAGAAGAATTCTACATGCTCACAAGGAGAGTTCTGCAGCT

GGAGACTGTCCTGGAAGGAGTAGTGTCCCAGATTGATGCTGTAGGCTCAA

AGCTGAAAATGCTGGAGAGGAAGGGGTGGCTGGCTCCCTCCCCAGGCGTG

AAGGAACAAGCTATTTGGAAGCACCCGCAGCCAGCCCCAGCTGTGACCCC

AGACCCCTGGGAGTCCAGGGTGGGCAGGAGAGTGAGGTTCCCTATAAAA

GAGAAGAGGAAGCCTTAGAGGAGAGGAGACTCTCCCGTGGTGAGATTCCA

ACGTTGCAGAGGAGTTAA

Ensembl predicts an ortholog in the Dog genome:
geneID<ENSCAFG00000009644> (SEQ ID NO:5)
MNAVESPEGQELQKMGSGAWDNPAYSGPPSPRGTLKICTISSAMPPQPQI

QKPEDGPQEKAYRTLVSSCCFQICRGIRGLWGTTLTENTAENRELYVKTT

LRELLVYIVFLVDICLLTYGMTSSSAYYYTKVMSELFLHTPSDTGVSFQA

ISSMADFWDFAQGPLLDSLYWTKWYNNQSLGHGSHSFIYYENLLLGVPRL

RQLRVRNDSCVVHEDFREDILSCYDVYSPDKEEQLPFGPLNGTAWTYHSQ

DELGGSSHWGRLTSYSGGGYYLDLPGSRQASAEALQDLQEGLWLDRGTRV

VFIDFSVYNANINLFCVLRLVVEFPATGGAIPSWQIRTVKLIRYVSNWDF

FIIGCEIIFCIFIVYYMVEEILELHIHRLHYLSSIWNILDLVVIMLSIVA

VGFHIFRTLEVNRLMGKLLQQPNMYADFEFLAFWQTQYNNMNAVNLFFAW

IKIFKYISFNKTMTQLSSTLARCAKDILGFAVMFFIVFFAYAQLGYLLFG

TQVENFSTFIKCIFTQFRIILGDFDYNAIDNANRILGPAYFVTYVFFVFF

VLLNMFLAIINDTYSEVKEELAGQKDELQLSDLLKQGYNKTLLRLRLRKE

RVSDVQKVLQGGEQEIQFEDFTNTLRELGHAEHEITELTAAFTRFDQDGN

HILDKKEQEQMQQDLEEKRVVLNAEIENLGQSIVSSSPGESGPEATRADG

WVSGEEFYTLTRRVLQLETVLEGVMSQVDAVGSKLEMLERKEQLASSPGM

GDQGIWEHLQPTSPVTPDPWGVQGGQESEFPGGREGEALEEMRLS

Additional References

Liu et al. (2002) "Modulation of the human polycystin-L channel by voltage and divalent cations" *FEBS Letters* 525 (1-3) 71-76; Keller et al. (1994) "Kidney and Retinal Defects (Krd), a Transgene-Induced Mutation with a Deletion of Mouse Chromosome 19 That Includes the Pax2 Locus" *Genomics* 23: 309-320; Gilbertson, T. (1993) The physiology of vertebrate taste reception 3, 532-539; Kinnamon and Margolskee (1996), *Curr. Opin. Neurobiol.* 4:506-513; Adler et al. (2000) "A novel family of mammalian taste receptors" *Cell* 100:693-702; Chandrashekar et al. (2000) "T2Rs function as bitter taste receptors" *Cell* 100:703-711.

Example 2

A Novel Gene Preferentially Expressed in Mammalian Taste Receptor Cells (PKD1L3)

To discover novel receptors, ion channels and other membrane signaling molecules involved in signal transduction in taste receptor cells, we developed a novel bioinformatics/molecular screening strategy. Our approach relied on two empirical assumptions: First, receptors and ion channels are transmembrane proteins. Second, sensory receptors in the visual, olfactory, touch and taste systems are often selectively expressed in restricted numbers of tissues. Therefore, we searched the mouse genome for transmembrane proteins, and then screened for those with restricted expression. Chosen molecules were subjected to experimental validation by PCR amplification reactions using taste tissue and in situ hybridization studies against mouse tongues.

Overview

Using a Hidden Markov Model (TMHMM 2.0) and f_TM-HMM (UCSD Supercomputing Center, Bourne lab), we screened the entire Ensembl mouse genome database for genes encoding putative transmembrane domains. In order to determine the tissue distribution for the chosen candidate genes, we used mouse Expression Sequence Tag (EST) databases (www.ncbi.nlm.nih.gov/BLAST) to identify gene transcripts (i.e., cDNAs) expressed in 3 tissues/organs or less. PCR amplification primers were then prepared against selected cDNAs and RT-PCR reactions using mRNA from taste and non-taste tissues were carried out. Candidates preferentially expressed in taste receptor cells were used for RNA in situ hybridization against various taste papillae. Full-length clones were then isolated from cDNA libraries prepared from taste tissue and testis (testis usually express most sensory-specific genes). This strategy led to the isolation of a PKD2-L1 (PKD2-like 1), a member of the Polycystic Kidney Disease (PKD) family of proteins selectively expressed in taste tissue (See, Example 1).

Members of the PKD family of genes belong to one of two independent subgroups: PKD1s and PKD2s. Since PKD2s are often found in association with PKD1s (generally as heteromeric receptors/channels), we searched for PKD1-related family members in taste tissue. Using RT-PCR and RNA in situ hybridizations against taste papillae, we isolated and identified PKD1-L3 as a novel PKD selectively expressed in subsets of taste receptor cells.

Bioinformatics Screen:

Using homology and literature searches we screened the mouse and human genome databases for members of the PKD1 family of proteins. We then performed RT-PCR reactions with primers specifically targeting predicted exon regions for PKD1, PKD1-L1 (Yuasa et al., 2002), PKD1-L2 (L1 et al., 2003), and PKD1-L3 (L1 et al., 2003) using mRNA from taste tissue. Two sets of primers specific for PKD1-L3 produced correct PCR products in taste tissue but not in control non-taste epithelia.

RT-PCRs

Peeled, hand-dissected circumvallate and foliate taste papillae from ~20 mice were collected for each mRNA extraction (total of ~120 mice were used). Tissue was stored in RNAlater (Qiagen), and mRNA was extracted using Micro-FastTrack 2.0 mRNA extraction kit (Invitrogen). cDNA was synthesized using SuperScript II first-strand cDNA synthesis kit (Invitrogen) using oligo(dT) as primers. cDNA synthesis and progress was monitored by using T1R3 (Nelson et al., 2001) and GAPDH as controls.

RT-PCR experiments were performed using a minimum of two independent RT preparations, each containing a mix of circumvallate and folliate mRNA (taste mRNA).

Figure 3:
FIG. 3 is photograph showing results demonstrating that PKD1L3 selectively labels taste receptor cells.

RNA in Situ Hybridization:

Candidates shown to be selectively enriched in taste tissue by RT-PCR were cloned into plasmid vectors and used to generate specific probes for RNA in situ hybridizations experiments (see methods section in Hoon et al., 1999 for details on in situ preparations). Male and female mouse tongues containing different taste papillae were used in all in situ studies. FIG. 3 demonstrates that PKD1-L3 (probes ID "ex28-32" and "ex25" derived from exons 28-32 and exon 25, respectively) selectively labels taste receptor cells. Note the expression in subsets of taste cells, but not in surrounding non-taste tissue. FIG. 4 shows an alignment of mouse, rat, and human PKD1-L3 protein sequences, including computer-predicted exons.

REFERENCES

Hoon M A, Adler E, Lindemeier J, Battey J F, Ryba N J, Zuker C S (1999). Putative mammalian taste receptors: a class of taste-specific GPCRs with distinct topographic selectivity. Cell 96, 541-51

Nelson, G., Hoon, M A., Chandrashekar, J., Zhang, Y., Ryba, N J., and Zuker, C S. (2001). Mammalian sweet taste receptors. Cell. 2001 Aug. 10; 106(3): 381-90.

Lin, S Y, and Corey, D P. (2005). TRP channels in mechanosensation. Curr Opin Neurobiol. 2005 May 25 (Epub ahead of print)

Nomura, H., Turco, A E., Pei, Y., Kalaydjieva, L., Schiavello, T., Weremowicz, S., Ji, W., Morton, C., Meisler, M., Reeders, S T., and Zhou, J. (1998) Identification of PKDL, a novel polycystic kidney disease 2-like gene whose murine homologue is deleted in mice with kidney and retinal defects. J. Biol. Chem. 273 (1998), pp. 25967-25973.

Wu, G., Hayashi, T., Park, J H., Dixit, M., Reynolds, D M., Li, L., Maeda, Y., Cai, Y., Coca-Prados, M., and Somlo, S. (1998) Identification of PKD2L, a Human PKD2-Related Gene: Tissue-specific Expression and Mapping to Chromosome 10q25. Genomics. vol54(3) Dec. 15 1998 pg. 564-568.

Liu, Y., L1, Q., Tan, M., Zhang, Y Y., Karpinski, E., Zhou, J., and Chen, X Z. (2002). Modulation of the human polycystin-L channel by voltage and divalent cations. FEBS Letters Vol 525, Issues 1-3, Aug. 14, 2002, pages 71-76.

Basora, N., Nomura, H., Berger, UV., Stayner, C., Guo L., Shen, X., and Zhou, J. (2002) Tissue and Cellular Localization of a Novel Polycystic Kidney Disease-Like Gene Product, Polycystin-L. J. Am. Soc. Nephrol 13:293-301, 2002.

Li A, Tian X, Sung S W, and Somlo S. (2003) Identification of two novel polycystic kidney disease -1-like genes in human and mouse genomes. Genomics. 2003 June; 81(6): 596-608. Erratum in: Genomics. 2003 October; 82(4): 498-500.

Yuasa T, Venugopal B, Weremowicz S, Morton C C, Guo L, and Zhou J. (2002) The sequence, expression, and chromosomal localization of anovel polycystic kidney disease 1-like gene, PKD1L1, in human. Genomics. 2002 March; 79(3): 376-86.

Mouse PKD1-L3 gene fragments isolated from taste tissue cdna:

PKD1L3 Exon25 (SEQ ID NO: 6):
TCCACAAGCAAATGAAGTCGCCTCCCCAACATCAGGAGGACAGAGAGAAC
TATGGGGCTGGCTGGGTCCCCCCTGACACAAACATCACAAAAGTAGACAG
TATTTGGCATTATCAGAATCAGGAGTCGCTGGGAGGCTATCCCATCCAAG
GGGAGCTAGCCACTTACTCAGGAGGAGGCTATGTTGTGAGGCTTGGAAGA
AACCACAGGGCG PKD1-L3 Exons 28-32 (SEQ ID NO:7):
GGAAAAGGAACCTCCTGGACACAAGCATCGTCCTCATTAGCTTCAGCATC
CTGGGCCTCAGCATGCAGAGCCTCTCTCTACTTCACAAAAAGATGCAGCA
GTACCACTGTGACCGGGACAGGTTCATCAGTTTCTACGAGGCACTGAGAG
TGAACTCTGCAGTCACCCACCTCAGGGGCTTCCTGCTTCTCTTCGCAACT
GTGCGGGTCTGGGACCTACTGCGACATCATGCCCAGTTACAGGTCATCAA
CAAGACACTGTCCAAAGCCTGGGACGAGGTGCTGGGCTTTATACTGATCA
TCGTGGTCCTGTTAAGCAGCTATGCCATGACTTTCAACCTGCTGTTTGGA
TGGAGCATCTCTGACTACCAGAGCTTCTTCAGATCTATAGTGACTGTTGT
TGGCCTCTTGATGGGAACTTCAAAGCACAAGGAGGTTATTGCTCTATACC
CAATCCTGGGCTCCCTTTTGGTTCTCAGTAGCATCATCTTGATGGGACTT
GTGATCATTAATCTTTTTGTTTCTGCCATTCTCATTGCCTTTGGGAAAGA
AAGGAAGGCCTGTGAGAAAGAAGCTACACTGACAGATATGTTACTACAAA
AGCTCTCAAGTCTGTTAGGAATCCGCCTGCACCAGAATCCATCTGAGGAA
CACGC Predicted Amino Acid sequences:

PKD1L3 Exon25 (SEQ ID NO:8)
HKQMKSPPQHQEDRENYGAGWVPPDTNITKVDSIWHYQNQESLGGYPIQG
ELATYSGGGYVVRLGRNHRA PKD1L3 Exons 28-32 (SEQ ID NO:9)
KRNLLDTSIVLISFSILGLSMQSLSLLHKKMQQYHCDRDRFISFYEALRV
NSAVTHLRGFLLLFATVRVWDLLRHHAQLQVINKTLSKAWDEVLGFILII
VVLLSSYAMTFNLLFGWSISDYQSFFRSIVTVVGLLMGTSKHKEVIALYP
ILGSLLVLSSIILMGLVIINLFVSAILIAFGKERKACEKEATLTDMLLQK
LSSLLGIRLHQNPSEEH mouse PKD1L3 predicted mRNA (full-length)
(SEQ ID NO:10)
ATGCTCTTGCAGAGGCGGTCCTGGCTCTGGCTGTACATTAGAATCGGTGT
CATTCTGGGTGATATTTTGGGACGTAAACCAAGCATCCGGGAGCAACATG
GGGGAAACAGCTGCTATCAGCTTAACAGACTTTTCTGTGACTTCCAGGAA
GCAGATAACTACTGCCACGCCCAGAGAGGACGCCTAGCCCACACGTGGAA
CCCCAAGCTTCGGGGTTTCCTAAAAAGCTTCCTGAATGAAGAAACAGTGT
GGTGGGTCAGGGGAAACCTGACGCTGCCCGGATCGCATCCAGGGATAAAT
CAGACAGGAGGTGATGACGTCTTAAGGAACCAAAAGCCTGGCGAGTGCCC
TTCCGTGGTCACACACTCTAATGCTGTCTTCTCAAGATGGAACCTGTGCA
TAGAGAAGCATCATTTCATTTGCCAGGCTGCCGCCTTTCCCCCTCAAGGT
GCAAGCATTTGGAGAAATGAGTTTGGTCCTGGTCCTCTGTTACCCATGAA
AAGAAGAGGAGCTGAGACAGAGAGACATATGATCCCAGGAAATGGCCCCC
CGTTAGCCATGTGTCACCAACCCGCTCCTCCTGAGCTTTTTGAGACATTG
TGCTTTCCCATTGACCCAGCTTCTTCAGCACCTCCAAAAGCCACACACAG
GATGACAATCACATCCCTAACTGGAAGGCCACAGGTGACATCAGACACAC
TTGCATCCAGCAGCCCACCACAGGGGACATCAGACACACCTGCATCCAGC
AGCCCACCACAGGTGACATCAGCCACATCTGCATCTAGCAGCCCACCACA
GGGGACATCAGACACACCTGCATCCAGCAGCCCACCACAGGTGACATCAG
CCACATCTGCATCTAGCAGCCCACCACAGGGGACATCAGACACACCTGCA
TCCAGCAGCCCACCACAGGTGACATCAGCCACATCTGCATCTAGCAGCCC
ACCACAGGGGACATCAGACACACCTGCATCCAGCAGCCCACCACAGGTGA
CATCAGCCACATCTGCATCTAGCAGCCCACCACAGGGGACATCAGACACA
CCTGCATCCAGCAGCCCACCACAGGGGACATTAGACACACCTTCATCTAG
CAGCCCACCACAGGGGACATCAGACACACCTGCATCCAGCAGCCCACCAC
AGGGGACATCAGACACCTGCATCCAACAGCCCACCACAGGGGACATCA
GAGACACCTGGATTCAGCAGCCCACCACAGGTGACAACAGCCACACTTGT
ATCCAGCAGCCCACCACAGGTGACATCAGAGACACCTGCATCCAGCAGCC
CAACACAGGTGACATCAGAGACACCTGCATCCAGCAGCCCAACACAGGTG
ACATCAGACACACCTGCATCCAATAGCCCACCACAGGGGACATCAGACAC
ACCTGGATTCAGCAGCCCAACACAGGTGACAACAGCCACACTTGTATCCA
GCAGCCCACCACAGGTGACATCAGACACACCTGCATCCAGCAGCCCACCA
CAGGTGACATCAGACACACCTGCATCCAGCAGCCCACCACAGGTGACATC
AGAGACACCTGCATCCAGCAGCCCACCACAGGTGACATCAGACACATCTG
CATCCATCAGCCCACCACAGGTAATATCAGACACACCTGCATCCAGCAGC
CCACCACAGGTGACATCAGAGACACCTGCATCCAGCAGCCCAACAAACAT
GACATCAGACACACCTGCATCCAGCAGCCCAACAAACATGACATCAGACA
CACCTGCATCCAGCAGCCCAACAAACATGACATCAGACACACCTGCATCC
AGCAGCCCACCATGGCCTGTTATAACAGAGGTCACCAGGCCTGAATCCAC
AATACCTGCTGGAAGATCTTTGGCAAACATCACTTCAAAGGCACAGGAAG
ACTCTCCCCTGGGAGTCATCTCTACCCATCCACAGATGTCATTTCAGAGT
TCAACCAGTCAGGCCTTGGATGAGACAGCAGGGGAACGGGTCCCAACAAT
TCCTGATTTCCAAGCCCACAGTGAATTCCAGAAAGCTTGTGCCATCCTCC

```
AGAGACTGAGAGACTTCCTGCCGACTTCTCCCACATCAGCTCAGGTCAGT
GTGGCCAATTTACTCATTGACCTGAGTGAGCAGTTGCTGGTGCTCCCGTT
TCAGAAGAACAACAGTTGGAGCTCTCAAACTCCAGCAGTCAGCTGCCCCT
TCCAGCCTCTTGGACGTCTAACAACAACGGAAAAAAGCAGTCATCAGATG
GCTCAGCAAGACATGGAACAGGTTGAAGACATGCTGGAGACATCCCTGAT
GGCCCTGGGGGAGATCCACAGAGCATTTTGCCAGCAGAGTCTGTGCCCTC
AGTCAGCAGTGACCCTGGCCTCTCCCTCTGCTACTCTGATGTTGAGCAGC
CAAAATGTGTCAACGTTGCCCCTGAGCACCTACACTTTGGGTGAGCCTGC
ACCCTTGACTTTGGGCTTCCCGTCAGCAGAAGCTCTGAAGGAGCTCTTGA
ACAAACACCCAGGCGTGAACCTTCAAGTGACAGGTCTGGCTTTCAACCCT
TTTAAGACTTTGGATGACAAGAACATTGTTGGAAGCATTGGAAATGTGCA
GCTGAGCTCTGCTTATCAGTCGATCAGAGTCCACGACTTAATAGAAGATA
TTGAGATCATGCTCTGGAGAAATGCCAGCATGGAGACCCAGCCCACCAGC
CTCAACACAAGTACAGACCATTTCACAATCTCTGTGAACATCACTTCCTT
GGAGAAGACCCTCATTGTGACCATCGAGCCTGAAAGTCCCCTCCTAATGA
CGCTCCACTTGGGCTTCCAGGACCAGCTGGCCCACACTCACTTCTATCTC
AACATCAGCCTGCCAAGGGACCAAGTGTGGCAGAAAGATGAGGAGTACAC
GTGGGTGCTGACACCAGAGAACCTGTGGTACGGGACTGGCACCTACTACA
TAATGGCTGTGGAGAATAAAAGTACAGAGGCGGCACAGCACACACCCGTC
CTGGTCTCAGTGGTCACAGCTGTCACCCAGTGCTATTTCTGGGACCGATA
CAATAGGACATGGAAGAGCGATGGATGCCAAGTGGGGCCGAAGAGCACCA
TTTTAAAGACACAGTGTCTCTGTGACCACCTGACCTTCTTCAGCAGCGAC
TTCTTCATCGTGCCGAGGACGGTGGATGTAGAAAACACCATCAAACTGCT
TCTTCATGTGACCAACAACCCTGTCGGGGTGTCATTGCTGTCCAGCCTCC
TAGGATTCTATATCCTCTTAGCCATGTGGGCTTCCAGAAAGGATCGAGAA
GATATGCAGAAGGTGAAGGTAACAGTCCTGGCTGACAATGACCCCAGCTC
TGCATCCCACTACCTTATCCAGGTCTACACTGGCTATCGGAGGAGGGCTG
CTACCACCGCCAAGGTCGTTATCACTCTCTATGGCTCAGAGGGGCACAGT
GAGCCCCACCACCTTTGTGACCCTGAGAAGACAGTTTTTGAGCGTGGAGC
ACTGGATGTTTTCCTTCTTTCCACCGGATCCTGGCTGGGGACCTGCATG
GCCTTCGGCTGTGGCATGACAATTCTGGCGACAGCCCTTCTTGGTATGTA
AGCCAGGTGATCGTCAGTGACATGACCACGAGGAAGAAATGGCATTTCCA
GTGCAATTGTTGGCTGGCCGTGGACTTGGGCAACTGTGAGCGTGACAGGG
TGTTCACACCAGCCTCCAGAAGCGAGCTCTCTTCCTTCAGACACCTGTTC
TCCTCCACAATCGTAGAAAAGTTCACCCAGGATTATCTGTGGCTCTCAGT
TGCAACTCGACATCCCTGGAACCAGTTTACACGAGTCCAGAGGCTCTCCT
GCTGCATGGCACTACTGCTCTGTGACATGGTCATCAATATTATGTTCTGG
AAGATGGGTGGCACCACTGCCAAGAGGGGCACCGAACAACTAGGTCCACT
TGCTGTGACCTTGTCGGAGCTGCTCGTCAGCATCCAGACCTCCATCATCC
TCTTCCCCATCCACCTCATCTTTGGGCGGCTCTTCCAGTTGATTCACCCA
CCAGAAGCTCTGCCCCAGCTTCCTTTCATCCAGGCTGCCTGGCCCCCTGC
TCTTGTTTGTGAGTCCCCCTCTCTTACACAGGTGGTCAAGGAATTAAAGG
AAACTGTGGGATTCCTGCTCAGGAGAAATACACAGCTGCTCTCGGAGTGT
GAGCCGTCTTCGTGCAGTTCTTGTGACATTAACAAGCTGGCGAAGCTTTT
ATCCGGCCTCATTTACTGTCACTTAGAAGACGAAGGCTGTCACCAGCAGA
CAGAATCCCACTGGGAAGACGCAGTGTCTGAAAACCATTACCATTTCTGC
CGCTACCTTCTCCAACTTCTGCGGAGACTGAAAGCGCATTTAGAGGCTCT
TGGTGCTACCCAGGATCACCAGTCTTGTGATTTCTCAGAAGCAGTCAGCC
AACTTCAAAACCTCCAGGAACTCCTGGAGACACAGACTCTCCGCAGAGGG
CCAGGGCCATGCAGGCATTCCACCAGTTTCCCCATCCTCAGCCCAGGAGA
AGGGAAGAAGCCCATGTCATTTTGCCTGTTCAGATGGTTGAAGTGCAGCT
GCTGGCTCCTTCTTGGTGTCATCAGCCTGGCCTCGGCCTTTTTTATAACG
CTCTATAGCTTGGAGTTGGACAAAGACCAAGCCACCAGCTGGGTTATTTC
AATGATGCTGTCGGTACTACAAGACATCTTTATCAGCCAGCCGATAAAGG
TCATCTTCCTGACATTGTTGTTCTCCCTGATGGCAAACCACATGCCGTGG
CTTAACAAAGACAAGGAACAACACGCCCGGAGAATCGTAGCACTTTGGGC
AAAGTGTCCTTGGTCGGCACCTGGCTTGAGAGACAAGAACAATCCCATCT
ACACTGCCCCAGCAATGAACAACCTAGCCAAGCCTACAAGGAAGGCCTGG
AAGAAGCAGCTCTCCAAGCTGACGGGTGGTACTCTGGTGCAAATCCTCTT
CCTGACCCTGCTGATGACTACCGTCTATTCTGCAAAGGACTCTAGTCGAT
TTTTCCTCCATCGAGCTATCTGGAAGAGGTTTTCTCACCGTTTCTCAGAA
ATCAAAACTGTAGAGGATTTCTACCCCTGGGCCAACGGCACCCTCCTTCC
TAACCTATATGGGGATTACAGAGGATTTATTACTGACGGGAACTCCTTTC
TTCTGGGCAATGTTTTGATCCGCCAGACTCGCATTCCTAATGACATATTC
TTCCCAGGATCTCTCCACAAGCAAATGAAGTCGCCTCCCCAACATCAGGA
GGACAGAGAGAACTATGGGGCTGGCTGGGTCCCCCCTGACACAAACATCA
CAAAAGTAGACAGTATTTGGCATTATCAGAATCAGGAGTCGCTGGGAGGC
TATCCCATCCAAGGGGAGCTAGCCACTTACTCAGGAGGAGGCTATGTTGT
GAGGCTTGGAAGAAACCACAGTGCGGCAACCAGGGTTCTGCAGCATCTGG
AACAGAGGCGCTGGCTGGACCACTGCACAAAAGCCCTCTTTGTAGAATTC
ACGGTCTTCAATGCTAATGTGAATCTGCTCTGTGCGGTGACCCTCATCTT
GGAATCCAGTGGTGTGGGACTTTCCTCACCTCCCTGCAACTGGACAGTT
TAACTTCCCTTCAGTCATCAGAGAGGGGCTTCGCCTGGATCGTCTCACAG
GTCGTCTACTACCTTCTCGTCTGTTACTATGCCTTCATCCAGGGCTGTCG
GCTGAAGCGGCAGAGGCTGGCGTTCTTCACTAGGAAAGGAACCTCCTGG
ACACAAGCATCGTCCTCATTAGCTTCAGCATCCTGGGCCTCAGCATGCAG
AGCCTCTCTCTACTTCACAAAAAGATGCAGCAGTACCACTGTGACCGGGA
CAGGTTCATCAGTTTCTACGAGGCACTGAGAGTGAACTCTGCAGTCACCC
ACCTCAGGGGCTTCCTGCTTCTCTTCGCAACTGTGCGGGTCTGGGACCTA
CTGCGACATCATGCCCAGTTACAGGTCATCAACAAGACACTGTCCAAAGC
```

-continued
CTGGGACGAGGTGCTGGGCTTTATACTGATCATCGTGGTCCTGTTAAGCA

GCTATGCCATGACTTTCAACCTGCTGTTTGGATGGAGCATCTCTGACTAC

CAGAGCTTCTTCAGATCTATAGTGACTGTTGTTGGCCTCTTGATGGGAAC

TTCAAAGCACAAGGAGGTTATTGCTCTATACCCAATCCTGGGCTCCCTTT

TGGTTCTCAGTAGCATCATCTTGATGGGACTTGTGATCATTAATCTTTTT

GTTTCTGCCATTCTCATTGCCTTTGGGAAAGAAAGGAAGGCCTGTGAGAA

AGAAGCTACACTGACAGATATGTTACTACAAAAGCTCTCAAGTCTGTTAG

GAATCCGCCTGCACCAGAATCCATCTGAGGAACACGCTGACAACACTGGG

TATTGA human PKD1L3 predicted mRNA sequence (full-length)
(SEQ ID NO: 11):
ATGTTCTTCAAAGGAGGAAGCTGGCTTTGGTTATACATCAGAACAAGTAT

TATTCTAGGAAGTGAGCTAAACAGCCCAGCACCACATGGGCAAAATAATT

GTTACCAGCTTAACAGATTTCAATGCAGCTTTGAGGAAGCACAGCATTAC

TGTCATGTGCAGAGAGGATTCCTAGCTCATATTTGGAACAAGGAAGTTCA

AGATCTCATCCGGGACTATCTGGAAGAAGGAAAGAAGTGGTGGATTGGGC

AAAATGTAATGCCATTGAAAAAGCATCAAGACAACAAATACCCAGCAGAC

GTTGCAGCCAACGGGCCCCAAAGCCCCTCAGCTGCACCTACCTGTCCAG

AAACTTCATTCGGATCTCATCCAAAGGGGACAAGTGCTTACTGAAATACT

ATTTCATTTGCCAGACTGGTGACTTTTTGGACGGAGATGCCCATTATGAA

AGAAATGGAAATAATTCCCATTTGTACCAGAGACACAAGAAGACAAAAAG

AGGAGTTGCAATAGCAAGAGACAAAATGCCCCCAGGACCTGGTCATCTTC

CAACCACATGTCACTATCCTCTTCCTGCTCATCTTTCCAAGACCCTGTGT

CATCCCATCAGCCAGTTTCCTTCAGTACTATCAAGTATCACATCACAGGT

AACATCAGCCGCATCTGAACCCAGCAGCCAGCCTCTCCCTGTGATAACAC

AGCTCACCATGCCCGTGTCTGTCACGCATGCTGGGCAATGTCTGGGAGAA

ACAACTTCAAGGCCAAAGGAAGAAGGTCATCCGAATACCTTCACCTCTTA

TCTACAAGTGTCATTGCAGAAGGCATCTGGTCAGGTCATAGATGAGATAG

CAGGGAACTTCAGCAGAGCAGTTCATGGTTTGCAAGCTCTTAACAAACTA

CAGGAAGCTTGTGAGTTCCTCAGAAACTAACAGCCTTAACCCCAAGATT

TTCTAAGCCAGCTCAGGTTAATCTCATCAATTCCCTTATTTTACCTGAGT

GAGGAGTACTCAGGATCCCATTTCAGAACAACAACAGTCGGGCTTCAAAG

TTTCCTCCAACTGTCTGCCCCTTTCATTCCCTCAACAATGTCACCAAAGC

TGGAGAAGGAAGTTGGCTGGAATCCAAGCGTCATACTGAGCCGGTAGAAG

ACATCCTGGAAATGTCCTTGGTGGAGTTTGGGAATATCGGGGAAGCATTT

CTAGAGCAGAACCAGTCTCCCGAGTCTTCAGTGACTTTGACCTCTGCCAA

TGCTACTCTGCTGCTGAGCAGACAAAACATATCAACTTTACCGCTGAGCT

CTTACACTCTGGGTCACCCAGCCCCTGTGAGGCTAGGCTTTCCGTCGGCT

TTAGCTTTGAAGGAGCTCTTGAATAAACATCCAGGAGTTAATGTCCAAAT

AACAGGACTAGCTTTCAATCCCTTCAAGGATTTGGACAACAGAAACATTG

-continued
TTGGAAGCATTGGAAGTGTGTTACTAAGCGCTAATCGTAAATTGCTCCAA

GTCCATGATTTAATGGAGGACATTGAGATCATGCTCTGGAGAAATGTTAG

CTTGGAAACGCATCCCACCAGCCTCAACATGAGCACACATCAGCTTACAA

TCACAGTGAACGTCACTTCCTTTGGAGAAATCCTTGATAGTGAGCATAGA

TCCTGACAGTCCCCTTTAATGACACTCTACCTGGGGTTCCAGTATCAGCC

TAACTGCACTCACTTCCACCTGAACATCACCCTTCCAAAGGATAAGGTGT

GGCAAAAAGATGAGGAGTACACGTGGGTGCTGAATCCAGAGCATCTGCAG

CACGGGATTGGCACCTACTATATAACAGCTGTGCTGAGTGAGAGGCAGGA

GGGTGCTCAGCAGACACCCAGCTTGGTCTCGGTCATCACCGCCGTCACTC

AGTGTTACTACTGGGAGATCCACAACCAGACATGGAGCAGCGCCGGATGC

CAAGTTGGGCCAGAGAGCACAATTCTGAGGACACAGTGTCTCTGTAACCA

CCTGACCTTCTTTGCCAGCGACTTCTTTGTGGTGCCCAGGACCGTGAATG

TTGAAGACACGATCAAACTGTTCCTTCGCGTGACCAACAATCCTGTTGGG

GTGTCACTGCTGGCCAGCCTTTTAGGATTTTATGTGATCACAGTTGTGTG

GGCTCGGAAAAAGGATCAAGCAGATATGCAGAAGGTGAAGGTCACTGTCC

TGGCTGATAATGACCCCAGCGCTCAATTTCACTACCTTATTCAGGTCTAC

ACCGGATATCGAAGAAGCGCTGCTACAACAGCTAAGGTTGTCATCACCCT

CTATGGATCAGAGGGACGGAGTGAGCCCCATCACCTCTGTGACCCCAGA

AGACAGTCTTTGAACGAGGGGGCCTGGATGTCTTCCTTCTCACCACTTGG

ACCTCTCTAGGGAACCTGCACAGCCTTCGGCTCTGGCATGACAATTCTGG

CGTCAGTCCCTCCTGGTATGTCAGCCAGGTAATTGTCTGTGACATGGCAG

TTAAGAGGAAGTGGCATTTCCTGTGCAATTGCTGGCTGGCTGTGGACCTC

GGAGACTGTGAGCTTGACCGGGTCTTCATCCCAGTTTCAAAGAGAGAGCT

CTTTTCCTTTAGACATCTGTTTTCCTCCATGATTGTGGAAAAGTTCACCC

AGGATTATCTGTGGCTTTCAATTGCAACTCGGCATCCCTGGAACCAGTTT

ACAAGGGTCCAACGGCTGTCTTGCTGCATGACACTGCTACTCTGCAACAT

GGTCATCAATGTTATGTTCTGGAAGATAAACAGCACCACTGCCAAGAGAG

ATGAGCAAATGCGTCCATTTGCTGTGGCCTGGTCTGAACTGCTGGTCAGC

ATCCATACTGCTGTCATCCTCTTCCCAATCAATCTTGTCATAGGGCGGCT

CTTCCCGTTGATTGAGCCACAGGAGACTCTGCCCCTCTTTCCTCCCATCC

AGGCCTCCTGCCTCTCAGATGCTTCTGTTGAGCCTCTCTCTGCCACAATG

GTAGTTGAGGAATTAAAGGAAACTGTGAGATTCCTGCTCAGGAGAAATAC

ATACCTACTCTCCAAGTGTGAGCAGCCGCCATGGAGTTCTTGGGACATTA

CTAAGCTGGTGAAACTTTTATCCAGCCTCGTATCATCTCACTTGGAGGGT

CAAGGCTGTCATCAGCAGGGAGAGCGCCACTGGGCACGTGTTGTTCCTGA

AAACCACCATCATTTCTGCTGTTACCTGCATAGAGTTCTGCAGAGGCTGA

AATCTCACTTAGGCACGCTGGGTCTCACCCAGGGTCACCAGTCCTGTGAC

TTCCTAGATGCAGCCAGCCAACTTCAAAAACTCCAGGAACTCTTGGAAAC

ACATATTCTTCCCACGGAGCAAGAGCCATCCAGGGAAGTCACCAGTTTTG

CCATCCTGAGCTCAGAAGAAGGAAAAAAGCCCATCTCAAATGGCCTGTCC

-continued

```
AAATGGTTGACTTCAGTCTGCTGGCTCCTCTTAGGTTTCACTAGCCTGGC
TTCAGCCTTTTTTACAGCACTTTATAGCTTGGAATTGAGCAAAGACCAAG
CCACCAGCTGGATGATTTCAATTATTTTATCAGTGCTTCAGAACATCTTC
ATCAGCCAGCCAGTAAAGGTGGTCTTCTTCACATTCTTATACTCACTGAT
GATGAGCAGGATGCCACGGCTTAACAAAGAGAATGAACAACAAAGGATCT
TGGCACTCTTGGCAAAATGTTCTTCGTCAGTACCAGGTTCAAGAGATAAG
AACAACCCCGTCTATGTAGCCCCAGCTATAAATAGTCCAACTAAGCACCC
AGAAAGAACCTTGAAAAAGAAGAAACTCTTCAAGCTGACTGGAGATATTT
TGGTACAAATCCTCTTCCTTTACCCTGTTGATGACTGCAATCTACTCGCA
AAGAACTCCAATAGATTTTACCTCCACCAAGCTATCTGGAAGACATTTTC
GCACCAGTTCTCGGAAATCAAACTTCTTCAGGATTTCTACCCCTGGGCCA
ATCATATCCTTCTTCCTAGCCTGTATGGGGATTACAGAGGTAAGAATGCA
GTCCTGGAGCCCAGTCATTGCAAATGTGGGGTACAATTAATTTTCCAAAT
ACCCCGTACCAAGACCTATGAGAAAGTGGACGAAGGTCAGCTGGCGTTTT
GTGATAACGGCCATACCTGTGGGCGTCCCAAGAGCCTATTCGGTGGACTT
CATCTAAGGAGGTTCAGTTACATGTGTTCACCCAGGCCCATGGTGGTGAT
TCCCACTGATGAGCTTCACGAAAGGCTGACAAGCAAGAATGAGAATGGAT
TCAGTTACATCATGAGAGGTGCTTTCTTCACCTCTTTGAGACTGGAAAGC
TTCACTTCCCTTCAGATGTCAAAGAAGGGCTGTGTCTGGTCTATCATCTC
ACAAGTCATCTATTATCTACTGGTCTGTTACTATGCCTTCATACAGGGTT
GTCAGCTGAAACAGCAGAAGTGGAGGTTCTTCACTGGGAAAAGAAACATT
CTGGACACAAGTATAATCCTCATTAGCTTCATCGTCCTGGGGCTTGACAT
GAAGAGTATTTCTCTACATAAGAAAAACATGGCACGATACCGCGATGACC
AGGACAGATTCATCAGCTTCTATGAGGCAGTAAAAGTGAACTCTGCTGCG
ACTCACCTTGTGGGCTTCCCGGTTCTCCTGGGAACTGTTCAGTTATGGAA
CGTGCTGCGTCATAGCCCCAGGCTGCGGGTCATCAGCAGGACACTGAGCC
GAGCCTGGGACGAGGTGGTGGGGTTTCTGCTGATCATCCTAATCGTGCTG
ACAGGCTATGCCATTGCCTTTAACCTGCTGTTTGGATGCAGCATCTCTGA
CTACCGGACATTTTTCAGCTCAGCAGTGACTGTTGTTGGTCTCCTGATGG
GAATTTCTCACCAAGAGGAGGTTTTCGCTTTAGACCCAGTCCTGGGCACC
TTTCTGATCCTCACCAGTGTCATCTTGATGGTACTTGTGGTAATTAATCT
TTTCGTTTCGGCCATTCTCATGGCCTTTGGAAAAGAAAGAAAGTCGCTTA
AGAAAGAAGCTGCACTAATAGATACACTGCTACAGAAGCTCTCAAATTTG
TTAGGAATCAGTTGGCCCCAAAAAACCTCATCTGAGCAAGCAGCCACGAC
AGCAGTGGGCAGTGACACTGAAGTTTTAGATGAACTACCTTAA
```

Example 3

A Common Sensor for Acid Detection in the Tongue and Spinal Cord

Mammals taste many compounds, yet use a sensory palette consisting of only five basic taste modalities: sweet, bitter, sour, salty, and umami (the taste of monosodium glutamate)[1,2]. While this repertoire may appear modest, it provides animals with critical information about the nature and quality of food. Sour taste detection functions as an important sensory input to warn against the ingestion of acidic (e.g. spoiled or unripe) food sources[1-3]. We have used a combination of bioinformatics, genetic, and functional studies to identify PKD2L1, a polycystic kidney disease-like ion channel[4], as a candidate mammalian sour taste sensor. In the tongue, PKD2L1 is expressed in a subset of taste receptor cells (TRCs) distinct from those responsible for sweet, bitter and umami taste. To examine the role of PKD2L1-expressing taste cells in vivo, we engineered mice with targeted genetic ablations of selected populations of TRCs. Animals lacking PKD2L1-cells are completely devoid of taste responses to sour stimuli. Notably, responses to all other tastants remained unaffected, proving that the segregation of taste qualities even extends to ionic stimuli. Our results now establish independent cellular substrates for four of the five basic taste modalities, and support a comprehensive labeled-line mode of taste coding at the periphery[5-10]. Interestingly, PKD2L1 is also expressed in specific neurons surrounding the central canal of the spinal cord. Here we demonstrate that these PKD2L1-expressing neurons send projections to the central canal, and selectively trigger action potentials in response to decreases in extracellular pH. We show that these cells correspond to the long sought components of the cerebrospinal fluid chemosensory system[11]. Taken together, our results suggest a common basis for acid sensing in disparately different physiological settings.

A broad range of cell types, receptors and mechanisms have been proposed to mediate salt and acid sensing in TRCs[1-3]. These include the activation of ENaCs, ASICs, K2P channels, H+-gated calcium channels, as well as the involvement of Na+-H+-exchangers, TRPV pain receptors, and even acid-inactivation of K+-channels[1-3,12-14]. Significantly, most of these proteins are broadly expressed in TRCs and other tissues. In contrast, we previously isolated and characterized the receptors for sweet, umami and bitter taste[5-7,15-17], and showed that each of these three taste modalities is mediated by highly selective receptor proteins expressed in distinct and independent populations of taste receptor cells[5-10]. Therefore, we reasoned that salt and sour taste should also be mediated by highly selective dedicated cells, and consequently expected the receptor proteins to be very exclusive in their expression pattern.

To identify novel taste receptors, we developed a multi-step bioinformatics and expression screening strategy (see also, Examples 1 and 2). First, since sensory receptors are expected to be membrane proteins, approximately 30,000 mouse open reading frames (ORFs) were scanned for the presence of at least one putative transmembrane segment. Second, because taste receptors are predicted to be very restricted in their expression pattern, ORFs encoding candidate transmembrane proteins were cross-searched against mouse EST databases to eliminate those broadly expressed. Next, to identify the subset specifically enriched in taste tissue, ORFs selected as encoding transcripts infrequently represented in EST databases (~880 candidates) were used in RT-PCR reactions templated with mRNA from TRCs versus control tongue epithelium. Finally, given that our goal was to discover membrane proteins selectively expressed in subsets of TRCs (and ideally not in sweet, bitter or umami sensing cells), we carried out detailed in situ hybridizations against taste papillae. Of 26 cDNAs used in situ studies, five were found to robustly and selectively label subsets of TRCs. FIG. 8 shows that one of these candidates, PKD2L1 is expressed in TRCs of all taste papillae, including fungiform, circumvallate, foliate and palate taste buds (further figure details are found below).

PKD2L1 encodes a polypeptide displaying significant amino acid sequence similarity to PKD2[4], a gene mutated in many cases of autosomal dominant polycystic kidney disease[18,19]. PKD2s are members of the TRP superfamily of ion channels[20], and have been recently shown to function as non-selective cation channels when expressed in heterologous cells[18,19,21]. While the exact roles of PKDs remain unknown, they are believed to function as receptor/ion-channel complexes, often localized to ciliated compartments, and implicated in sensing extracellular signals (e.g. in renal epithelial cells[18,19]). We reasoned that if PKD2L1 has a specific role in taste it should be expressed in subpopulations of taste receptor cells with unique functional characteristics. To determine which type of TRCs express PKD2L1, we performed double labeling experiments with sweet, umami and bitter taste receptors (T1Rs and T2Rs), as well as TRPM5, the transduction channel of sweet, bitter and umami sensing cells. Our results (FIG. 8) established that PKD2L1 is expressed in cells distinct from those mediating sweet, umami and bitter taste (see also[22]) FIGS. 1 and 8 show that PKD2L1 is expressed in a novel population of TRCs. As shown in FIG. 8, in situ hybridization (PKD2L1, PKD1L3, T1Rs, T2Rs and TRPM5) and double-label fluorescent immunohistochemistry (PKD2L1) were used to directly examine the overlap in cellular expression of taste receptors, TRPM5, PKD2L1 and PKD1L3. Panel A shows in situ hybridization of PKD2L1 and PKD1L3 against circumvallate, foliate, fungiform and palate taste buds, illustrating expression of PKD2L1 in subsets of TRCs of all taste buds, but a total lack of PKD1L3 in fungiform and palate TRCs. Approximately 20% of taste cells express PKD2L1. Dotted lines show the outline of sample taste buds. Panel (b) shows that PKD2L1 is not expressed in sweet, umami or bitter cells. The first three panels show co-labeling with a PKD2L1 antisense RNA probe and T1R3 (T1R, sweet and umami cells), a mixture of 20 T2Rs (bitter cells), and TRPM5 (sweet, umami and bitter cells), respectively. The last panel shows co-labeling with anti-PKD2L1 antibodies and an antisense PKD1L3 RNA probe. Note the absence of overlap between PKD2L1-expressing cells and those expressing sweet, umami or bitter receptors. However, PKD1L3 is always co-expressed with PKD2L1 in CV and foliate papillae.

Figure 9:
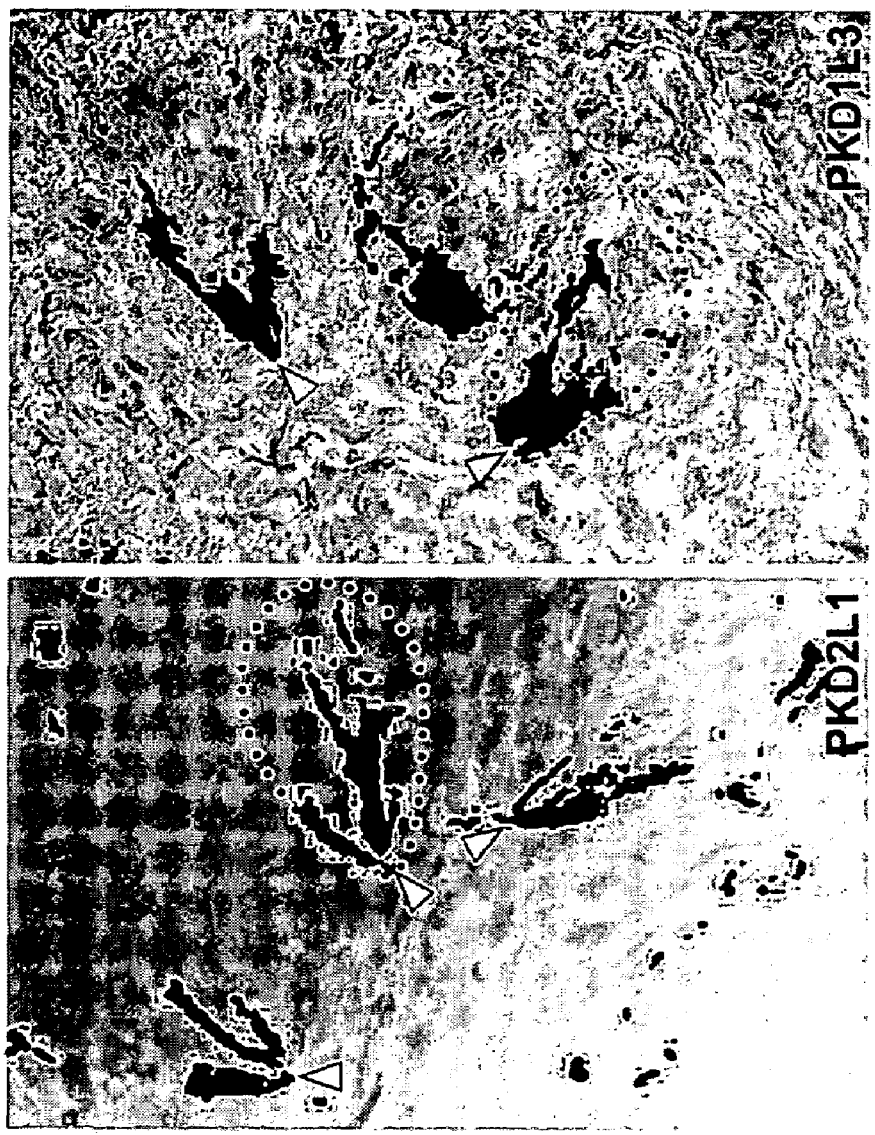
FIG. 9 shows antibody in situ hybridization results for binding of antibodies to PKD1L3 and PKD2L1.

Mammalian taste receptor cells project specialized apical microvilli to the taste pore, the site of interaction between tastants and taste receptor proteins. All known taste receptor proteins localize to, and function, in this TRC compartment[1,5-7,15,17,23]. Therefore we would expect bona-fide candidate receptors to also be enriched in the taste pore. We generated antibodies to PKD2L1 and used them in immunofluorescence staining of tongue tissue sections. Examination of CV, foliate and fungiform papillae demonstrated that PKD2L1 protein is indeed enriched in the apical surface of taste receptor cells, with the antibodies robustly labeling the taste pore region (FIG. 9). These results implicate PKD2L1 as part of the taste sensing machinery.

PKD2 isoforms often require PKD1s for functional expression at the cell surface[18,19,21]. The mammalian genome contains 4 members of the PKD1 family: PKD1, PKD1L1, PKD1L2 and PKD1 L3[18,19]. We performed in situ hybridization studies with gene specific probes representing each family member, and determined that PKD1L3 is specifically co-expressed with PKD2L1 in CV and foliate TRCs (FIG. 8, see also, Example 2, and[22]). We also generated antibodies to PKD1L3 and demonstrated selective co-expression with PKD2L1 in non-TRPM5 expressing cells of the CV and foliate (FIG. 9). Surprisingly, PKD1L3 transcript or protein is not detectable in fungiform or palate taste buds (FIGS. 8 and 9), suggesting that a different partner may be expressed in those TRCs.

If PKD2L1 is a mammalian taste receptor, we expect two basic criteria to be met. First, PKD2L1-expressing TRCs should mediate a specific taste quality in vivo. Second, PKD2L1 protein should be activated in response to taste stimuli.

To functionally dissect the role of PKD2L1-expressing cells in the tongue, we engineered mice where these cells were genetically ablated by targeted expression of attenuated diphtheria toxin[24] (DTA). To validate this approach as a means of uncovering TRC function, we first generated mice where T1R2-regulatory sequences were used to target DTA expression[25]. T1R2 is an essential subunit of the sweet receptor heterodimer (T1R2+3), and the selective ablation of these cells should generate animals with a specific loss of sweet taste[6,9,10,17]. To investigate the taste responses of the genetically modified mice, we recorded tastant-induced action potentials from nerves innervating taste receptor cells of the tongue; this physiological assay monitors the activity of the taste system at the periphery, and provides an accurate and reliable measure of taste receptor cell function. Indeed, animals expressing DTA in T1R2 cells have an extraordinary loss of sweet, but importantly retain umami, bitter, sour and salty tastes (FIG. 5, panel A). These results further substantiate the exquisite segregation of taste modalities at the periphery, and demonstrate the utility of using DTA-mediated ablation of TRCs as a strategy for dissecting taste system function. Next, we engineered animals where the PKD2L1 gene was used to target Cre recombinase into PKD2L1-expressing cells; appropriate expression was confirmed by performing double labeling with Cre and probes specific to PKD2L1-cells, or by crossing them to GFP reporter lines[26]. Mice expressing Cre in PKD2L1 cells were crossed to conditional DTA lines, and double-positive progeny were scrutinized both for the specificity and efficiency of killing, as well as the integrity of taste buds. We checked the expression of T1Rs, T2R5, and TRPM5[8,27] in control and DTA-expressing animals, and found no significant differences in the number or distribution of T1R- or T2R-positive cells between wild type and ablated taste tissue. In contrast, the DTA-targeted mice had a profound and practically complete loss of PKD2L1-expressing TRCs in the tongue. Remarkably, genetic ablation of the PKD2 L1-expressing cells produces animals with a devastating loss of sour taste (FIG. 5, panels A and B). Responses to all acid tastants, including citric acid, HCl, tartaric acid and acetic acid are completely abolished, with no significant activity over a range of 5 orders magnitude of proton concentrations. However, responses to sweet, umami, bitter or salty tastants remain indistinguishable from wild type control animals. These results firmly establish PKD2L1-expressing cells as the sour taste sensors, and further substantiate a model of coding at the periphery in which individual taste modalities operate independently of each other.

Acid sensing is important not only in the taste system, but also for monitoring the functional state of body fluids, including the internal milieu of the brain. This is particularly well-studied in the central and peripheral control of respiration, where pH sensing is the principal mechanism for monitoring $CO_2$ levels in the blood and cerebrospinal fluid[11,28,29] (CSF). Thus, we wondered whether PKD2L1 might be expressed in additional cell types, and if so whether such cells may also be involved in pH sensing in other physiological systems.

We carried out in situ hybridization and antibody staining experiments with PKD2L1 on a wide range of other tissues and identified a singular additional domain of expression: a discrete population of neurons surrounding the central canal of the spinal cord, through its entire length, from its origin in the brain stem to its end around the cauda equina (FIG. 6). Notably, these neurons send processes into the central canal, suggesting they may function as chemoreceptors sensing the internal state of the CSF (FIG. 6, e.g., panels b and g[11]). Given their anatomical distribution and cellular morphology, we reasoned these cells might be part of the homeostatic circuitry responsible for monitoring and reporting the pH of the cerebrospinal fluid. This postulate predicts that these neurons should trigger action potentials in response to acid stimulation. Therefore, we engineered mice where a GFP reporter was targeted to PKD2L1-expressing cells, and performed patch clamp recordings from GFP-labeled cells in a spinal cord slice preparation[30]. A priori, we anticipated some notable differences in the behavior of these cells compared to TRCs; while the taste system is tuned to respond to acid stimulation in the range of multiple pH units (i.e. pH 2-5), we expected the CSF monitor cells to respond to pH changes within a range of a few tenths of deviation from pH 7.4. Indeed, FIG. 7 shows that the PKD2L1-expressing neurons display exquisite sensitivity and selectivity to pH stimulation. Exposure to test solutions between pH 6.5 and 7.4 evoked a dramatic, dose dependent, and reversible increase in action potential (AP) frequency (FIG. 7). In contrast, the same acid stimuli have no significant impact on the response of control (e.g. unlabeled) cells, even after exposure to pH as low as 6.5 (lower pHs triggered irreversible damage to the slice preparation).

Most of the known CSF-contacting neurons in mammals project ciliated dendrites into the CSF, where they are proposed to sense fluid flow, pressure, pH or the composition of the CSF[11]. Our demonstration that PKD2L1-expressing cells of the spinal cord selectively fire in response to minor changes in proton concentration strongly suggests that they function as sentinels of cerebrospinal and ventricular pH. Collectively, these results assign an entirely unexpected role to members of the PKD family of proteins, offer a new perspective into the potential significance of PKD2s in health and disease, and bring forth a surprising unity in the cellular basis of pH sensing in very different physiological systems. It is useful to develop an activity assay for PKD2L1 to establish the molecular mechanism of acid activation, to study the phenotype of PKD2L1 knockout animals, and determine whether PKD2L1 functionally associates or interacts with different partners in different cells types. In this regard, it would be worth exploring whether the differences in pH sensitivity between the tongue and spinal cord might be due to differences in PKD2L1-receptor complex composition.

The nature of the mammalian sour taste receptor and sour-sensing TRCs have been fertile ground for speculation over the years. A wide range of cell types, receptors, and even receptor-independent mechanisms, have been proposed to mediate acid detection in the tongue[1-3]. The results presented in this paper establish that sour taste, much like our previous findings for sweet, umami and bitter is mediated by a unique cell type, independent of all other taste qualities. In addition, our demonstration that sour-less mice have normal salt responses demonstrates that salt taste is also mediated by independent TRCs. Together, these results impose a considerable revision of the current views of taste representation at the periphery, and make a compelling case for a labeled line mode of coding across all five taste modalities and TRC types.

Accordingly, several lines of evidence now strongly implicate PKD2L1 as encoding a receptor protein. First, expressed PKD2L1 mRNA and polycystin-2L1 selectively localize to the taste pore region of TRCs. Second, the presence of polycystin-2L1 protein functionally marks cells as acid chemosensors, both in the tongue and in the nervous system. Finally, ablation of PKD211-expressing cells selectively eliminates pH-sensing in the tongue. It is of interest to further study the phenotype of PKD2L1 knockout animals, to establish the molecular mechanism of acid activation, and to further determine whether PKD2L1 functionally associates or interacts with different partners in different cells types. In this regard, it would be worth exploring whether the differences in pH sensitivity between the tongue and spinal cord might be due to differences in PKD2L1-receptor complex composition.

Additional Example Details

Molecular Cloning of PKD2L1

We used a strategy that combined bioinformatics and differential screening to isolate genes specifically expressed in taste receptor cells. Mouse genomic sequence information was obtained from Ensembl Mm.30 (http://www.ensembl.org). Approximately 30,000 predicted protein sequences were screened for the presence of at least one putative transmembrane segment, using both TMHMM server version 2.0 (http://www.cbs.dtu.dk/services/TMHMM-2.0/) and f_TMHMM (San Diego Supercomputer center, http://www.sdsc.edu/pb/Group.html). The cDNA sequence for each candidate membrane protein was then extracted from NCBI (http://www.ncbi.nlm.nih.gov/blast/blastcgihelp.shtml#nucleotide_databases) and used to screen EST databases (http://www.ncbi.nlm.nih.gov/dbEST/index.html). Only EST hits with e-values of less than or equal to $e^{-100}$ were considered in our analysis. A total of 884 genes expressed in 3 tissues or less were chosen for PCR reactions with cDNA prepared from taste papillae mRNA (CV and foliate) and from surrounding non-taste epithelial tissue (non-taste control). To ensure specificity of the PCR reactions, all primers sets included unique 3UTR sequences (http://frodo.wi.mit.edu/cgi-bin/primer3/primer3_www.cgi.). A total of 98 genes showed selective enrichment in taste versus non-taste tissue, and of these five were robustly expressed in subsets of TRCs. Full length clones were isolated from mouse taste cDNA libraries[23]. See also, Examples 1 and 2.

In Situ Hybridization and Immunostaining

Fresh frozen sections (16 μm/section) were attached to silanized slides and prepared for immunohistochemistry or in situ hybridization as described previously[23]. In situ hybridizations were carried out using digoxigenin or fluorescein labeled probes at high stringency (hybridization, 5×SSC, 50% formamide, 65-72° C.; washing, 0.2×SSC, 72° C.). For single-label detection, signals were developed using alkaline phosphatase-conjugated antibodies to digoxigenin and standard chromogenic substrates. Double-label fluorescent detection utilized an alkaline phosphatase-conjugated anti-fluorescein antibody and a horseradish peroxidase-conjugated anti-digoxigenin antibody in combination with fast red and tyramide fluorogenic substrates[23].

Anti-peptide antibodies to PKD2L1 (KLKMLERKGELAPSPGMGE, SEQ ID NO:18), PKD1L3 (DFQEADNYCHAQRGRLAHT, SEQ ID NO:19), and TRPM5[8] were generated in rabbits and purified as described previously[31]. Images were obtained using either a Leica SP2 TSC or a Zeiss 510 Meta confocal microscope; 1-2 μm optical sections were recorded to ensure that any overlapping signal originated from single cells. For double label experiments, in situ hybridization was carried out before immunohistochemical detection.

Transgenic Animals

Transgenic lines were produced by pronuclear injection of zygotes from FVB/N or CB6 (BALB/c×C57BL/6 hybrids) mice. The PKD2L1-IRES-Cre construct was generated in RP23-297K23 and the TR2-IRES-Cre in RP23-348G10 (http://bacpac.chori.org/) using a 4 kb IRES-Cre cassette (gift from Dr. Kevin Jones). Recombination was carried out exactly as described previously[32]. All products were characterized by restriction analysis and direct sequencing to ensure fidelity of the recombination event and junctional sequences. Z/EG reporter lines[26] were obtained from Jackson Laboratories (Bar Harbor, Me.; Novak et al., 2000), and Rosa26-flox-lacZ-flox-DTA animals[25] were a generous gift of Dr. Dieter Riethmacher.

Nerve Recordings

Lingual stimulation and recording procedures were performed as previously described[7,9]. Neural signals were amplified (10,000×) with a Grass P511 AC amplifier (Astro-Med), digitized with a Digidata 1200B A/D converter (Axon Instruments), and integrated (r.m.s. voltage) with a time constant of 0.5 s. Taste stimuli were presented at a constant flow rate of 4 ml min$^{-1}$ for 20 s intervals interspersed by 2 min rinses with artificial saliva[7,9] between presentations. All data analyses used the integrated response over a 25 s period immediately after the application of the stimulus. The mean response to 60 mM AceK was used to normalize responses to each experimental series. Tastants used for nerve recordings were: 10 mM, 60 mM acesulfameK (AceK); 10 mM, 60 mM sodium saccharin (saccharin); 300 mM sucrose; 30 mM mono potassium glutamate+1 mM inosine mono phosphate (Glu); 30 mM L alanine+1 mM inosine mono phosphate (Ala); 10 mM quinine hydrochloride (Qui); 100 µM cycloheximide (Cyx); 10 mM 6-n-propyl 2-thiouracil (PROP); 50 mM, 100 mM sodium chloride (NaCl); 10 mM, 50 mM citric acid; 10 mM, 50 mM tartaric acid; 50 mM, 500 mM acetic acid; pH 2 hydrochloric acid (HCl); 10 mM citric acid pH 2, 4 and 6.

Spinal Cord Slice Recordings

Electrophysiological experiments were performed on P1-P4 mice as previously described[30]. Spinal cord slices 250-300 µm thick were generated using a Vibratome® 3000 Plus at 0-4° C. in a modified Ringers' solution (0.5 mM $CaCl_2$, 3.7 mM $MgSO_4$). After at least a 1 h recovery period, slices were transferred to a recording chamber and perfused with oxygenated Ringers' solution (pH 7.4) at room temperature. Loose-patch and whole-cell patch clamp recordings from GFP-labeled and unlabeled cells were performed using an EPC-10/2 amplifier and Patchmaster software (HEKA Elektronik). Slices were stimulated with a solution containing 140 mM NaCl, 3 mM KCl, 1.3 mM $MgSO_4$, 2.5 mM $CaCl_2$, 10 mM glucose, 10 mM HEPES at various pH (7.4, 6.9, 6.5).

Additional Figure Details

Figure 5A:
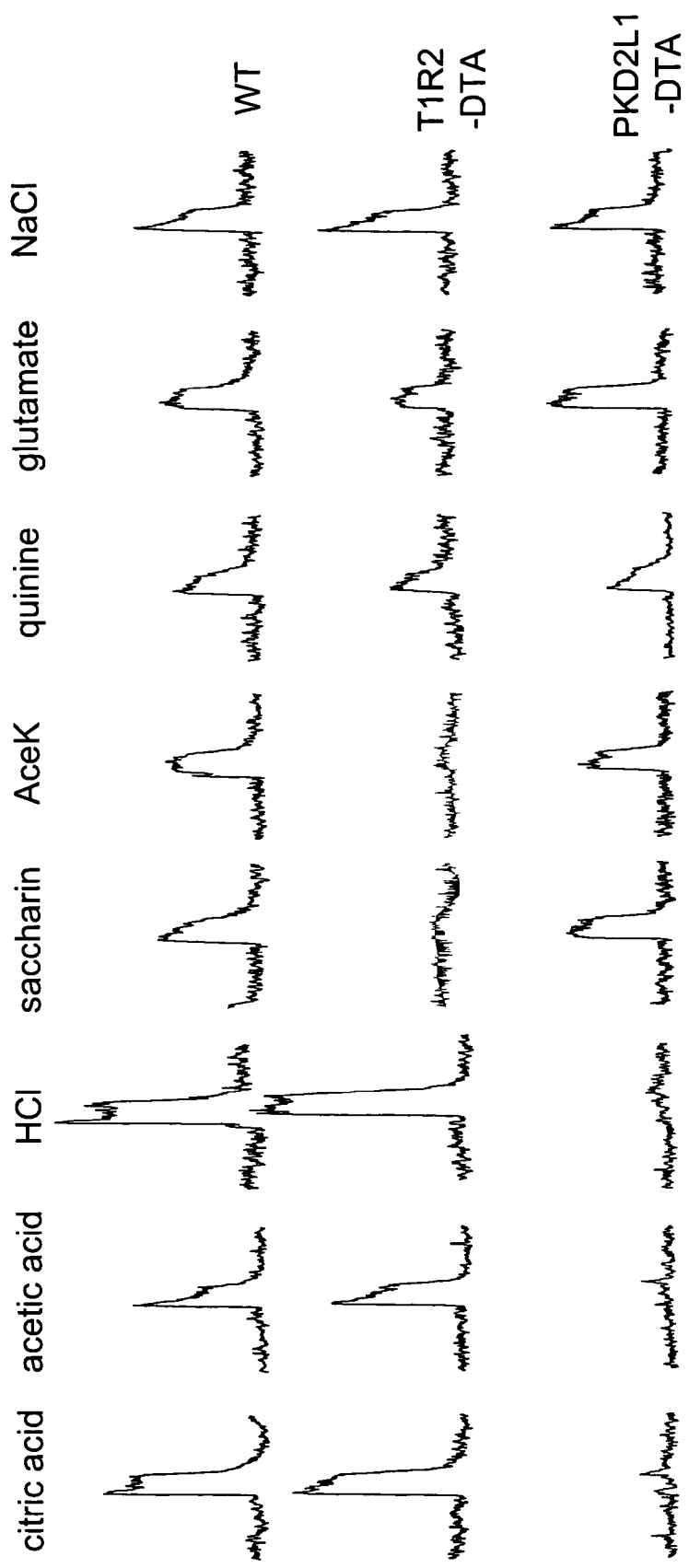
FIG. 5, Panels A show a series of traces showing the taste impact of eliminating cells expressing PKD2L1 in the tongue. Note the total loss of sour taste in nerve responses. As a control also included are wild type mice (upper traces) and engineered animals where sweet cells have been ablated (middle traces). Panel B shows histograms of response for wild-type and ablated animals.
Figure 5B:
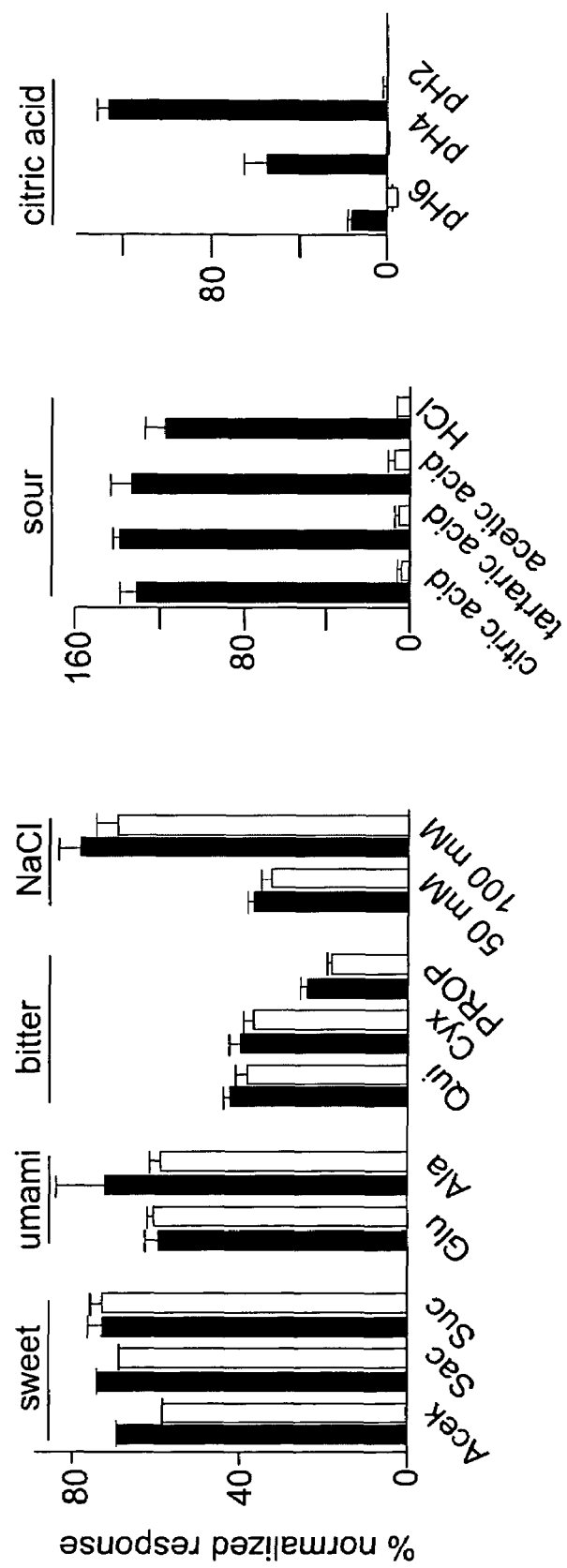
Figure 6C:
FIG. 6, panels A-G shows PKD2L1 expression in cells surrounding the central canal.
Figure 6B:
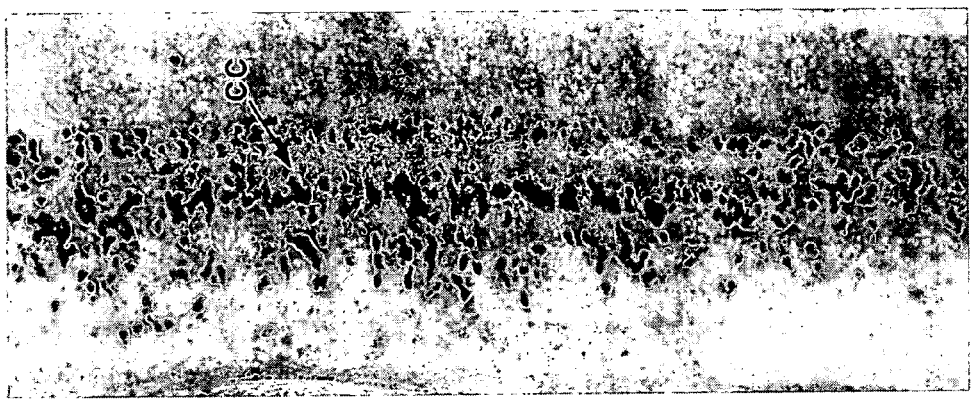
Figure 6A:
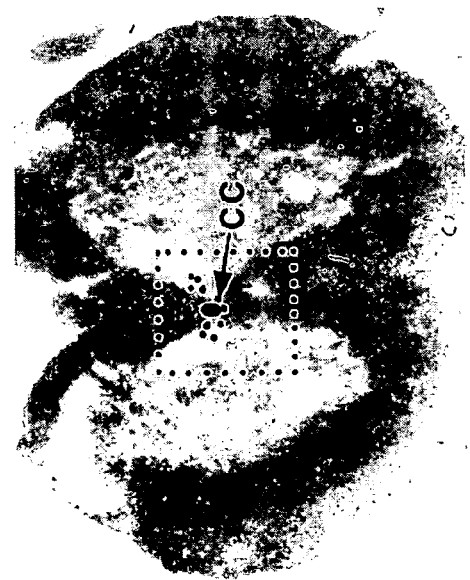
Figure 6G:
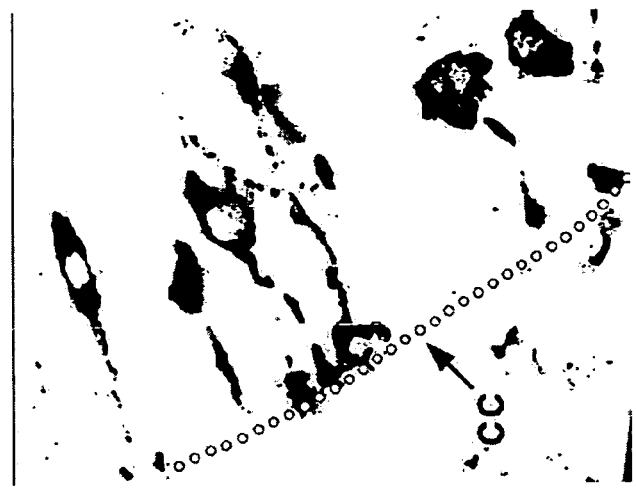
Figure 6F:
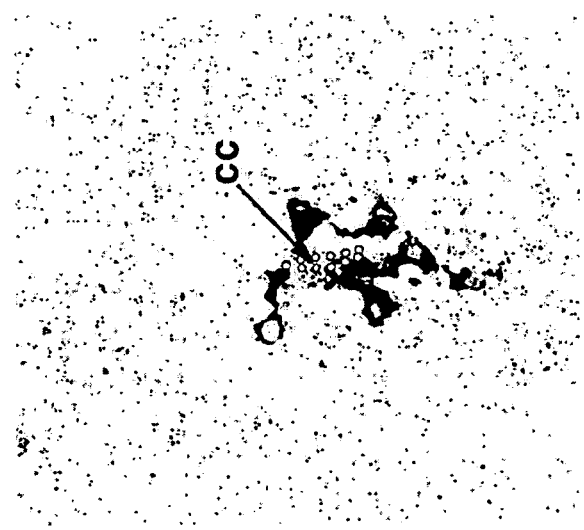
Figure 6D:
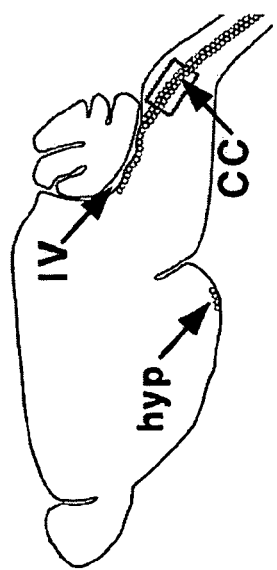
Figure 6E:

FIG. 5A-B: PKD2L1-expressing TRCs are the mediators of sour taste. (a) Targeted expression of attenuated diphtheria toxin to selective populations of TRCs produces animals with selective deficits in taste responses. Wild-type mice (WT) show robust neural responses to sweet (saccharin and acesulfameK, AceK), bitter (quinine), amino acid (glutamate), salty (NaCl) and sour tastants (citric acid, acetic acid and hydrochloric acid, HCl). However, ablation of sweet cells (T1R2-expressing TRCs) generates animals with a dramatic loss of sweet taste (middle panel). In contrast, ablation of PKD2 L1-expressing cells eliminates responses to all acid stimuli (bottom panel). Importantly, responses to all other taste qualities remain unimpaired in the DTA-expressing animals. Shown are integrated chorda tympani responses normalized to the response to 60 mM AceK; see herein for details on the ablated lines and concentrations of tastants. (b) Average neural responses of animals lacking PKD2L1-expressing cells to an expanded panel of tastants; note normal responses to sweet, umami, bitter and salt stimuli. Wild type, black bars; PKD2L1-DTA, outline bars. The values are means±s.e.m. (n=5) of normalized chorda tympani responses. (c) Quantitation of acid responses of wild type (gray bars) and PKD2L1-DTA animals (outline bars). The values are means±s.e.m. (n=6).

FIG. 6: PKD2L1 is expressed in neurons contacting the central canal of the spinal cord. (a-b) Antibody labeling with anti-PKD2L1 antibodies reveals a population of a population of PKD2L1 expressing neurons surrounding the central canal of the spinal cord. (b) expanded view of dotted area from panel (a). (c-d) The PKD2L1-expressing cells are found throughout the entire length of the spinal cord. Shown are in situ hybridization experiments with PKD2L1 specific probes on a sagital section of a P1 mouse. Section shown corresponds approximately to boxed area in panel (c). (e-f) PKD2L1-expression extends through the brain stem and into the IV ventricle (IV). There is also a very small group of positive cells in the hypothalamus. (g) PKD2L1-expressing neurons project into the central canal; note robust expression of PKD2L1 receptors at the terminals. Shown are immunofluorescent stainings with anti-PKD2L1 antibodies; cc refers to central canal.

FIG. 7: PKD2L1-expressing neurons of the central canal fire action potentials in response to pH stimulation Spinal cord neurons were patched using a loose patch configuration[30], tested for the presence of basal activity and recorded in the cell-attached configuration. (a) GFP-expressing (PKD2L1-positive cells) or unlabeled (control) cells were examined for pH responses under a perfusion regime consisting of pH 7.4, pH6.9, pH 7.4 and pH 6.5. (b) Shown are AP traces in a window of ~10 sec following exposure to test solutions at pH 7.4, 6.9 and 6.5. Note the dramatic increases in firing frequency in GFP-labeled cells. (c) Data was analyzed by examining records of ~4 minutes at each pH condition; spike sorting software (Axon Instruments) was used to calculate AP frequencies. Basal activity ranged between 1-5 Hz. A minimum of 8 GFP-labeled and 5 unlabelled cells were characterized for each stimuli. The values are means±s.e.m. normalized to basal activity at pH 7.4.

FIG. 8: PKD2L1 is expressed in a novel population of TRCs. In situ hybridization (PKD2L1, PKD1L3, T1Rs, T2Rs and TRPM5) and double-label fluorescent immunohistochemistry (PKD2L1) were used to directly examine the overlap in cellular expression of taste receptors, TRPM5, PKD2L1 and PKD1L3. (a) In situ hybridization of PKD2L1 and PKD1L3 against circumvallate, foliate, fungiform and palate taste buds illustrating expression of PKD2L1 in subsets of TRCs of all taste buds, but a total lack of PKD1L3 in fungiform and palate TRCs. Approximately 20% of taste cells express PKD2L1. Dotted lines show the outline of sample taste buds. (b) PKD2L1 is not in sweet, umami and bitter cells. The first three panels show co-labeling with a PKD2L1 antisense RNA probe (PKD) and T1R3 (T1R, sweet and umami cells), a mixture of 20 T2Rs (bitter cells), and TRPM5 (sweet, umami and bitter cells), respectively. The last panel shows co-labeling with anti-PKD2L1 antibodies and an antisense PKD1L3 RNA probe. Note the absence of overlap between PKD2L1-expressing cells and those expressing sweet, umami or bitter receptors. However, PKD1L3 is always co-expressed with PKD2L1 in CV and foliate papillae.

Figure 10A:
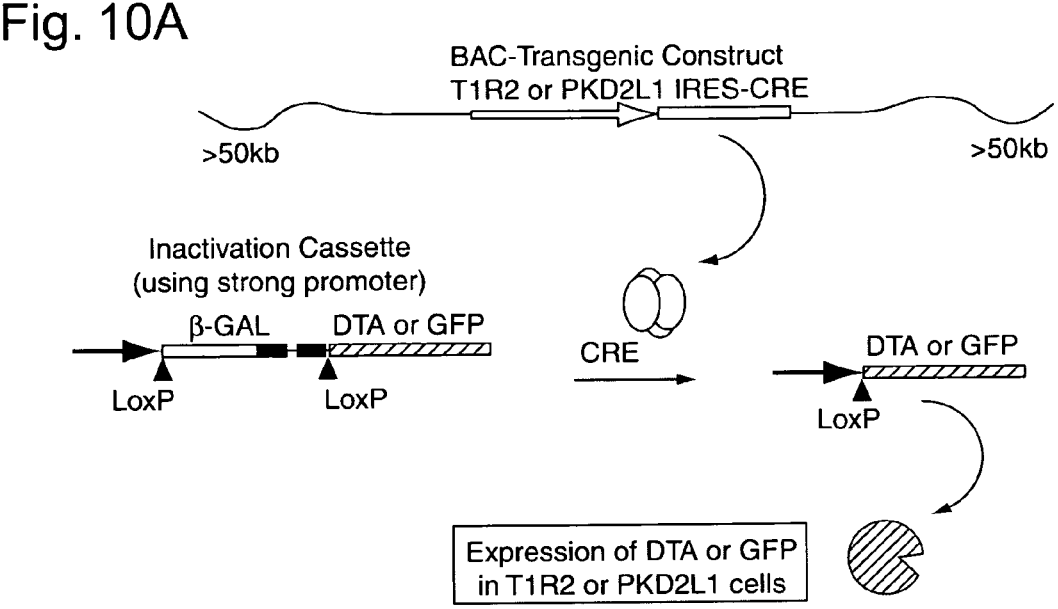
FIG. 10 illustrates loss of selective TRCs in DTA-expressing animals. Panel A Upper diagram illustrates the strategy used to target DTA or GFP to selective populations of TRCs. Panel B lower panels show in situ hybridization experiments examining the presence of sweet (T1Rs), bitter (T2Rs) or PKD2L1-expressing cells in the two engineered lines.
Figure 10B:
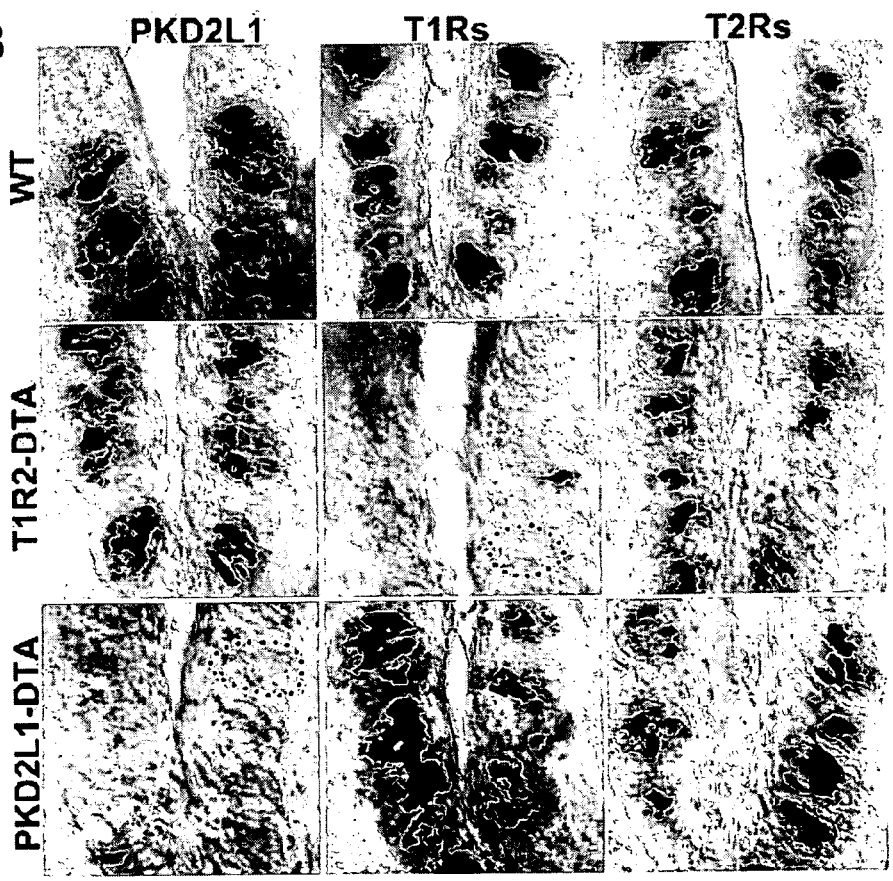

FIG. 9: PKD2L1 and PKD1L3 are enriched in the taste pore. Immunofluorescent stainings of mouse taste buds with PKD2L1 (left panel) and with PKD1 L3 (right panel) antibodies. The pictures show superposition of fluorescent antibody signals on DIC images of taste tissue. Dotted lines illustrate the outline of a taste bud, and arrows point to the taste pore region FIG. 10: Loss of selective TRCs in DTA-expressing animals. Upper diagram illustrates the strategy used to target DTA or GFP to selective populations of TRCs. BAC constructs contained the entire T1R2 or PKD2L1 genes with the IRES-Cre added downstream of the termination codon, but upstream of polyA-addition signals. In both cases, the transgenic constructs included at least 50 Kb of flanking sequences upstream and downstream of the target gene (see Methods). Fidelity of Cre and reporter expression in the correct cell types was confirmed by double labeling with a variety of TRC-specific gene probes. Lower panels show in situ hybridization experiments examining the presence of sweet (T1Rs), bitter (T2Rs) or PKD2L1-expressing cells in the two engineered lines. Targeting of DTA to T1R2- or PKD2L1-expressing cells eliminates over 95% of their respective TRC population. In situ hybridization probes were as in FIG. 8.

REFERENCES

1. Lindemann, B. Receptors and transduction in taste. *Nature* 413, 219-25 (2001).
2. Kinnamon, S.C. & Margolskee, R. F. Mechanisms of taste transduction. *Curr Opin Neurobiol* 6, 506-13 (1996).
3. DeSimone, J. A., Lyall, V., Heck, G. L. & Feldman, G. M. Acid detection by taste receptor cells. *Respir Physiol* 129, 231-45 (2001).
4. Wu, G. et al. Identification of PKD2L, a human PKD2-related gene: tissue-specific expression and mapping to chromosome 10q25. *Genomics* 54, 564-8 (1998).
5. Adler, E. et al. A novel family of mammalian taste receptors. *Cell* 100, 693-702 (2000).
6. Nelson, G. et al. Mammalian sweet taste receptors. *Cell* 106, 381-90 (2001).
7. Nelson, G. et al. An amino-acid taste receptor. *Nature* 416, 199-202 (2002).
8. Zhang, Y. et al. Coding of sweet, bitter, and umami tastes: different receptor cells sharing similar signaling pathways. *Cell* 112, 293-301 (2003).
9. Zhao, G. Q. et al. The receptors for mammalian sweet and umami taste. *Cell* 115, 255-66 (2003).
10. Mueller, K. L. et al. The receptors and coding logic for bitter taste. *Nature* 434, 225-9 (2005).
11. Vigh, B. et al. The system of cerebrospinal fluid-contacting neurons. Its supposed role in the nonsynaptic signal transmission of the brain. *Histol Histopathol* 19, 607-28 (2004).
12. Lyall, V. et al. The mammalian amiloride-insensitive non-specific salt taste receptor is a vanilloid receptor-1 variant. *J Physiol* 558, 147-59 (2004).
13. Richter, T. A., Dvoryanchikov, G. A., Chaudhari, N. & Roper, S. D. Acid-sensitive two-pore domain potassium (K2P) channels in mouse taste buds. *J Neurophysiol* 92, 1928-36 (2004).
14. Vinnikova, A. K. et al. Na+—H+ exchange activity in taste receptor cells. *J Neurophysiol* 91, 1297-313 (2004).
15. Matsunami, H., Montmayeur, J. P. & Buck, L. B. A family of candidate taste receptors in human and mouse. *Nature* 404, 601-4 (2000).
16. Chandrashekar, J. et al. T2Rs function as bitter taste receptors. *Cell* 100, 703-11 (2000).
17. Li, X. et al. Human receptors for sweet and umami taste. *Proc Natl Acad Sci U S A* 99, 4692-6 (2002).
18. Nauli, S. M. et al. Polycystins 1 and 2 mediate mechanosensation in the primary cilium of kidney cells. *Nat Genet* 33, 129-37 (2003).
19. Delmas, P. Polycystins: polymodal receptor/ion-channel cellular sensors. *Pflugers Arch* 451, 264-76 (2005).
20. Clapham, D. E. TRP channels as cellular sensors. *Nature* 426, 517-24 (2003).
21. Murakami, M. et al. Genomic organization and functional analysis of murine PKD2L1. *J Biol Chem* 280, 5626-35 (2005).
22. Lopezjimenez, N. D. et al. Two members of the TRPP family of ion channels, Pkd1l3 and Pkd2l1, are co-expressed in a subset of taste receptor cells. *J Neurochem* 98, 68-77 (2006).
23. Hoon, M. A. et al. Putative mammalian taste receptors: a class of taste-specific GPCRs with distinct topographic selectivity. *Cell* 96, 541-51 (1999).
24. Collier, R. J. Diphtheria toxin: mode of action and structure. *Bacteriol Rev* 39, 54-85 (1975).
25. Brockschnieder, D. et al. Cell depletion due to diphtheria toxin fragment A after Cre-mediated recombination. *Mol Cell Biol* 24, 7636-42 (2004).
26. Novak, A., Guo, C., Yang, W., Nagy, A. & Lobe, C. G. Z/EG, a double reporter mouse line that expresses enhanced green fluorescent protein upon Cre-mediated excision. *Genesis* 28, 147-55 (2000).
27. Perez, C. A. et al. A transient receptor potential channel expressed in taste receptor cells. *Nat Neurosci* 5, 1169-76 (2002).
28. Lahiri, S. & Forster, R. E., 2nd. $CO_2/H(+)$ sensing: peripheral and central chemoreception. *Int J Biochem Cell Biol* 35, 1413-35 (2003).
29. Richerson, G. B., Wang, W., Hodges, M. R., Dohle, C. I. & Diez-Sampedro, A. Homing in on the specific phenotype(s) of central respiratory chemoreceptors. *Exp Physiol* 90, 259-66; discussion 266-9 (2005).
30. Gosgnach, S. et al. V1 spinal neurons regulate the speed of vertebrate locomotor outputs. *Nature* 440, 215-9 (2006).
31. Cassill, J. A., Whitney, M., Joazeiro, C. A., Becker, A. & Zuker, C. S. Isolation of *Drosophila* genes encoding G protein-coupled receptor kinases. *Proc Natl Acad Sci USA* 88, 11067-70 (1991).
32. Lee, E. C. et al. A highly efficient *Escherichia coli*-based chromosome engineering system adapted for recombinogenic targeting and subcloning of BAC DNA. *Genomics* 73, 56-65 (2001).

While the foregoing invention has been described in some detail for purposes of clarity and understanding, it will be clear to one skilled in the art from a reading of this disclosure that various changes in form and detail can be made without departing from the true scope of the invention. For example, all the methods, compositions and systems described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of detecting a behavior or physiological response modulated by a human polycystin-2L1 polypeptide, comprising:
   (a) obtaining a transgenic mouse which lacks endogenous polycystin-2L1 polypeptide expression and whose genome comprises a DNA sequence encoding a heterologous human polycystin-2L1 polypeptide operatively linked to a promoter in a taste bud of the transgenic mouse or in a neuron of the transgenic mouse in contact with the cerebro-spinal fluid (CSF) of the transgenic mouse;
   (b) providing a putative tastant or modulator of the heterologous human polycystin-2L1 polypeptide to the transgenic mouse and a control mouse; and
   (c) monitoring the behavior or physiological response of the transgenic mouse in response to the presence of the putative tastant or modulator, wherein said response is compared to a response of a control mouse to the putative tastant or modulator, wherein the control mouse does not express the heterologous human polycystin-2L1 polypeptide in the taste bud and in a neuron in contact with CSF of the control mouse.

2. The method of claim 1, wherein the behavior is a feeding behavior.

3. The method of claim 1, wherein the physiological response includes respiration.

4. The method of claim 1, wherein the gene comprises a heterologous promoter that is active in the taste bud of the transgenic mouse.

5. The method of claim 4, wherein the heterologous promoter is selected from the group consisting of: a polycystin-2L1 taste receptor gene promoter, a T1R-gene promoter, T2R-gene promoter, TRPM5-gene promoter, a PLCB2 gene promoter, a repeater gene promoter, a gustducin gene promoter, a Gi2 gene promoter, a cytokeratin-19 gene promoter, a promoter for a gene that is naturally selectively expressed in a taste receptor cell of the tongue or palate epithelium and a promoter for a gene that is naturally expressed in neurons in contact with the CSF.

6. The method of claim 1, wherein the tastant or modulator is provided on a licking device to the transgenic mouse and licking behavior of the transgenic mouse on the device is monitored.

7. The method of claim 1, wherein the modulator is injected into the transgenic mouse.

8. The method of claim 1, wherein the putative tastant or modulator is provided to the transgenic mouse in conjunction with a control compound and the relative frequency of feeding behavior between the putative tastant and the control compound is determined.

9. The method of claim 1, wherein the tastant or modulator comprises an agonist, enhancer, antagonist, or inverse agonist of polycystin-2L1.

10. A system for detecting a behavior or physiological response modulated by a human polycystin-2L1 polypeptide, the system comprising:
   (a) a transgenic mouse which lacks endogenous polycystin-2L1 polypeptide expression and whose genome comprises a DNA sequence encoding a heterologous human polycystin-2L1 polypeptide operatively linked to a promoter in a taste bud of the transgenic mouse or in a neuron of the transgenic mouse in contact with the cerebro-spinal fluid (CSF) of the transgenic mouse;
   (b) a control mouse that does not express the heterologous human polycystin-2L1 polypeptide in the taste bud and in a neuron in contact with CSF of the control mouse;
   (c) a source of a putative tastant or modulator of the heterologous human polycystin-2L1 polypeptide that is accessible or deliverable to the transgenic mouse and control mouse; and
   (d) a detector that detects a behavior or physiological response of the transgenic mouse and control mouse in response to the putative tastant or modulator.

11. The system of claim 10, wherein the transgenic mouse is a knock-out mouse deficient in endogenous polycystin-2L1 polypeptide expression, which transgenic mouse expresses a heterologous human polycystin-2L1 polypeptide.

12. The system of claim 10, wherein the source comprises a lickable device, a fluid source comprising the tastant or modulator, or a food source comprising the tastant or modulator.

13. The system of claim 10, wherein the detector comprises a camera that detects movement by the transgenic mouse.

14. The system of claim 10, wherein the detector comprises a device that detects respiration of the transgenic mouse.

15. The system of claim 10, wherein the system further comprises an analysis module operably linked to the detector, which analysis module analyzes information received from the detector.

16. The method of claim 1, wherein the putative tastant or modulator is orally delivered.

17. The system of claim 10, wherein the source is configured for oral delivery to the transgenic mouse.

* * * * *